(12) United States Patent
Harada et al.

(10) Patent No.: US 9,206,202 B2
(45) Date of Patent: Dec. 8, 2015

(54) CARBAZOLE DERIVATIVE AND SEMICONDUCTOR NANOCRYSTAL

(75) Inventors: Shigeyuki Harada, Shizuoka (JP); Masaomi Sasaki, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 646 days.

(21) Appl. No.: 13/434,166

(22) Filed: Mar. 29, 2012

(65) Prior Publication Data

US 2013/0026426 A1 Jan. 31, 2013

(30) Foreign Application Priority Data

Jul. 29, 2011 (JP) ................................ 2011-166230
Jan. 25, 2012 (JP) ................................ 2012-013021

(51) Int. Cl.
| | | |
|---|---|---|
| C07D 209/86 | (2006.01) | |
| C07F 7/08 | (2006.01) | |
| C07D 403/04 | (2006.01) | |
| C07D 209/82 | (2006.01) | |
| C07F 5/02 | (2006.01) | |
| C07D 409/04 | (2006.01) | |
| B82Y 30/00 | (2011.01) | |
| H01L 51/00 | (2006.01) | |

(52) U.S. Cl.
CPC ............... *C07F 7/0814* (2013.01); *B82Y 30/00* (2013.01); *C07D 209/82* (2013.01); *C07D 403/04* (2013.01); *C07D 409/04* (2013.01); *C07F 5/027* (2013.01); *H01L 51/0072* (2013.01); *H01L 51/0094* (2013.01); *H01L 51/0037* (2013.01); *H01L 2251/308* (2013.01)

(58) Field of Classification Search
USPC ........................................................ 548/444
See application file for complete search history.

(56) References Cited

U.S. PATENT DOCUMENTS

| | | | |
|---|---|---|---|
| 4,156,734 A | 5/1979 | Stone | |
| 7,166,689 B2 | 1/2007 | Sagisaka et al. | |
| 7,550,554 B2 | 6/2009 | Sagisaka et al. | |
| 8,765,903 B2 * | 7/2014 | Sasaki et al. | 528/394 |
| 2005/0084711 A1 * | 4/2005 | Sasaki et al. | 428/690 |
| 2010/0219405 A1 | 9/2010 | Sagisaka et al. | |
| 2012/0032115 A1 * | 2/2012 | Harada et al. | 252/301.16 |

FOREIGN PATENT DOCUMENTS

| | | | |
|---|---|---|---|
| EP | 2414392 A2 * | 2/2012 | |
| JP | 49-26277 | 3/1974 | |
| JP | 2003178884 A * | 6/2003 | |
| JP | 2004-095427 | 3/2004 | |
| JP | 2004087396 A * | 3/2004 | |
| JP | 2005-108855 | 4/2005 | |
| JP | 2005-158691 | 6/2005 | |
| JP | 2007-201193 | 8/2007 | |
| JP | 2007-537886 | 12/2007 | |
| JP | 2008-162913 | 7/2008 | |
| JP | 2009-504422 | 2/2009 | |
| JP | 2009-87754 | 4/2009 | |
| JP | 2009-514993 | 4/2009 | |
| JP | 2009-99545 | 5/2009 | |
| JP | 2009-527099 | 7/2009 | |
| JP | 2010-73987 | 4/2010 | |
| JP | 4762514 | 6/2011 | |
| WO | WO 2005/106082 A1 | 11/2005 | |
| WO | WO 2007/020416 A1 | 2/2007 | |
| WO | WO 2007/049052 A2 | 5/2007 | |
| WO | WO 2007/049052 A3 | 5/2007 | |
| WO | WO 2007/095173 A2 | 8/2007 | |
| WO | WO 2007/095173 A3 | 8/2007 | |
| WO | WO 2008/105398 | 9/2008 | |
| WO | WO 2009/122034 | 10/2009 | |
| WO | WO 2010/015824 A1 | 2/2010 | |

OTHER PUBLICATIONS

Office Action in corresponding Japanese Application No. 2012-013021, dated Aug. 11, 2015.
J. Jpn. Soc. Colour Mater., vol. 84, No. 12, 2011, pp. 408-414.

* cited by examiner

*Primary Examiner* — Nyeemah A Grazier
(74) *Attorney, Agent, or Firm* — Oblon, McClelland, Maier & Neustadt, L.L.P.

(57) ABSTRACT

A carbazole derivative represented by the following General Formula (1) where at least one aromatic ring has one to three substituents each represented by the following General Formula (2):

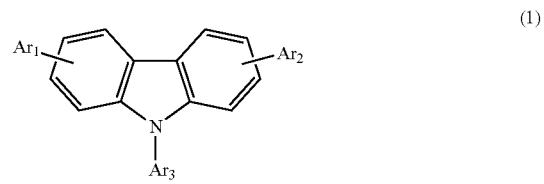

(1)

in General Formula (1), $Ar_1$ and $Ar_2$ each independently represent a substituted or unsubstituted aryl group which may form a ring with a benzene ring, a substituted or unsubstituted heterocyclic group, a substituted or unsubstituted arylsilyl group, or a hydrogen atom, and $Ar_3$ represents a substituted or unsubstituted aryl group,

—X—Y—Z                                            (2)

in General Formula (2), X represents a methylene group, a carbonyloxy group, an oxycarbonyl group, a carbonyl group, an oxygen atom or a sulfur atom, Y represents a substituted or unsubstituted alkylene group, and Z represents a carboxyl group, a hydroxyl group or a thiol group.

4 Claims, 16 Drawing Sheets

Wavelength (nm)

Wavelength (nm)

CARBAZOLE DERIVATIVE AND SEMICONDUCTOR NANOCRYSTAL

BACKGROUND OF THE INVENTION

1. Field of the Invention

The present invention relates to a novel carbazole derivative and a semiconductor nanocrystal containing this novel carbazole derivative bonded via a coordination bond or intermolecular force, where the semiconductor nanocrystal is effectively used for quantum dot-type organic EL elements with high light emission efficiency.

2. Description of the Related Art

In recent years, quantum dot-type organic EL elements have been proposed which use quantum dots of a semiconductor nanocrystal as a light emitting material. Nanoscaled small materials show intermediate behaviors between those as atoms or molecules and those as macroscopic solids (bulk form). Nanoscaled materials whose charged carriers and excitons are confined in all three-dimensional directions are called quantum dots, which increase in effective band gap with decreasing of their size. That is, when the size of quantum dots decreases, their absorption and light emission are shifted to the short wavelength side from the red region to the blue region. Also, by controlling quantum dots in composition and size in combination, it is possible to obtain a wide range of spectrum from the infrared region to the ultraviolet region. In addition, by controlling the distribution of sizes, it is possible to obtain a spectrum having a narrow half width and excellent color purity. By virtue of these characteristics, for example, there has been proposed a white light-emitting device having a light emitting layer containing several semiconductor nanocrystals (Japanese Patent Application Laid-Open (JP-A) No. 2009-527099). However, this proposal is unsatisfactory in light emission efficiency since the external quantum efficiency is about 0.3% to about 0.4%.

In order to efficiently emit light having desired color, there has been proposed a light emitting element containing: a first quantum dot monomolecular film located at the side of a hole transport layer; a second quantum dot monomolecular film located at the side of an electron transport layer; and an exciton forming layer located between the first and second monomolecular films (JP-A No. 2009-87754). However, this proposal does not specifically describe light emission efficiency or service life. There has also been proposed an element focusing on a protective material for quantum dots dispersed in a matrix material (JP-A No. 2009-99545). This proposal describes that considering a drop in light emission efficiency being caused by a capping agent (surfactant) present on the surfaces of quantum dots in the wet chemical process of producing quantum dots, an element exhibiting improved mobility of excitons to quantum dots and excellent light emission efficiency is provided by forming a state where a protective material is bonded via a coordination bond to the surfaces of quantum dots or a state where a protective material is present on the surfaces of quantum dots due to interaction (attractive force) between the surfaces of quantum dots and the protective material as well as satisfying a specific relationship among ionization potential (Ip), electron affinity (Ea) and band gap (Eg) of the protective material, Ip, Ea and Eg of the matrix material and Eg of the quantum dots. However, an element having satisfactorily high light emission efficiency cannot still be provided in this proposal.

SUMMARY OF THE INVENTION

The present invention has been made in view of the above-described status quo of the conventional technology, and aims to provide, as materials for organic EL elements, a novel carbazole derivative and a semiconductor nanocrystal that realize organic EL elements being particularly high in durability and light emission efficiency.

Means for solving the above existing problems are as follows.

A carbazole derivative of the present invention is a carbazole derivative represented by the following General Formula (1) where at least one aromatic ring has one to three substituents each represented by the following General Formula (2):

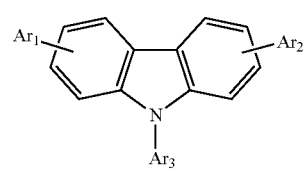

(1)

in General Formula (1), $Ar_1$ and $Ar_2$ each independently represent a substituted or unsubstituted aryl group which may form a ring with a benzene ring, a substituted or unsubstituted heterocyclic group, a substituted or unsubstituted arylsilyl group, or a hydrogen atom, and $Ar_3$ represents a substituted or unsubstituted aryl group,

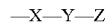 (2)

in General Formula (2), X represents a methylene group, a carbonyloxy group, an oxycarbonyl group, a carbonyl group, an oxygen atom or a sulfur atom, Y represents a substituted or unsubstituted alkylene group, and Z represents a carboxyl group, a hydroxyl group or a thiol group.

When an organic EL element is formed using the novel carbazole derivative of the present invention, it is possible to attain high durability and high light emission efficiency.

When a quantum dot-type organic EL element is formed using the semiconductor nanocrystal having the novel carbazole derivative of the present invention bonded via a coordination bond or intermolecular force, it is possible to attain high light emission efficiency.

DETAILED DESCRIPTION OF THE INVENTION

Figure 1:
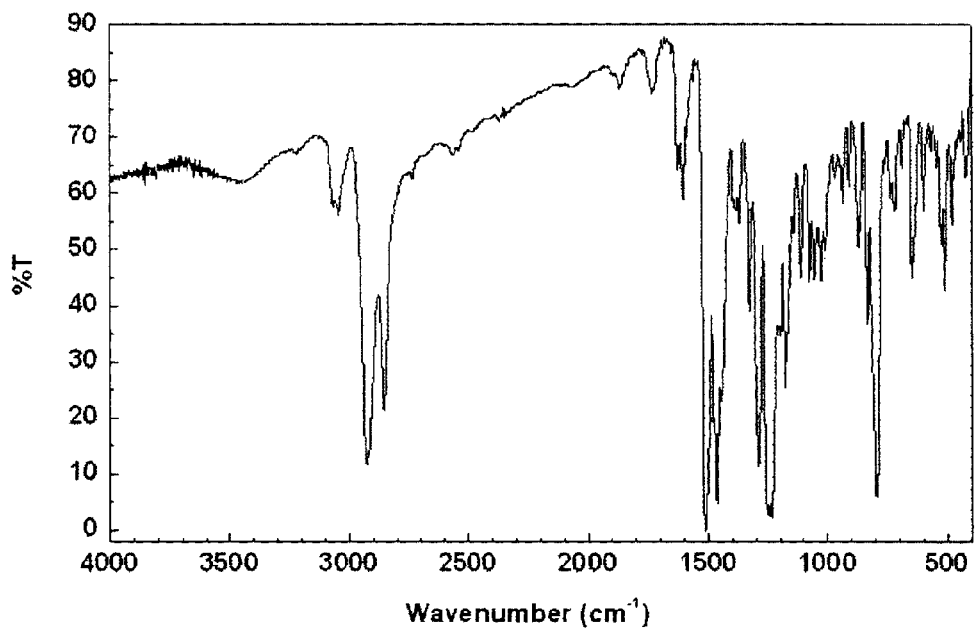
FIG. 1 is infrared absorption spectrum (KBr tablet method) of carbazole derivative 1 of the present invention.

A carbazole derivative of the present invention is a carbazole derivative represented by the following General Formula (1) where at least one aromatic ring has one to three substituents each represented by the following General Formula (2). When the aromatic ring of the compound represented by the following General Formula (1) has two or three substituents each represented by the following General Formula (2), the two or three substituents each represented by the following General Formula (2) may be identical or different.

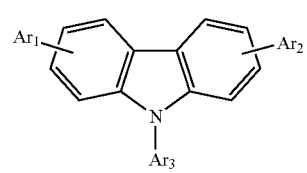

(1)

In General Formula (1), $Ar_1$ and $Ar_2$ each independently represent a substituted or unsubstituted aryl group which may form a ring with a benzene ring, a substituted or unsubstituted heterocyclic group, a substituted or unsubstituted arylsilyl group, or a hydrogen atom, and $Ar_3$ represents a substituted or unsubstituted aryl group.

—X—Y—Z (2)

In General Formula (2), X represents a methylene group, a carbonyloxy group, an oxycarbonyl group, a carbonyl group, an oxygen atom or a sulfur atom, Y represents a substituted or unsubstituted alkylene group, and Z represents a carboxyl group, a hydroxyl group or a thiol group.

The unsubstituted aryl group represented by $Ar_1$, $Ar_2$ or $Ar_3$ in General Formula (1) is not particularly limited and may be appropriately selected depending on the intended purpose. Examples thereof include phenyl, naphthyl, biphenyl, terphenyl, pyrenyl, fluorenyl, 9,9-dimethyl-2-fluorenyl, azulenyl, anthryl, triphenylenyl, chrysenyl, fluorenylidenephenyl and 5H-dibenzo[a,d]cycloheptenylidenephenyl.

The unsubstituted heterocyclic group represented by $Ar_1$ or $Ar_2$ in General Formula (1) is not particularly limited and may be appropriately selected depending on the intended purpose. Examples thereof include furyl, benzofuranyl, carbazolyl, pyridyl group, pyrrolidyl group, thiophenyl, methylthiophenyl and oxazolyl.

Notably, the aryl group and heterocyclic group may have as a substituent a C1-25 linear, branched or cyclic alkyl group such as methyl, ethyl, n-propyl, isopropyl, n-butyl, isobutyl, s-butyl, t-butyl, pentyl, hexyl, heptyl, octyl, nonyl, decyl, 3,7-dimethyloctyl, 2-ethylhexyl, trifluoromethyl, 2-cyanoethyl, benzyl, 4-chlorobenzyl, 4-methylbenzyl, cyclopentyl or cyclohexyl.

The substituent of the substituted aryl group represented by $Ar_1$, $Ar_2$ or $Ar_3$ is not particularly limited and may be appropriately selected depending on the intended purpose. Examples thereof include C1-25 substituted or unsubstituted linear, branched or cyclic alkoxy groups, halongen atoms such as fluorine, chlorine and bromine, and heterocyclic groups such as cyano, triphenylsilyl, furyl, benzofuranyl, carbazolyl, pyridyl, pyrrolidyl, thiophenyl, methylthiophenyl and oxazolyl.

Here, the substituent of the substituted alkoxy group is not particularly limited and may be appropriately selected depending on the intended purpose. Examples thereof include a fluorine atom, a cyano group and a substituted or unsubstituted phenyl group. The substituent of the substituted phenyl group is not particularly limited and may be appropriately selected depending on the intended purpose. Examples thereof include halogen atoms such as fluorine, chlorine and bromine, and linear or cyclic alkyl groups.

Examples of the substituted or unsubstituted alkoxy group include methoxy, ethoxy, n-propoxy, isopropoxy, n-butoxy, isobutoxy, s-butoxy, t-butoxy, pentyloxy, hexyloxy, heptyloxy, octyloxy, nonyloxy, decyloxy, 3,7-dimethyloctyloxy, 2-ethylhexyloxy, trifluoromethoxy, 2-cyanoethoxy, benzyloxy, 4-chlorobenzyloxy, 4-methylbenzyloxy, cyclopentyloxy and cyclohexyloxy.

The number of carbon atoms contained in the aryl group is preferably 6 to 30, and the number of carbon atoms contained in the heterocyclic group is preferably 4 to 28.

Examples of the substituted or unsubstituted arylsilyl represented by Ar$_1$, Ar$_2$ or Ar$_3$ include dimethylphenylsilyl, methyldiphenylsilyl, triphenylsilyl, tri(2-biphenyl)silyl, tri(o-toluoyl)silyl, 1,1,2,2,2-pentaphenyldisilyl, diphenyl(diphenylmethyl)silyl, tris(1-naphthypsilyl, tris(2-methoxyphenyl)silyl, and 4-methyl-1,1,2,2,3,3,4,4-octaphenyltetrasilyl.

When A$_1$ and/or Ar$_2$ is an aryl group which forms a ring with a benzene ring, examples of the compound represented by General Formula (1) include benzocarbazole derivatives and dibenzocarbazole derivatives.

The number of carbon atoms contained in the unsubstituted alkylene group represented by Y in General Formula (2) is preferably 1 to 25. The unsubstituted alkylene group is not particularly limited and may be appropriately selected depending on the intended purpose. Examples thereof include methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, haptadecamethylene, octadecamethylene, nonadecamethylene, icosamethylene, henicosamethylene, docosamethylene, tricosamethylene, tetracosamethylene and pentacosamethylene.

The substituent of the substituted alkylene group represented by Y is not particularly limited and may be appropriately selected depending on the intended purpose. Examples thereof include halogen atoms such as fluorine, chlorine and bromine, and C1-24 linear, branched or cyclic alkyl groups.

In the present invention, the carbazole derivative is not particularly limited and may be appropriately selected depending on the intended purpose, and examples thereof include the following compounds. Notably, X, Y and Z in these compounds have the same meanings as defined in General Formula (2). Me denotes a methyl group.

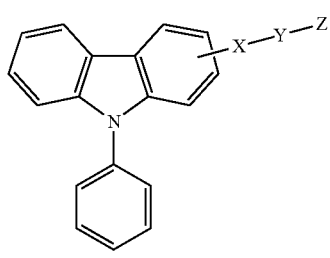

No. 1

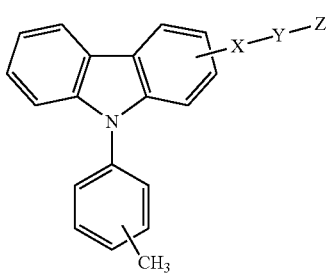

No. 2

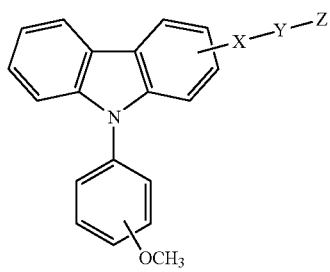

No. 3

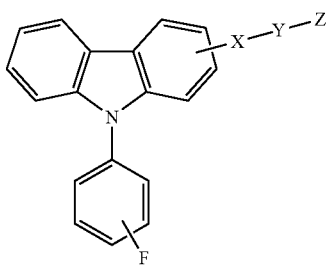

No. 4

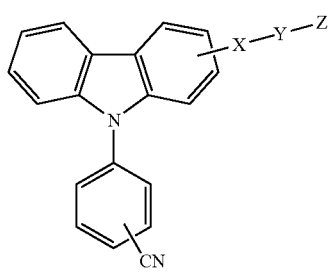

No. 5

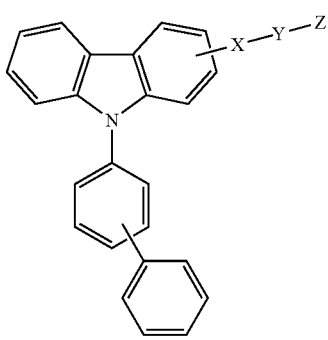

No. 6

-continued
No. 7
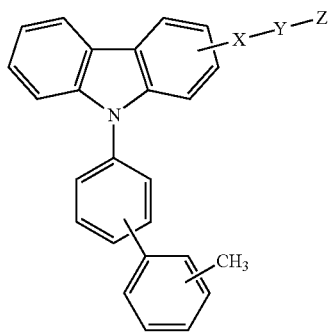
No. 8
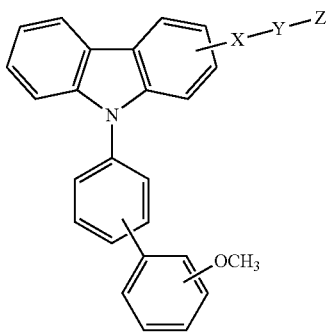
No. 9
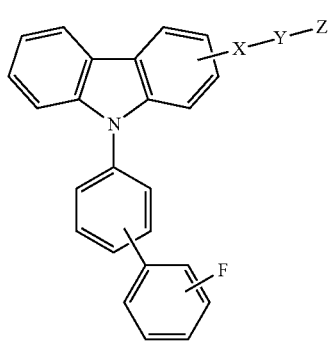
No 10
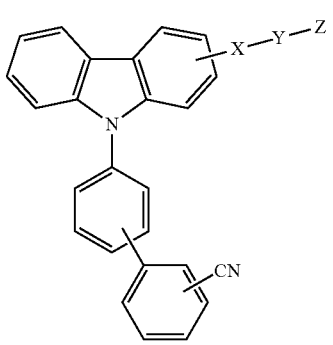
No 11
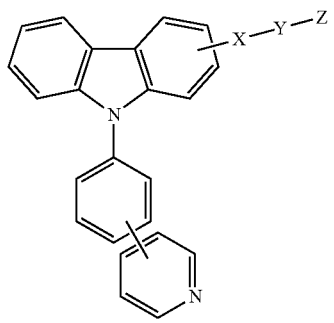
No. 12
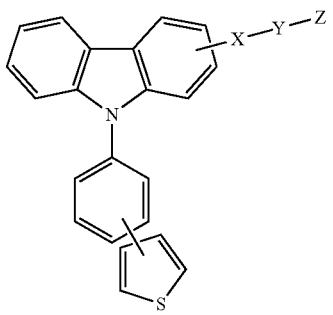
No. 13
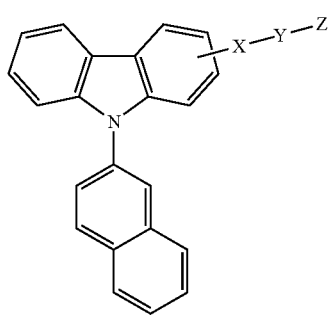
No. 14
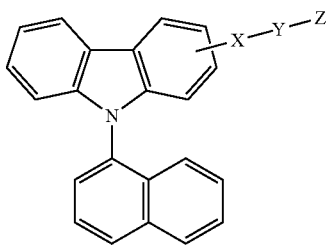
No. 15
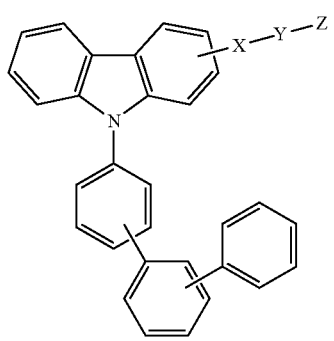
No. 16
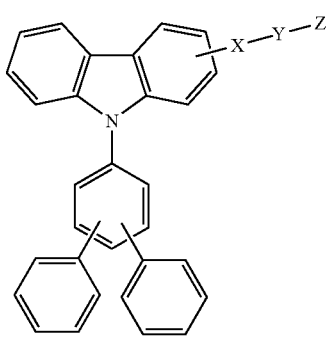

-continued
No. 17
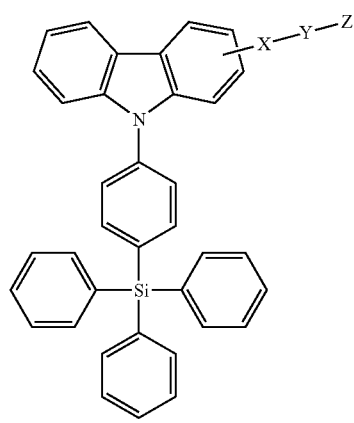
No. 18
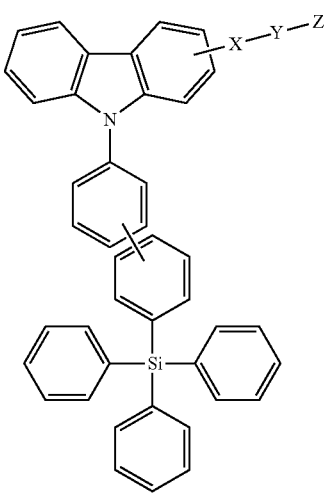
No. 19
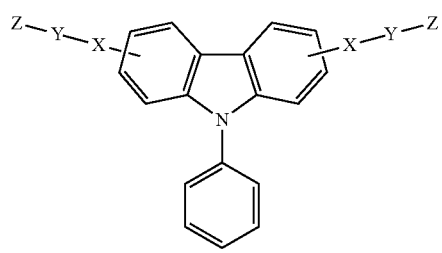
No. 20
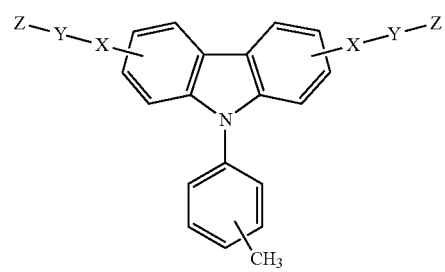
No. 21
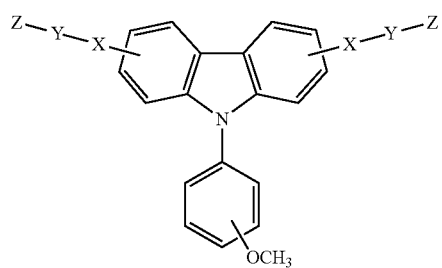
No. 22
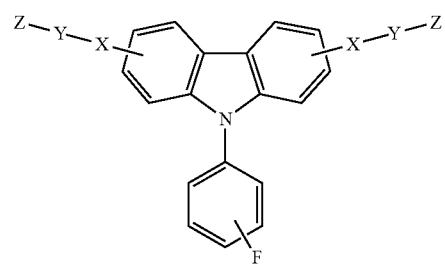
No. 23
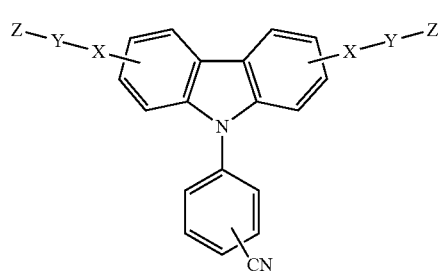
No. 24
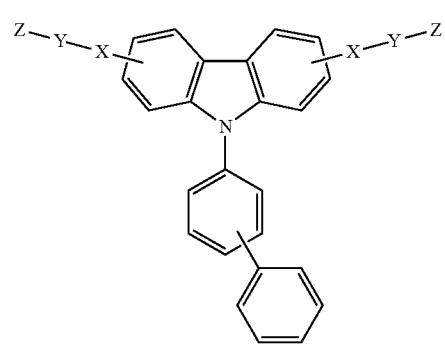

-continued
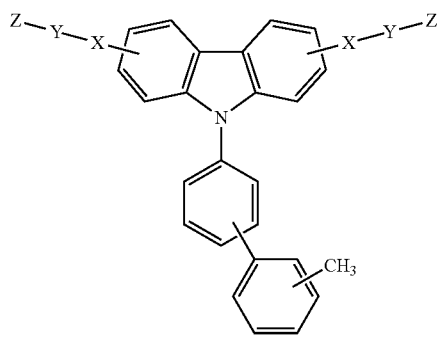
No. 25
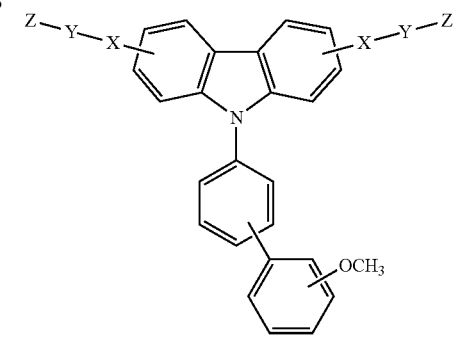
No. 26
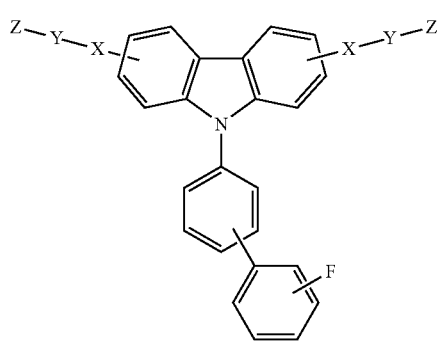
No. 27
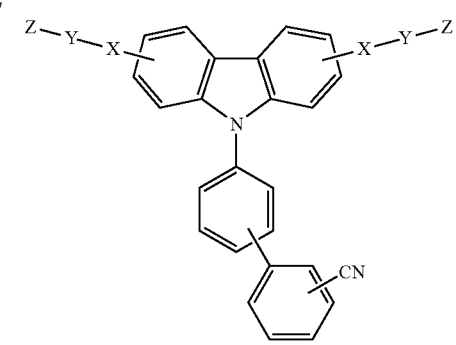
No. 28
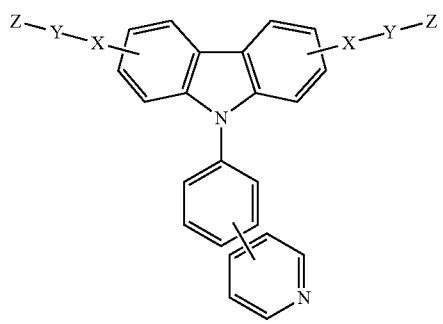
No. 29
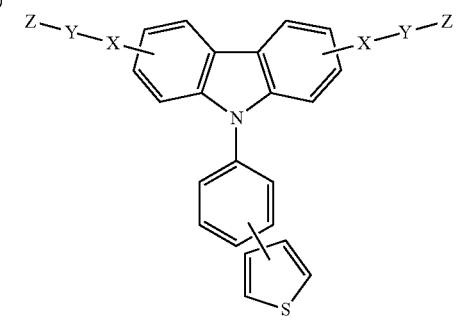
No. 30
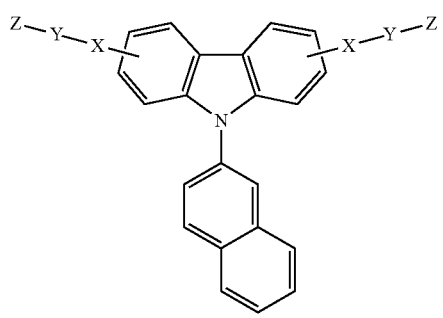
No. 31
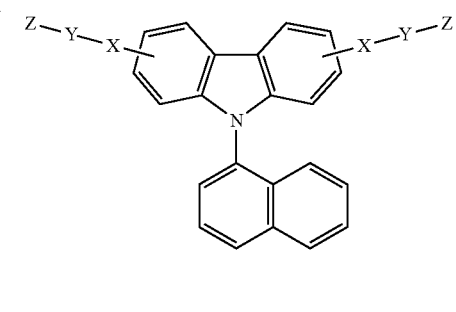
No. 32
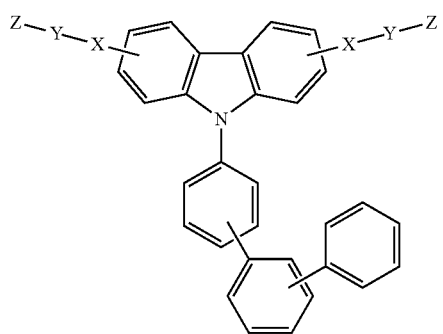
No. 33
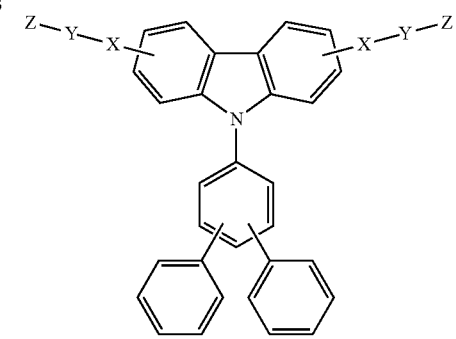
No. 34

-continued
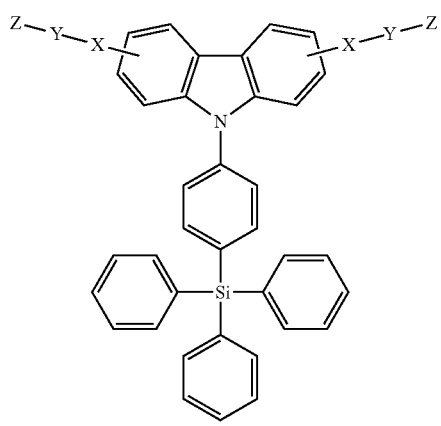
No. 35
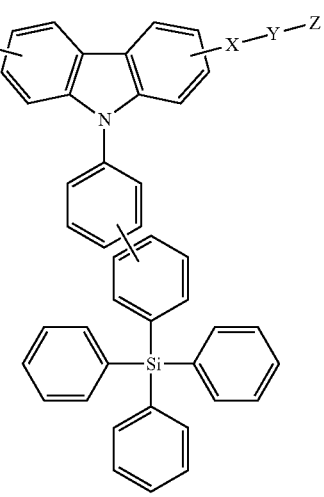
No. 36
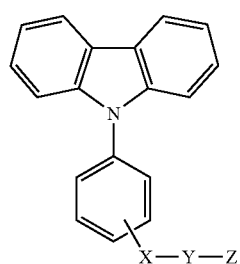
No. 37
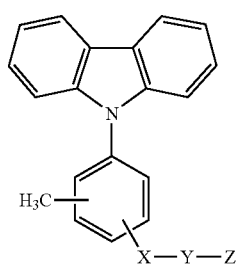
No. 38
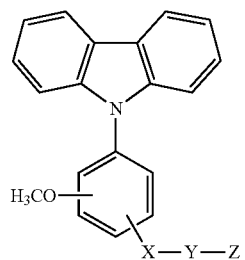
No. 39
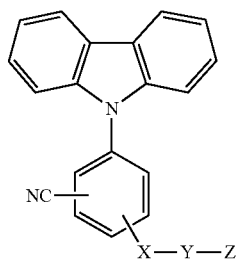
No. 40
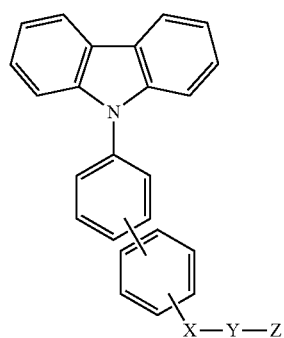
No. 41
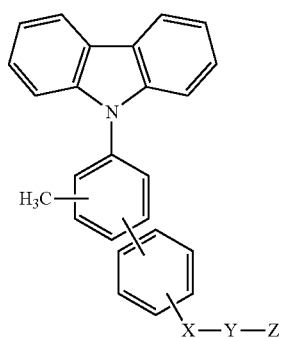
No. 42

-continued
No. 43
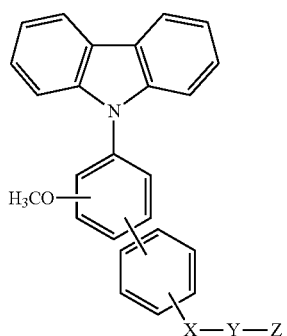
No. 44
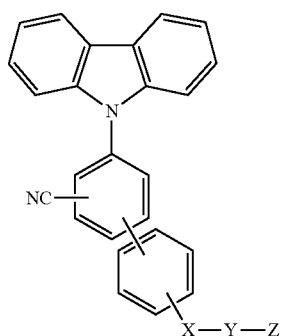
No. 45
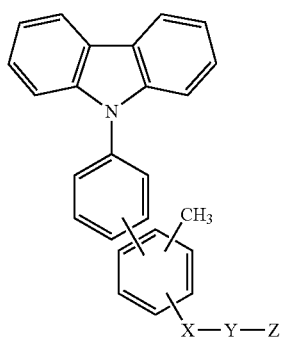
No. 46
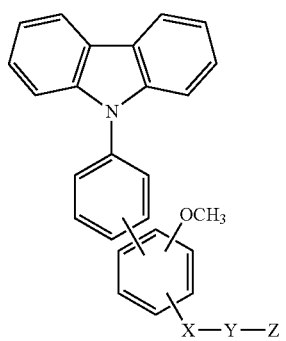
No. 47
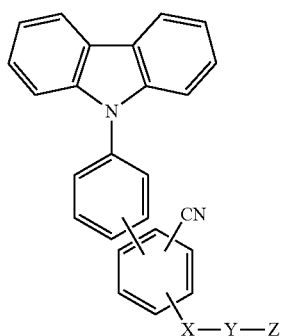
No. 48
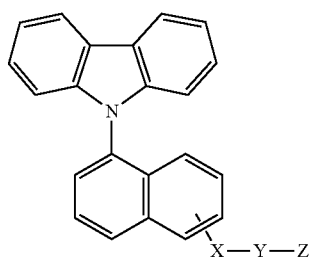
No. 49
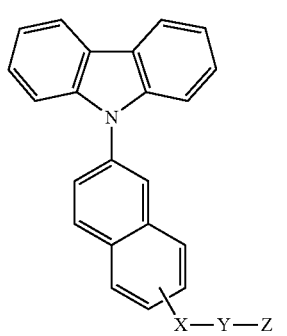
No. 50
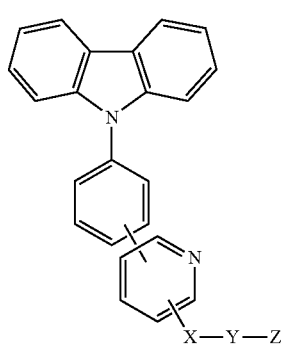

-continued
| No. 51 | No. 52 |
|---|---|
| 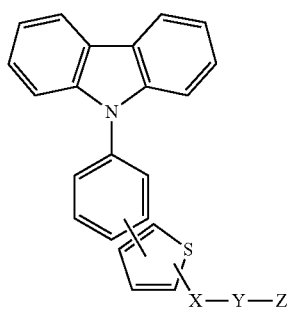 | 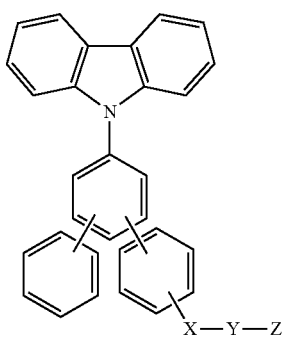 |
| No. 53 | No. 54 |
|---|---|
| 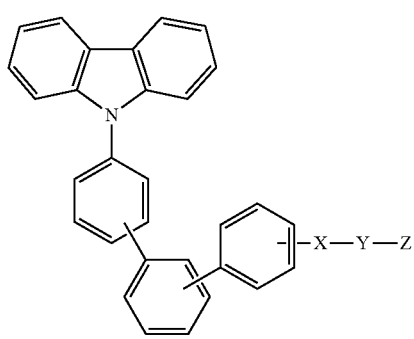 | 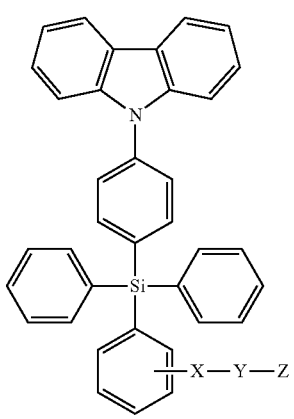 |
| No. 55 | No. 56 |
|---|---|
| 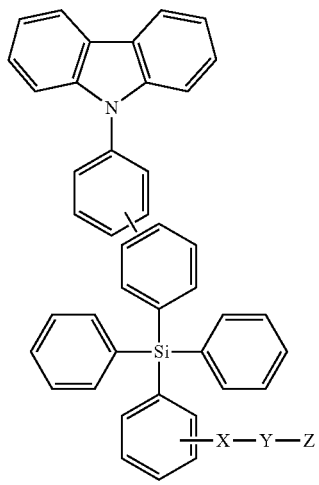 | 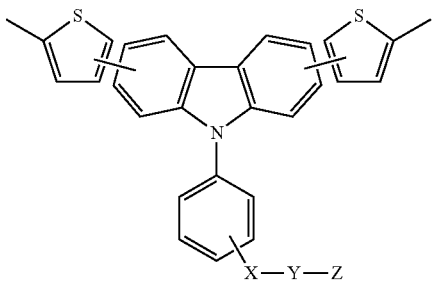 |
| No. 57 | No. 58 |
|---|---|
| 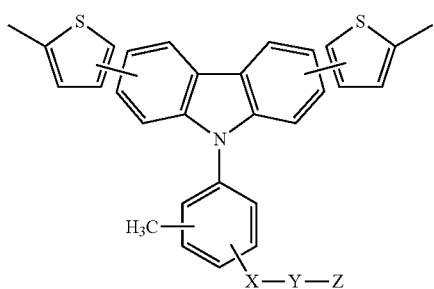 | 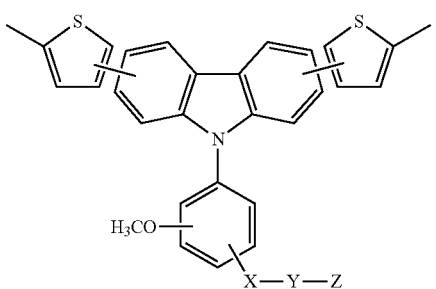 |

-continued
No. 59
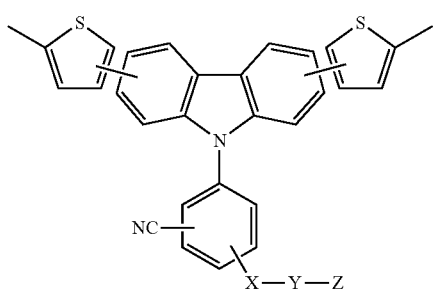
No. 60
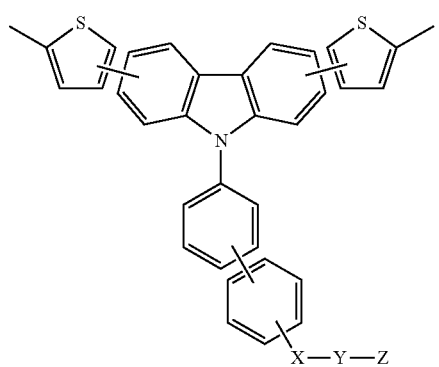
No. 61
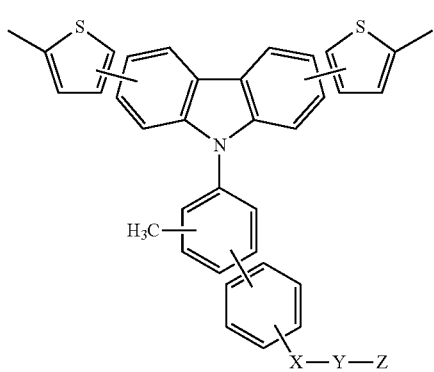
No. 62
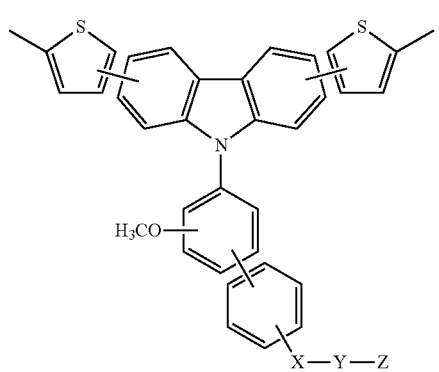
No. 63
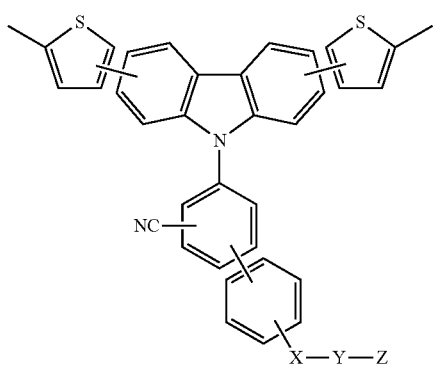
No. 64
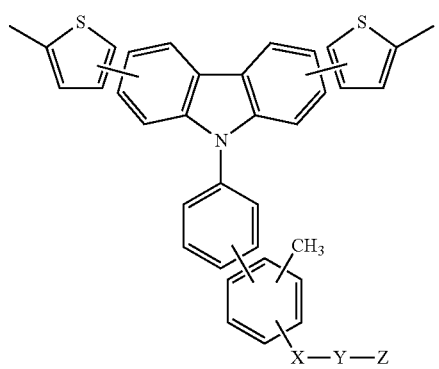
No. 65
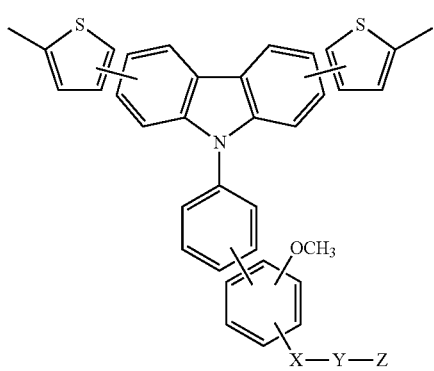
No. 66
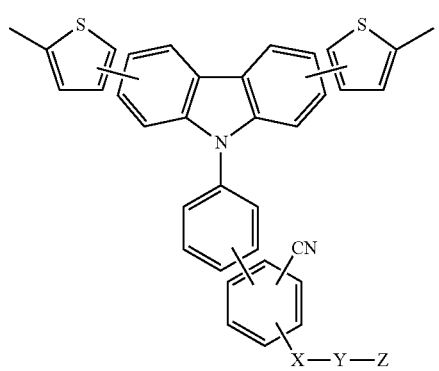

-continued
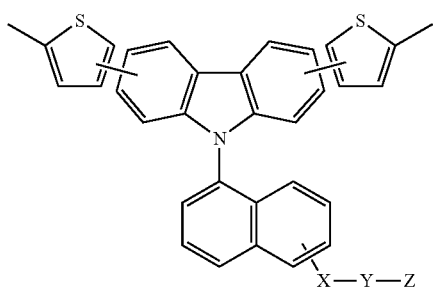
No. 67
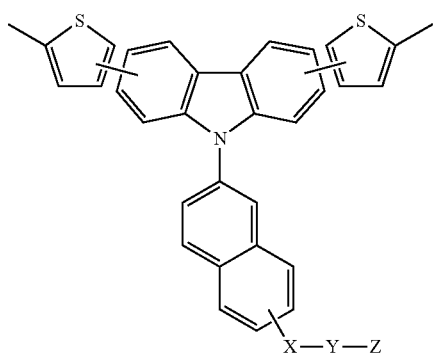
No. 68
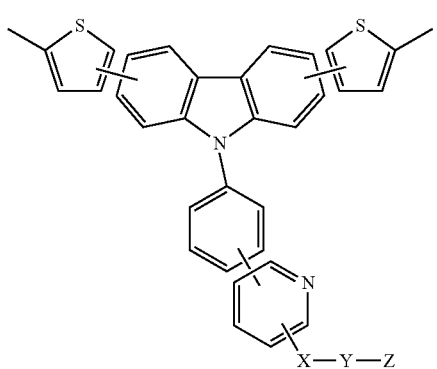
No. 69
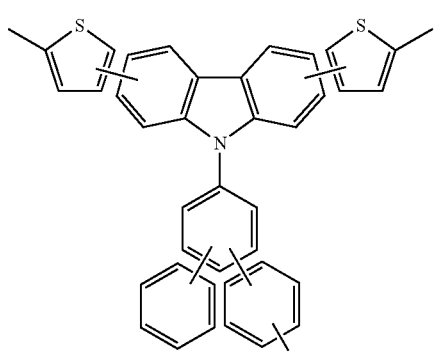
No. 70
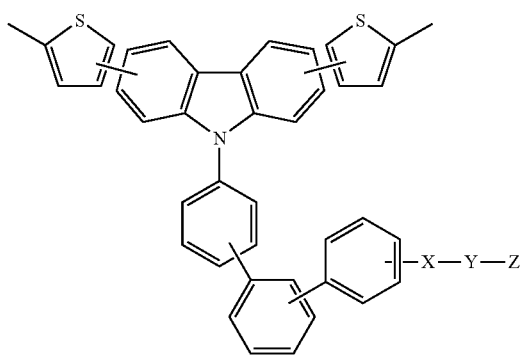
No. 71
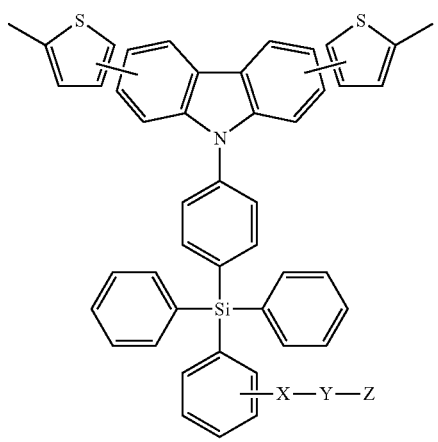
No. 72
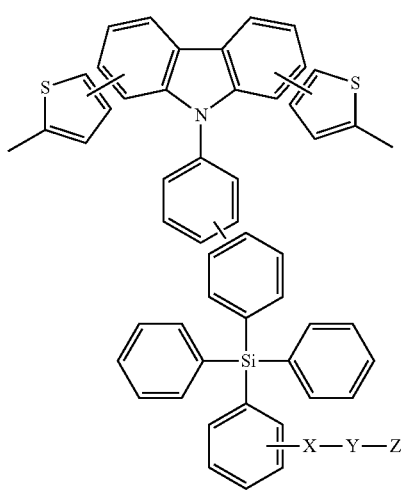
No. 73
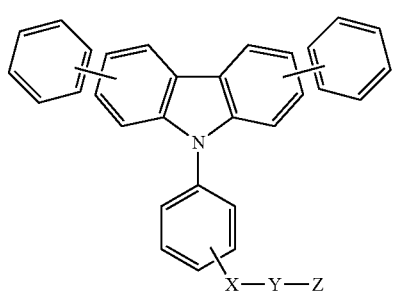
No. 74

-continued
No. 75
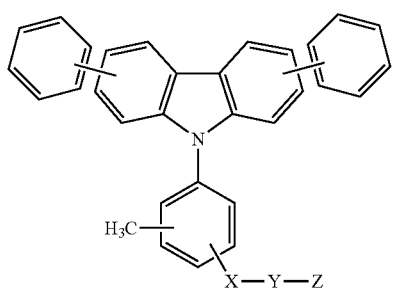
No. 76
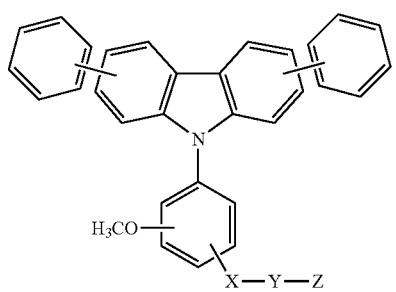
No. 77
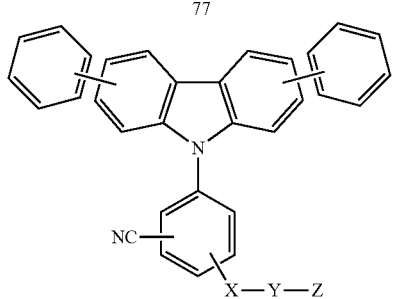
No. 78
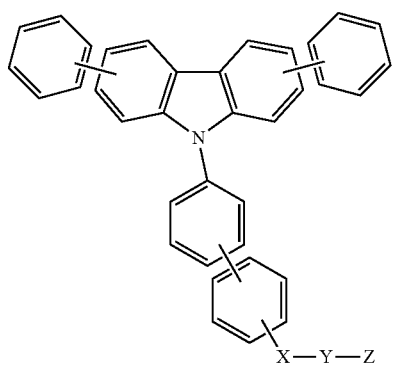
No. 79
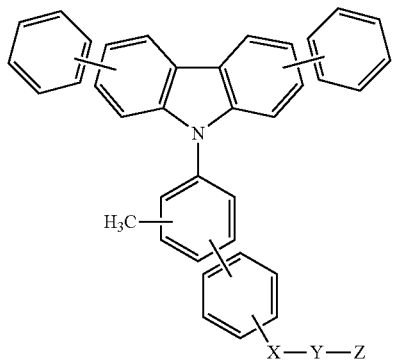
No. 80
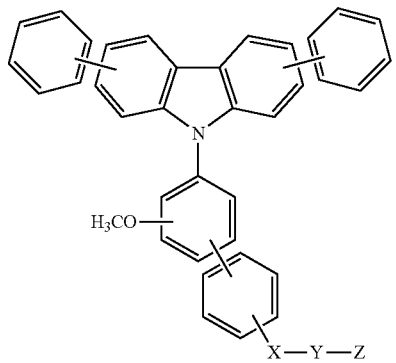
No. 81
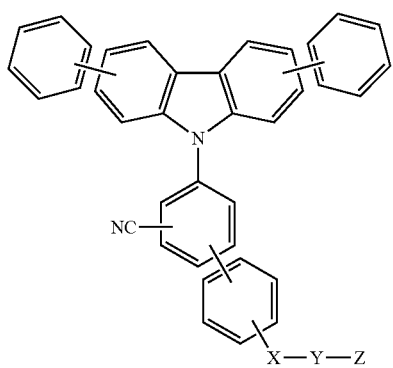
No. 82
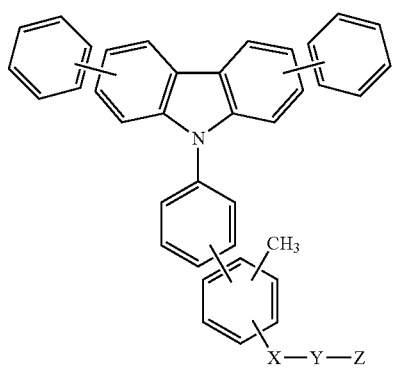

-continued
No. 83
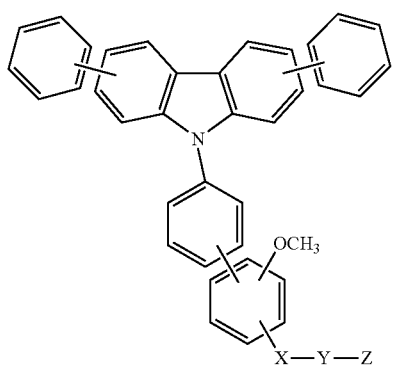
No. 84
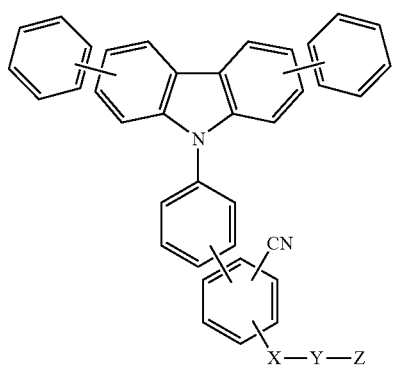
No. 85
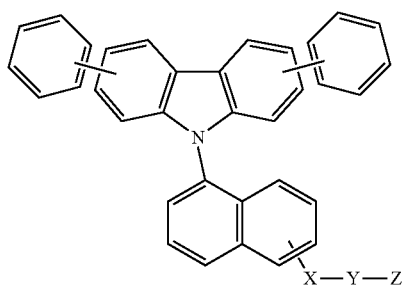
No. 86
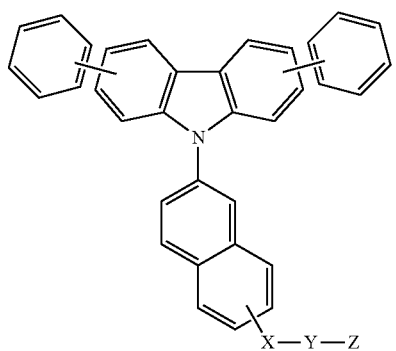
No. 87
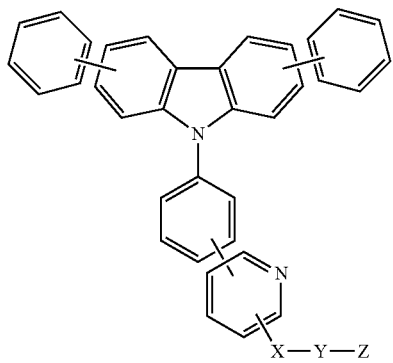
No. 88
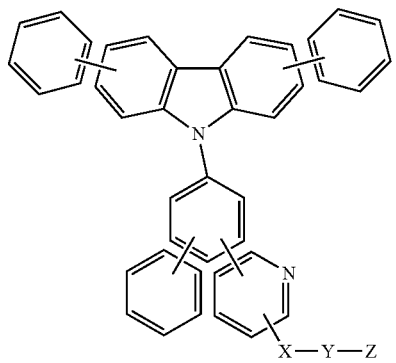
No. 89
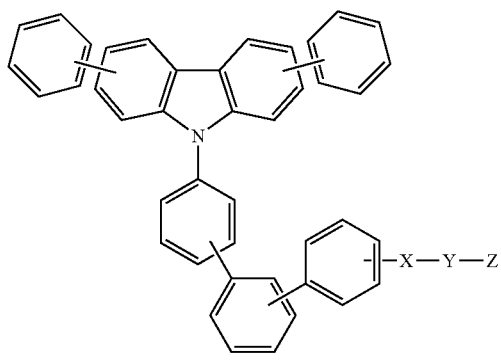
No. 90
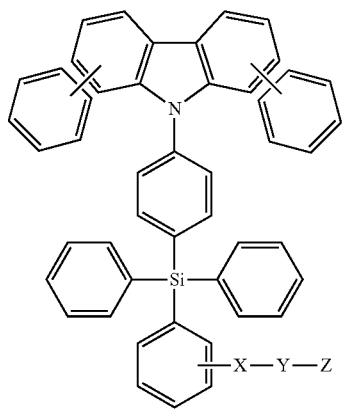

-continued
No. 91
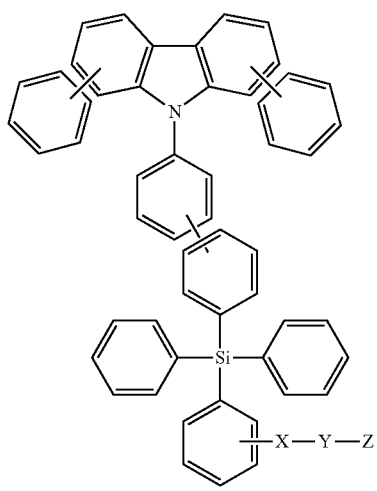
No. 92
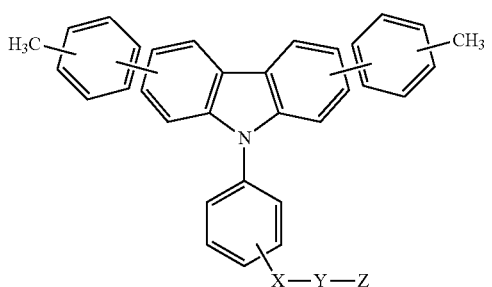
No. 93
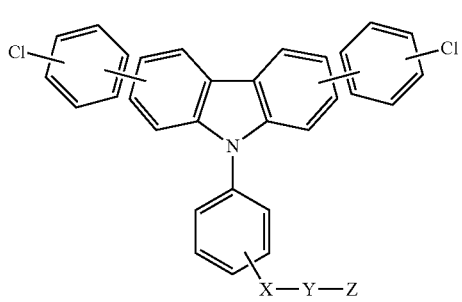
No. 94
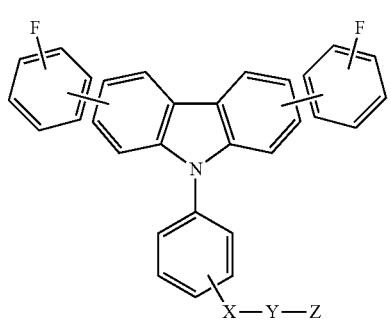
No. 95
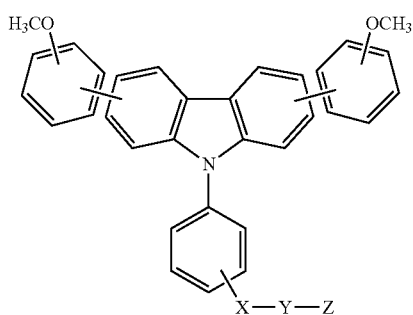
No. 96
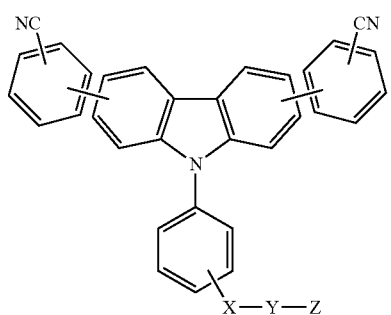
No. 97
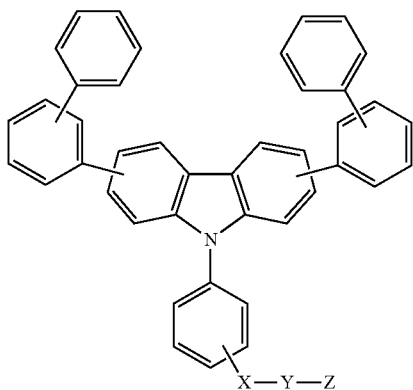
No. 98
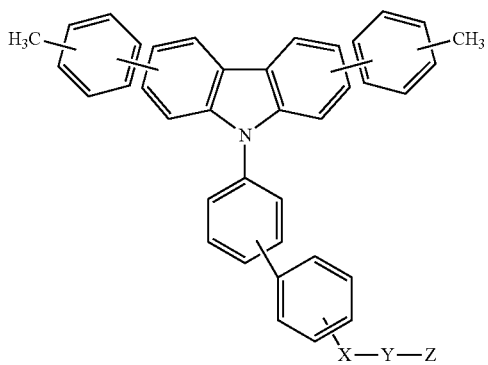

-continued
No. 99
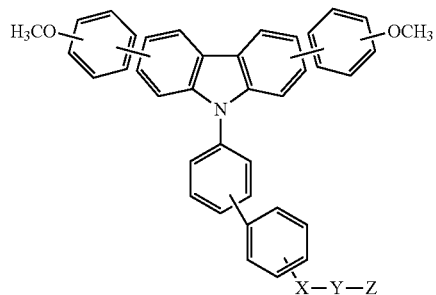
No. 100
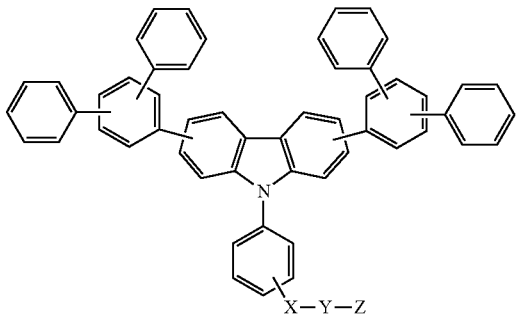
No. 101
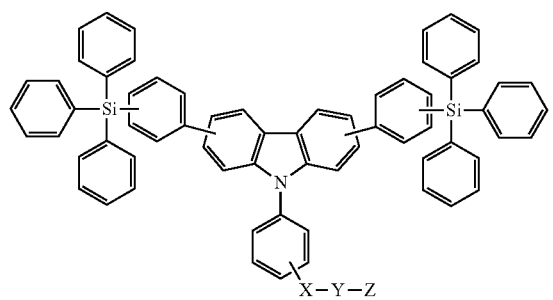
No. 102
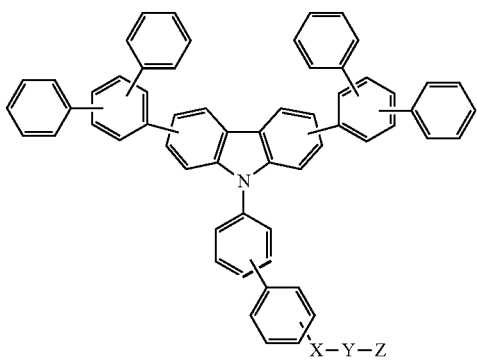
No. 103
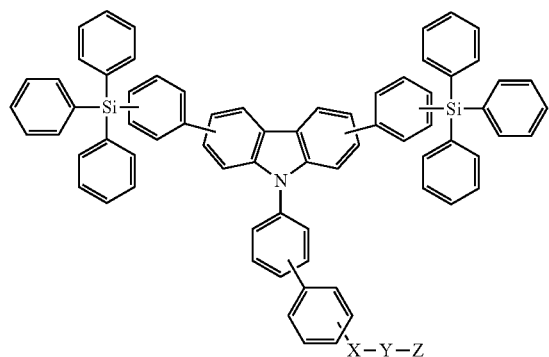
No. 104
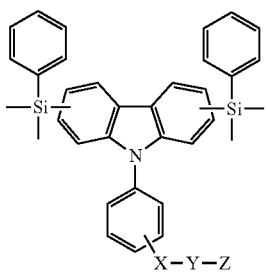
No. 105
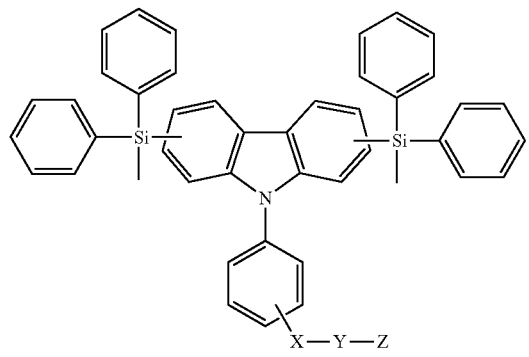
No. 106
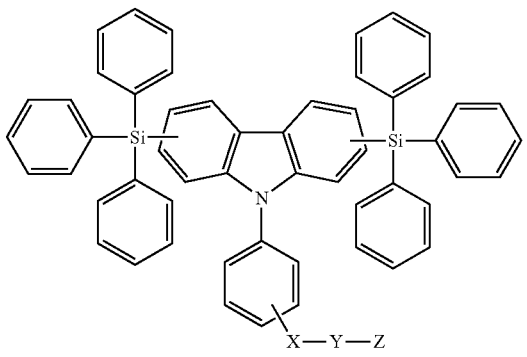

-continued
No. 107
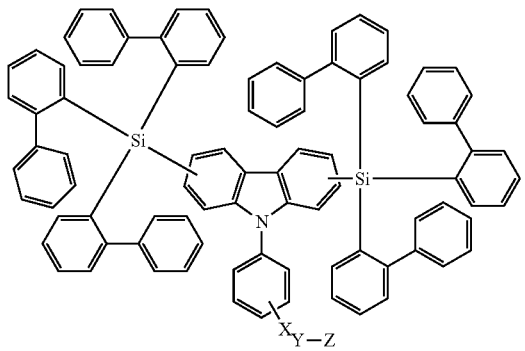
No. 108
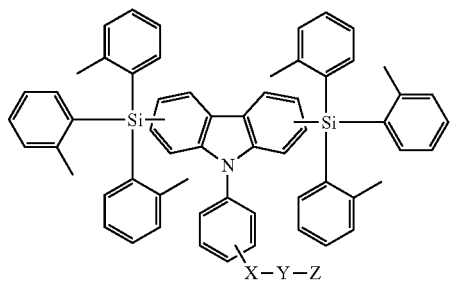
No. 109
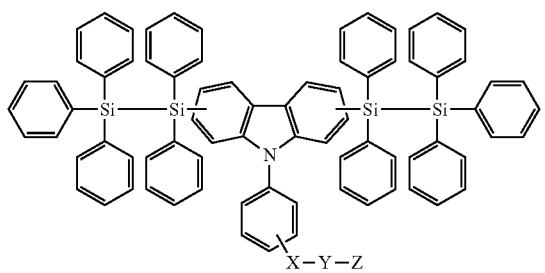
No. 110
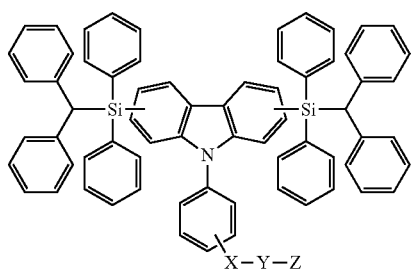
No. 111
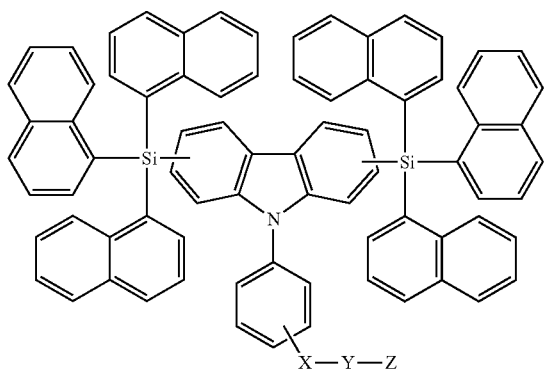
No. 112
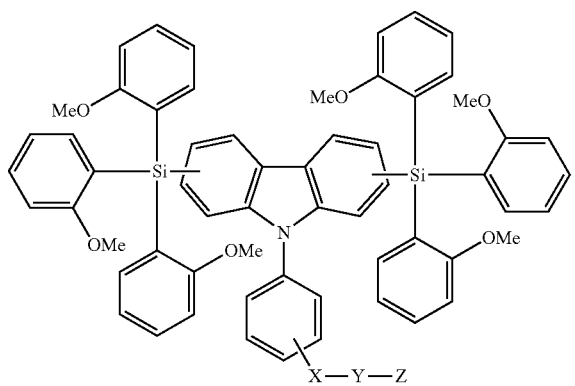
No. 113
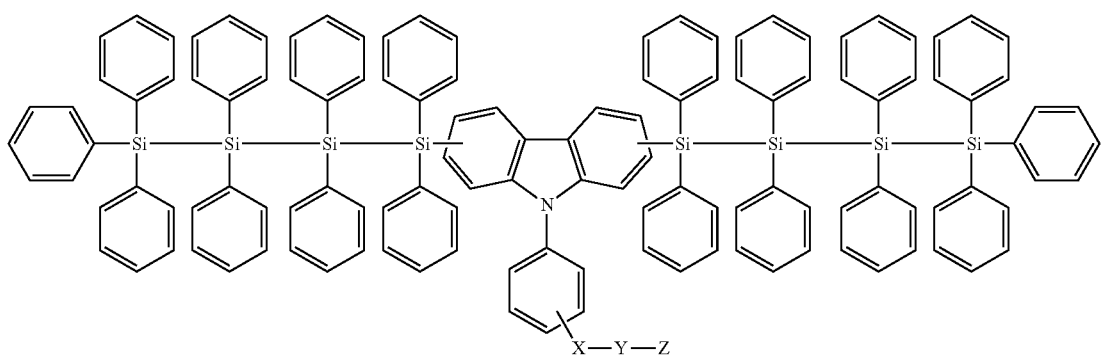

-continued
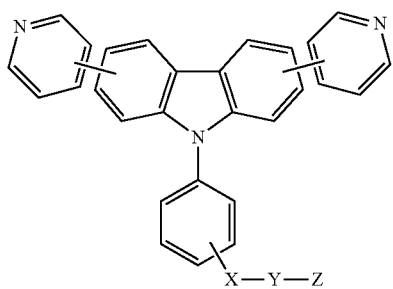
No. 114
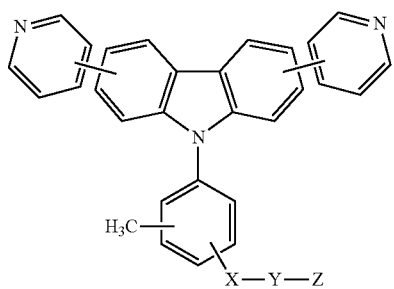
No. 115
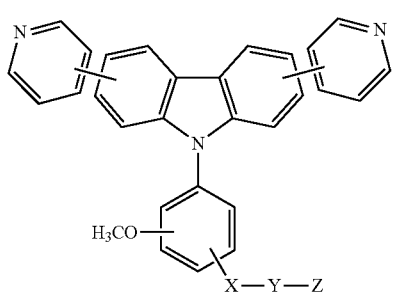
No. 116
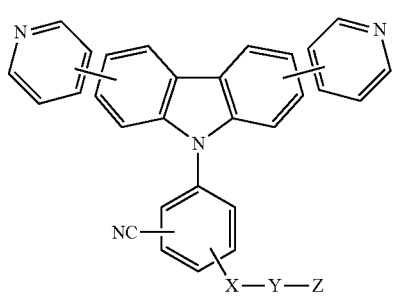
No. 117
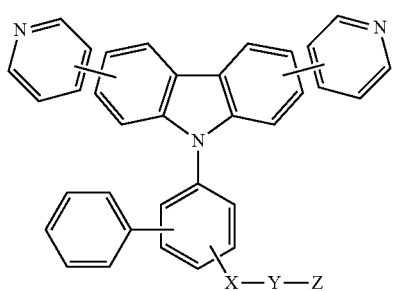
No. 118
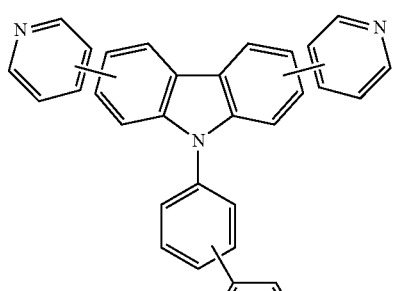
No. 119
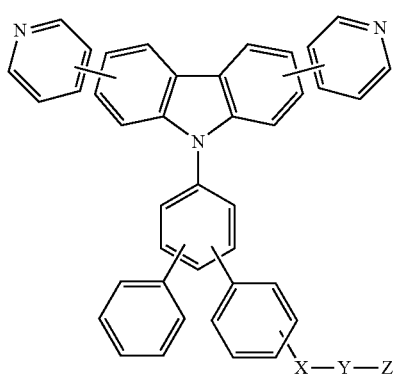
No. 120
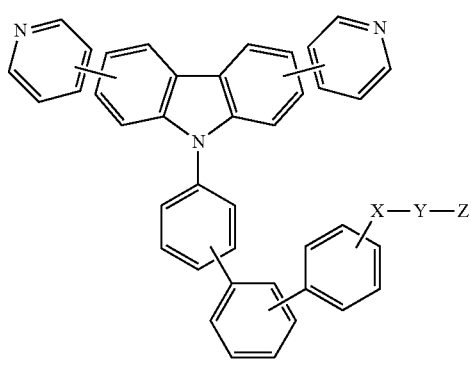
No. 121

No. 122 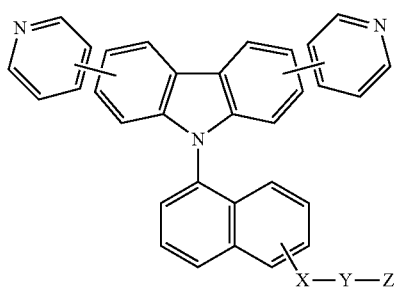
No. 123 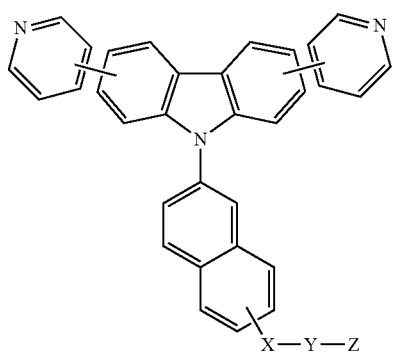
No. 124 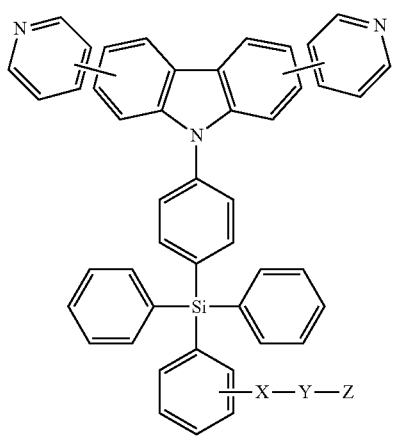
No. 125 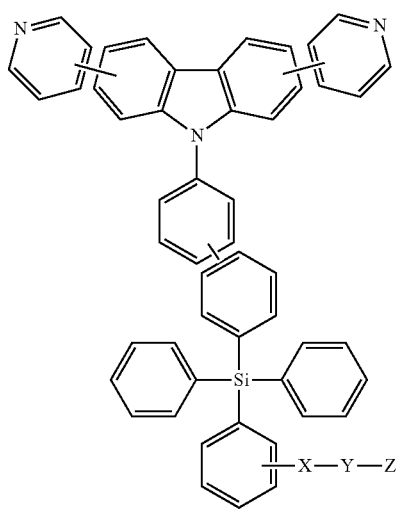
No. 126 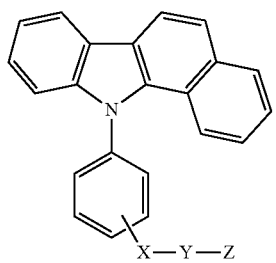
No. 127 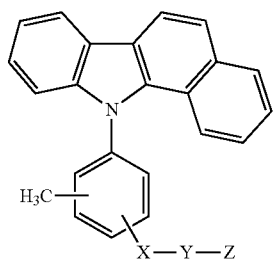
No. 128 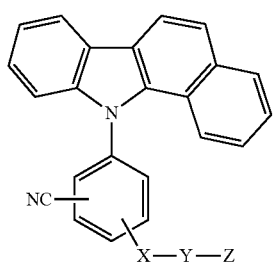
No. 129 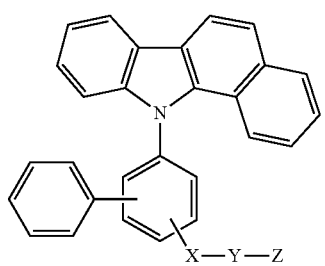

-continued
No. 130
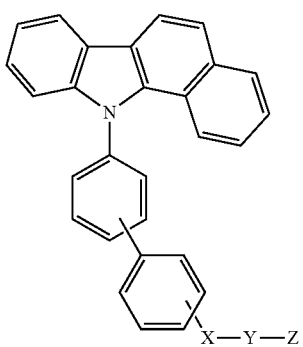
No. 131
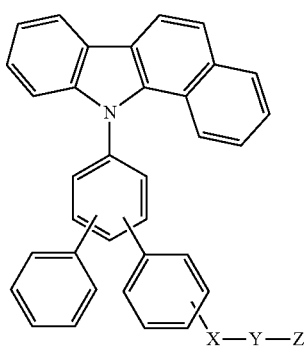
No. 132
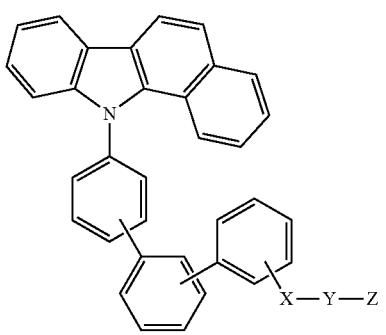
No. 133
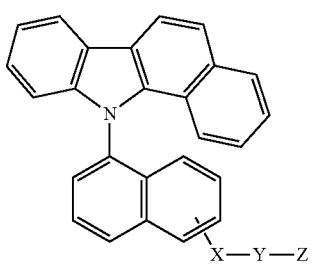
No. 134
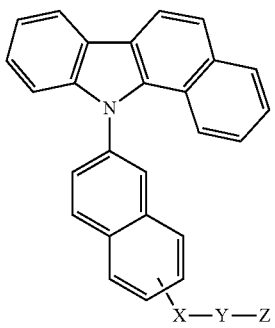
No. 135
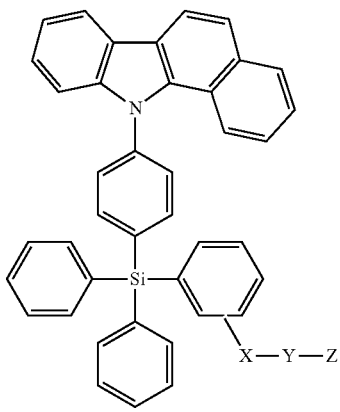
No. 136
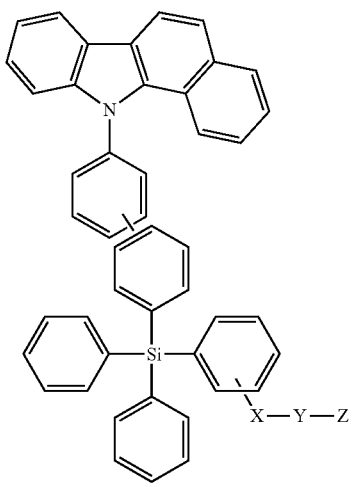
No. 137
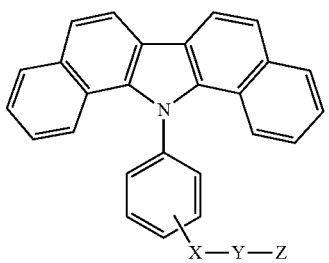

-continued
No. 138
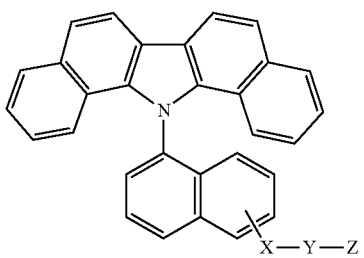
No. 139
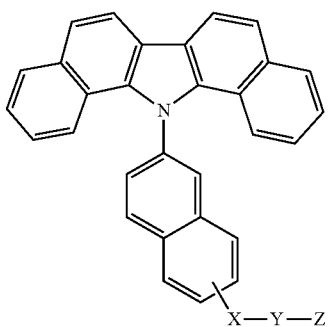
No. 140
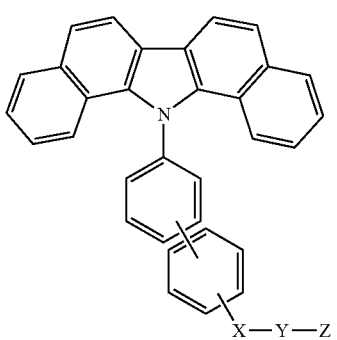
No. 141
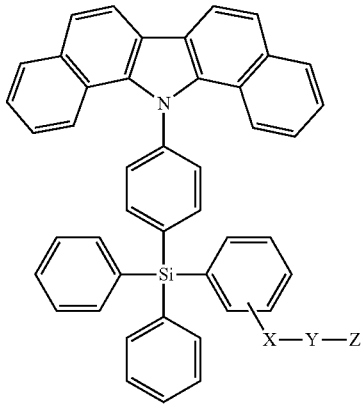
No. 142
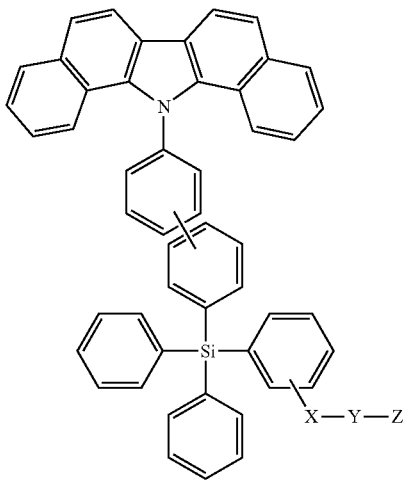
No. 143
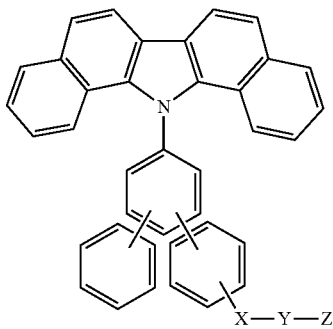
No. 144
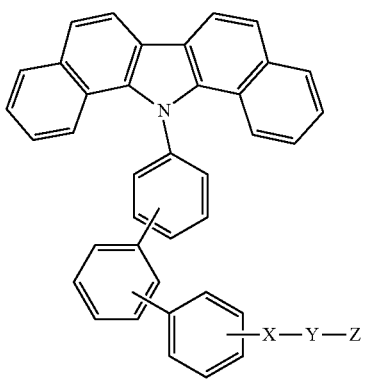

The group represented by General Formula (2) is not particularly limited and may be appropriately selected depending on the intended purpose, and examples thereof include the following groups.

| | |
|---|---|
| 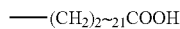 | No. 1 |
| 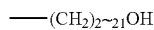 | No. 2 |
| 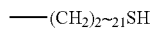 | No. 3 |
| 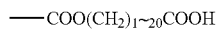 | No. 4 |
|  | No. 5 |
|  | No. 6 |
| 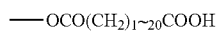 | No. 7 |
|  | No. 8 |
|  | No. 9 |
| 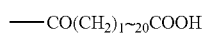 | No. 10 |
|  | No. 11 |
| 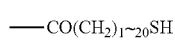 | No. 12 |
|  | No. 13 |
|  | No. 14 |
|  | No. 15 |
|  | No. 16 |
|  | No. 17 |
|  | No. 18 |
| 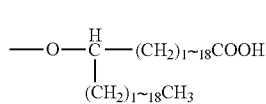 | No. 19 |
| 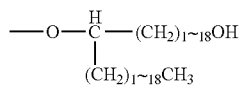 | No. 20 |
| 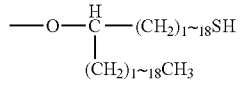 | No. 21 |
| 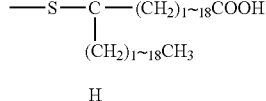 | No. 22 |
| 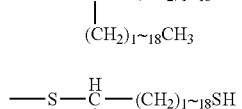 | No. 23 |
| 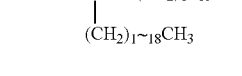 | No. 24 |

In the present invention, the carbazole derivative is preferably a compound represented by the following General Formula (3) or (6). Here, $Ar_4$ represents an arylene group derived from $Ar_3$.

In the following General Formula (3), preferably, $Ar_1$ and $Ar_2$ each independently represent a group represented by the following General Formula (4). The compound represented by the following General Formula (3) is preferably a benzocarbazole derivative represented by the following General Formula (5).

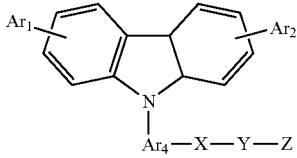

(3)

In General Formula (3), $Ar_4$ represents a substituted or unsubstituted arylene group, and $Ar_1$, $Ar_2$, X, Y and Z have the same meanings as defined above.

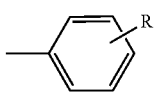

(4)

In General Formula (4), R represents a hydrogen atom, a substituted or unsubstituted alkyl group, a substituted or unsubstituted alkoxy group, a halogen atom, or a substituted or unsubstituted aryl group.

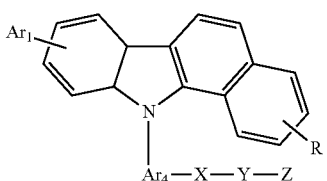

(5)

In General Formula (5), R represents a hydrogen atom, a substituted or unsubstituted alkyl group, a substituted or unsubstituted alkoxy group, a halogen atom, or a substituted or unsubstituted aryl group, and $Ar_1$, $Ar_4$, X, Y and Z have the same meanings as defined above.

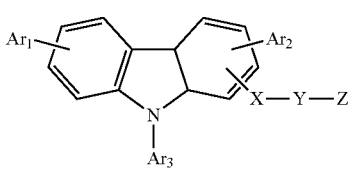

(6)

In General Formula (6), $Ar_1$, $Ar_2$, $Ar_3$, X, Y and Z have the same meanings as defined above.

In General Formulas (4) and (5), the unsubstituted alkyl group represented by R is preferably a C1-25 linear, branched or cyclic alkyl group. The unsubstituted alkoxy group represented by R is preferably a C1-25 linear, branched or cyclic alkoxy group. Here, the substituent of the substituted alkyl group or alkoxy group is not particularly limited and may be appropriately selected depending on the intended purpose. Examples thereof include a fluorine atom, a cyano group, and a substituted or unsubstituted phenyl group. The substituent of the substituted phenyl is not particularly limited and may be appropriately selected depending on the intended purpose. Examples thereof include halogen atoms such as fluorine, chlorine and bromine, and linear or cyclic alkyl groups.

Examples of the substituted or unsubstituted alkyl group include methyl, ethyl, n-propyl, isopropyl, n-butyl, isobutyl, s-butyl, t-butyl, pentyl, hexyl, heptyl, octyl, nonyl, decyl, 3,7-dimethyloctyl, 2-ethylhexyl, trifluoromethyl, 2-cyanoethyl, benzyl, 4-chlorobenzyl, 4-methylbenzyl, cyclopentyl and cyclohexyl.

Examples of the substituted or unsubstituted alkoxy group include methoxy, ethoxy, n-propoxy, isopropoxy, n-butoxy, isobutoxy, s-butoxy, t-butoxy, pentyloxy, hexyloxy, heptyloxy, octyloxy, nonyloxy, decyloxy, 3,7-dimethyloctyloxy, 2-ethylhexyloxy, trifluoromethoxy, 2-cyanoethoxy, benzyloxy, 4-chlorobenzyloxy, 4-methylbenzyloxy, cyclopentyloxy and cyclohexyloxy.

The halogen atom represented by R is not particularly limited and may be appropriately selected depending on the intended purpose. Examples thereof include fluorine, chlorine and bromine.

The aryl group represented by R is the same as the above aryl group represented by $Ar_1$, $Ar_2$ or $Ar_3$.

Synthesis Method of the Compound Represented by General Formula (3)

Synthesis Example 1 of the Compound Represented by General Formula (3)

The compound represented by General Formula (3) can be synthesized in the following manner.

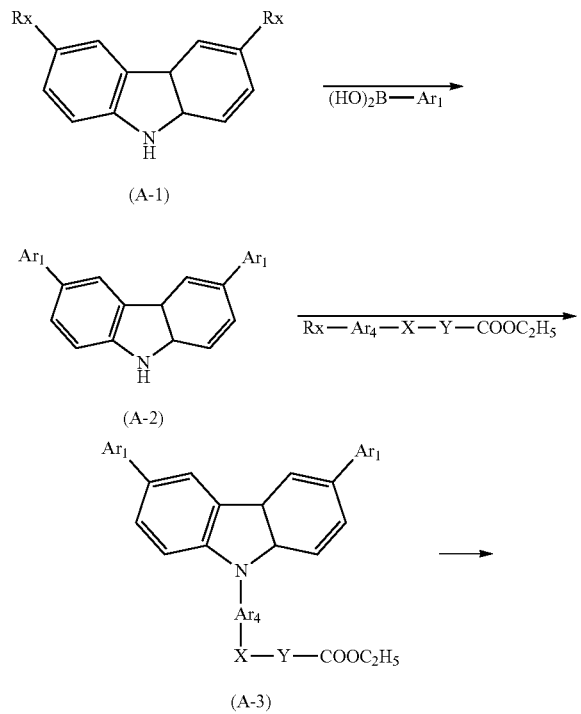

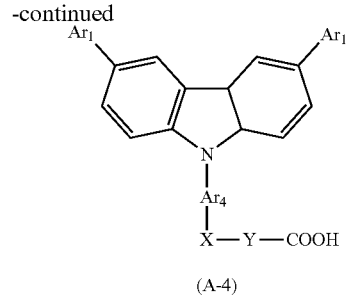

In the above reaction scheme, Rx represents a halogen atom, and $Ar_1$, $Ar_4$, X, Y and Z have the same meaning as defined above.

First, a palladium catalyst is used to perform Suzuki-Miyaura cross coupling reaction between organic halogen compound (A-1) and arylboronic acid $Ar_1\text{-B(OH)}_2$, to thereby produce carbazole derivative (A-2).

The palladium catalyst is not particularly limited and may be appropriately selected depending on the intended purpose. Examples thereof include $Pd(PPh_3)_4$, $PdCl_2(PPh_3)_2$, $Pd(OAc)_2$ and $PdCl_2$, with $Pd(PPh_3)_4$ is most commonly used.

The arylboronic acid may be changed to an arylboronic acid ester which is thermally stable, is easily handled in air, and is synthesized between bis(pinacolato)diboron and an aryl halide. In terms of reactivity, Rx of the organic halogen compound (A-1) is preferably an iodine atom or a bromine atom.

This reaction requires a base, which is preferably a relatively weak base such as $Na_2CO_3$ or $NaHCO_3$. When unfavorable phenomena such as steric hindrance occur, a strong base such as $Ba(OH)_2$ or $K_3PO_4$ is effectively used. Other usable bases include sodium hydroxide, potassium hydroxide, metal alkoxides such as potassium t-butoxyde, sodium t-butoxide, lithium t-butoxide, potassium 2-methyl-2-butoxide, sodium 2-methyl-2-butoxide, sodium methoxide, sodium ethoxide, potassium ethoxide, and potassium methoxide. In addition, the base may be an organic base such as triethylamine.

The reaction solvent usable include: alcohol and ether solvents such as methanol, ethanol, isopropanol, butanol, 2-methoxyethanol, 1,2-dimethoxyethanol and bis(2-methoxyethyl)ether; cyclic ether solvents such as dioxan and tetrahydrofuran; benzene, toluene, xylene, dimethylsulfoxide, N,N-dimethylformamide, N-methylpyrrolidone and 1,3-dimethyl-2-imidazolidinone.

Next, a palladium catalyst and a phosphine ligand are used to perform Buchwald-Hartwig amination reaction between carbazole derivative (A-2) and aryl halide Rx-$Ar_4$—X—Y—$COOC_2H_5$, to thereby produce carbazole derivative (A-3).

The palladium catalyst is not particularly limited as described above, and examples thereof include $Pd_2(dba)_3$ and $Pd(OAc)_2$.

The phosphine ligand is not particularly limited and may be appropriately selected depending on the intended purpose. Examples thereof include 2,2'-bis(diphenylphosphino)-1,1'-binaphthyl, pentaphenyl(di-t-butylphosphino)ferrocene, bis(1-adamantyl)-n-butylphosphine, bis(1-adamantyl)-n-butylphosphonium iodide, and bis(1-adamantyl)benzylphosphine.

In terms of reactivity, Rx of the aryl halide is preferably a bromine atom or a chlorine atom.

This reaction requires a base, which may be a relatively weak base such as $K_2CO_3$, $Cs_2CO_3$, $Na_2CO_3$ and $NaHCO_3$.

In addition, a base such as sodium hydroxide is used to hydrolyze the carbazole derivative (A-3), to thereby produce carbazole derivative (A-4).

Synthesis Example 2 of the Compound Represented by General Formula (3)

The compound represented by General Formula (3) can be synthesized in the following manner.

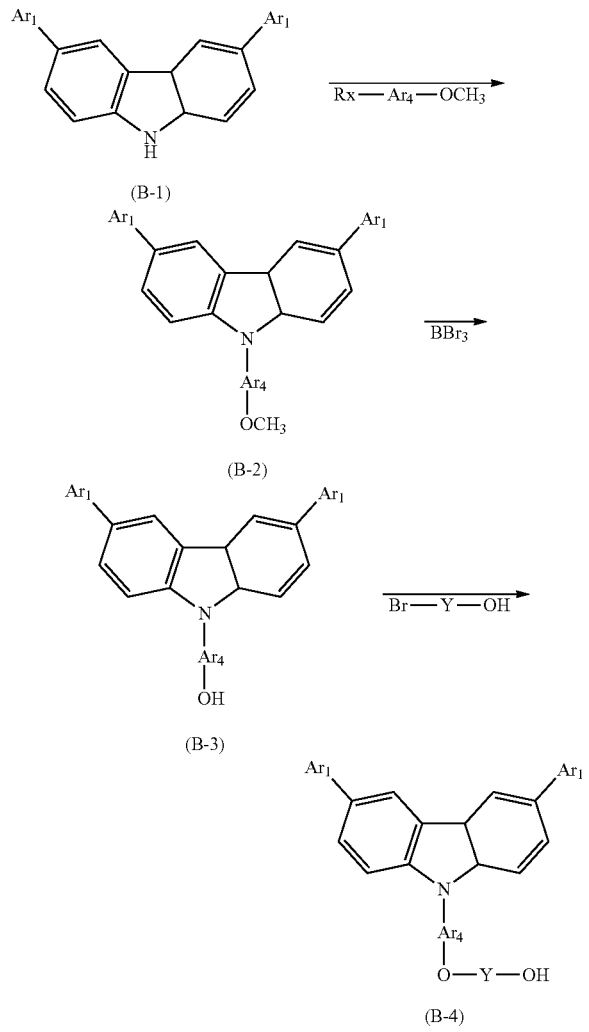

Synthesis Example 3 of the Compound Represented by General Formula (3)

The compound represented by General Formula (3) can be synthesized in the following manner.

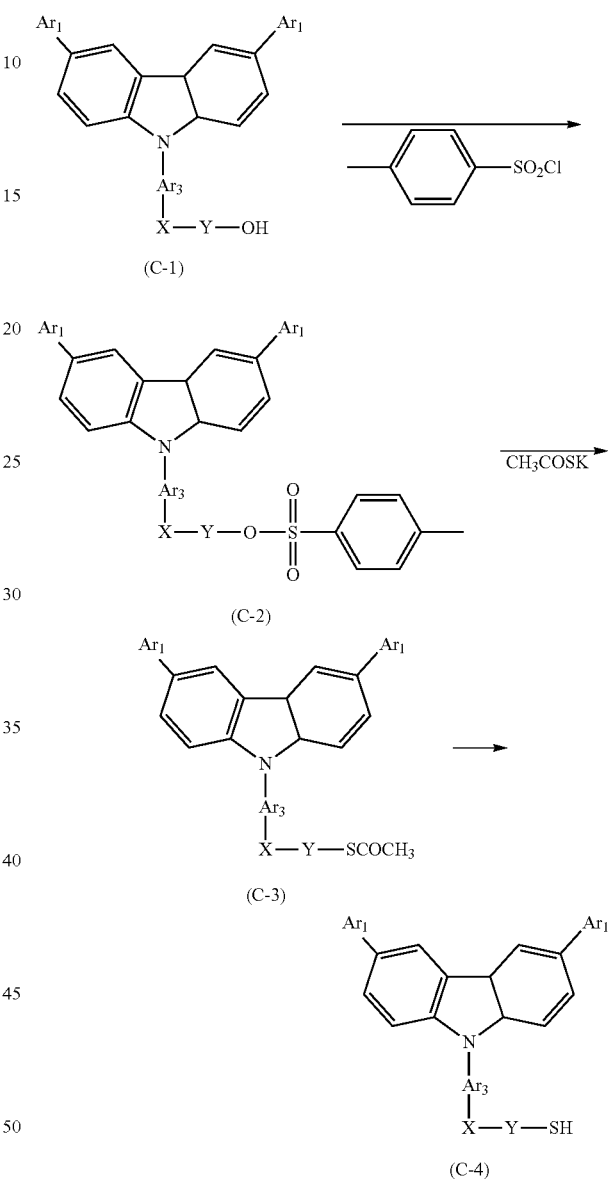

In the above reaction scheme, Rx represents a halogen atom, and $Ar_1$, $Ar_4$, X, Y and Z have the same meaning as defined above.

First, carbazole derivative (B-1) and aryl halide Rx-$Ar_4$—$OCH_3$ are subjected to Ullmann reaction or Buchwald-Hartwig amination reaction, to thereby produce carbazole derivative (B-2). Here, the carbazole derivative (B-1) is the same as the carbazole derivative (A-2).

Next, boron tribromide is used to perform demethylation of the carbazole derivative (B-2), to thereby produce carbazole derivative (B-3).

In addition, the carbazole derivative (B-3) and alcohol bromide Br—Y—OH are subjected to etherification reaction, to thereby produce carbazole derivative (B-4).

In the above reaction scheme, $Ar_1$, $Ar_3$, X, Y and Z have the same meanings as defined above.

First, in the presence of a base such as pyridine, p-toluenesulfonyl chloride is used to perform sulfonylation of the hydroxyl group of carbazole derivative (C-1), to thereby produce carbazole derivative (C-2).

Next, potassium thioacetate is used to perform methylthioesterification of the carbazole derivative (C-2), to thereby produce carbazole derivative (C-3).

In addition, a base such as sodium hydroxide is used to hydrolyze the carbazole derivative (C-3), to thereby produce carbazole derivative (C-4).

Synthesis Example 4 of the Compound Represented by General Formula (5)

The compound represented by General Formula (5) can be synthesized in the following manner.

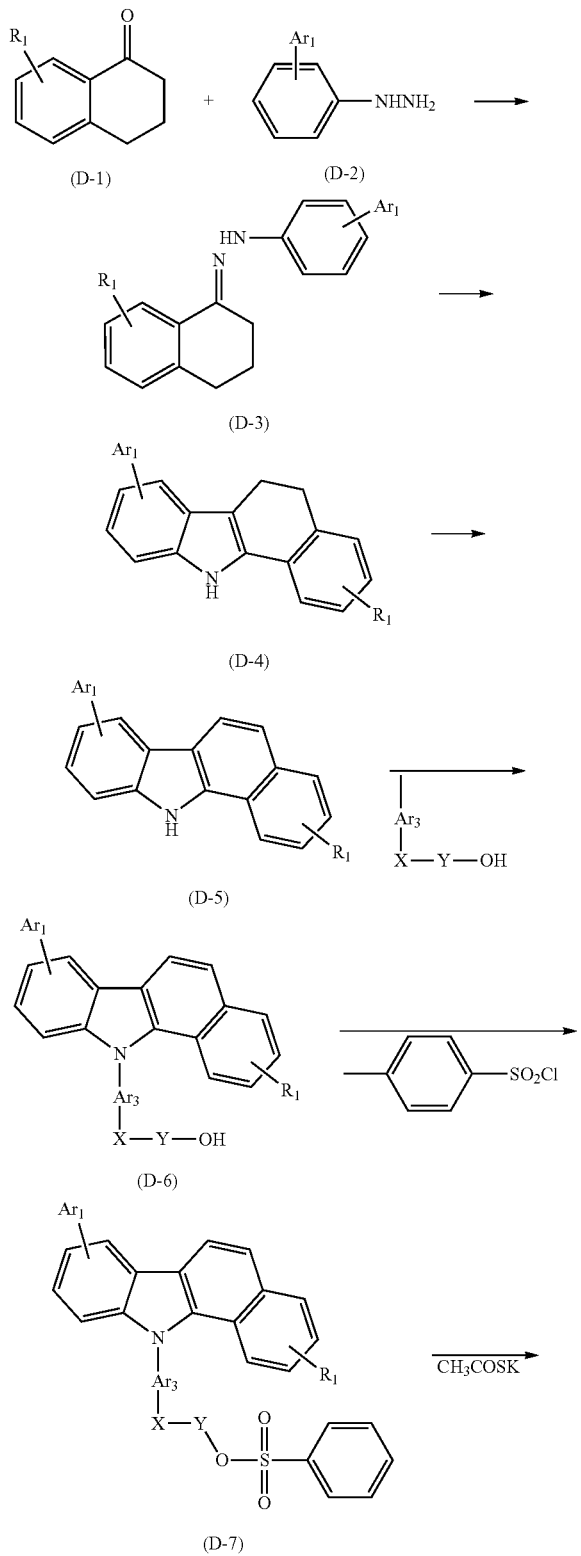

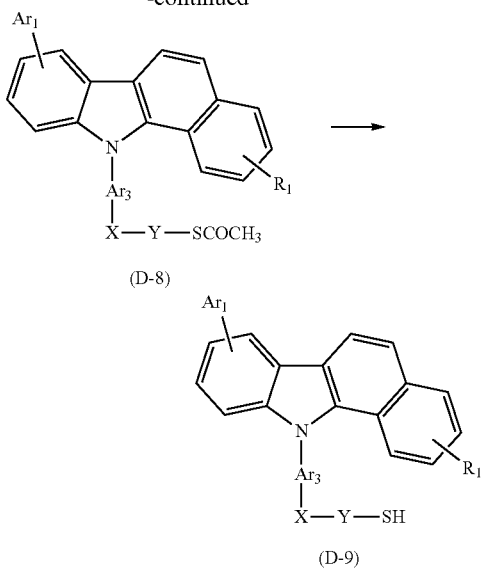

In the above reaction scheme, $R_1$, $Ar_1$, $Ar_3$, X, Y and Z have the same meanings as defined above.

First, in the presence of protonic acid, tetralone compound (D-1) and phenylhydrozine compound (D-2) are reacted together, to thereby produce hydrazone compound (D-3).

Next, the hydrazone compound (D-3) is cyclized in the presence of Lewis acid such as $ZnCl_2$, to thereby produce cyclic compound (D-4).

In addition, a catalyst such as Pd/C is used to oxidize the cyclic compound (D-4), to thereby produce benzocarbazole derivative (D-5).

Next, the benzocarbazole derivative (D-5) and aryl iodide I—$Ar_4$—X—Y—OH are subjected to Ullmann reaction or Buchwald-Hartwig amination reaction, to thereby produce benzocarbazole derivative (D-6).

Furthermore, in the presence of a base such as pyridine, p-toluenesulfonyl chloride is used to perform sulfonylation of the hydroxyl group of the benzocarbazole derivative (D-6), to thereby produce benzocarbazole derivative (D-7).

Next, potassium thioacetate is used to perform methylthioesterification of the benzocarbazole derivative (D-7), to thereby produce benzocarbazole derivative (D-8).

Moreover, a base such as sodium hydroxide is used to hydrolyze the benzocarbazole derivative (C-8), to thereby produce benzocarbazole derivative (C-9).

Synthesis Method of the Compound Represented by General Formula (6)

Synthesis Example 1 of the Compound Represented by General Formula (6)

The compound represented by General Formula (6) can be synthesized in the following manner.

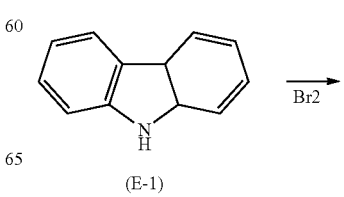

(E-1)

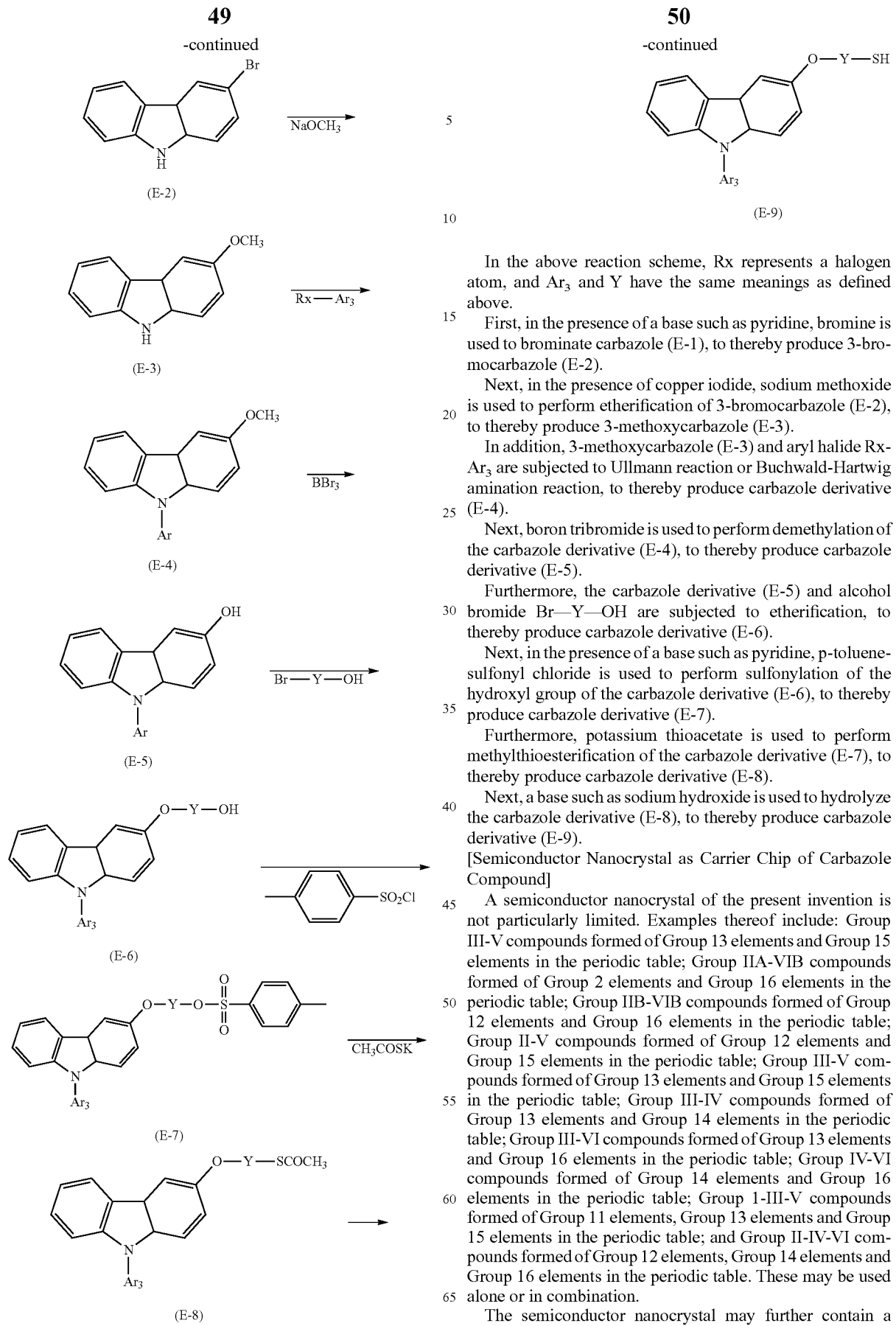

In the above reaction scheme, Rx represents a halogen atom, and $Ar_3$ and Y have the same meanings as defined above.

First, in the presence of a base such as pyridine, bromine is used to brominate carbazole (E-1), to thereby produce 3-bromocarbazole (E-2).

Next, in the presence of copper iodide, sodium methoxide is used to perform etherification of 3-bromocarbazole (E-2), to thereby produce 3-methoxycarbazole (E-3).

In addition, 3-methoxycarbazole (E-3) and aryl halide Rx-$Ar_3$ are subjected to Ullmann reaction or Buchwald-Hartwig amination reaction, to thereby produce carbazole derivative (E-4).

Next, boron tribromide is used to perform demethylation of the carbazole derivative (E-4), to thereby produce carbazole derivative (E-5).

Furthermore, the carbazole derivative (E-5) and alcohol bromide Br—Y—OH are subjected to etherification, to thereby produce carbazole derivative (E-6).

Next, in the presence of a base such as pyridine, p-toluenesulfonyl chloride is used to perform sulfonylation of the hydroxyl group of the carbazole derivative (E-6), to thereby produce carbazole derivative (E-7).

Furthermore, potassium thioacetate is used to perform methylthioesterification of the carbazole derivative (E-7), to thereby produce carbazole derivative (E-8).

Next, a base such as sodium hydroxide is used to hydrolyze the carbazole derivative (E-8), to thereby produce carbazole derivative (E-9).

[Semiconductor Nanocrystal as Carrier Chip of Carbazole Compound]

A semiconductor nanocrystal of the present invention is not particularly limited. Examples thereof include: Group III-V compounds formed of Group 13 elements and Group 15 elements in the periodic table; Group IIA-VIB compounds formed of Group 2 elements and Group 16 elements in the periodic table; Group IIB-VIB compounds formed of Group 12 elements and Group 16 elements in the periodic table; Group II-V compounds formed of Group 12 elements and Group 15 elements in the periodic table; Group III-V compounds formed of Group 13 elements and Group 15 elements in the periodic table; Group III-IV compounds formed of Group 13 elements and Group 14 elements in the periodic table; Group III-VI compounds formed of Group 13 elements and Group 16 elements in the periodic table; Group IV-VI compounds formed of Group 14 elements and Group 16 elements in the periodic table; Group 1-III-V compounds formed of Group 11 elements, Group 13 elements and Group 15 elements in the periodic table; and Group II-IV-VI compounds formed of Group 12 elements, Group 14 elements and Group 16 elements in the periodic table. These may be used alone or in combination.

The semiconductor nanocrystal may further contain a Group 3 element, a Group 4 element or a dopant.

The shape of the semiconductor nanocrystal is not particularly limited and may be appropriately selected depending on the intended purpose. Examples thereof include a spherical shape, a hemispherical shape, a rod shape, a disc shape, a tetrapod shape and a star shape.

When the semiconductor nanocrystal has a spherical shape, the average primary particle diameter of the semiconductor nanocrystal is generally 0.5 nm to 30 nm, preferably 1 nm to 15 nm. The particle size distribution of the semiconductor nanocrystal affects the chromaticity of light emission. The particle size distribution thereof is preferably narrow in order to obtain clear emission color with a narrow half width.

The method for producing the semiconductor nanocrystal is not particularly limited and may be appropriately selected depending on the intended purpose. Examples thereof include: a method described in pp. 27 and 28 and 48 to 180 of "Nanoparticles From Theory to Application" (published from NTS Inc., ISBN978-4-86043-175-4 C3040); and methods described in JP-A No. 2007-537886 (International Publication No. 2005/106082), JP-A No. 2009-504422 (International Publication No. 2007/020416), JP-A No. 2009-514993 (International Publication No. 2007/049052) and International Publication No. 2010/015824.

The semiconductor nanocrystal having the carbazole derivative bonded thereto via a coordination bond or intermolecular force can be obtained by replacing with the carbazole derivative the capping agent (surfactant) present on the surface of the semiconductor nanocrystal. The semiconductor nanocrystal having the carbazole derivative bonded thereto via a coordination bond or intermolecular force is produced as follows, for example. Specifically, the carbazole derivative is dissolved in a polar solvent such as methylene chloride, chloroform or dichloroethane. Next, the semiconductor nanocrystal is added to the resultant solution in an atmosphere of inert gas. The mixture was mixed and stirred at 0° C. to 30° C. for 12 hours or longer, preferably 24 hours or longer. The resultant mixture is ultrasonically washed with a relatively low-boiling-point solvent such as methanol, ethanol, isopropyl alcohol, methylene chloride, chloroform, acetone, tetrahydrofuran or hexane, to thereby obtain the semiconductor nanocrystal having the carbazole derivative bonded thereto via a coordination bond or intermolecular force.

Notably, whether the capping agent (surfactant) present on the surface of the semiconductor nanocrystal has been replaced with the carbazole derivative can be confirmed through FT-IR (infrared spectroscopy) or XPS (X-ray photoelectron spectroscopy).

The semiconductor nanocrystal may contain on the surface thereof other components than the carbazole derivative. The other components than the carbazole derivative are not particularly limited and may be appropriately selected depending on the intended purpose. Examples thereof include a capping agent (surfactant) used for producing the semiconductor nanocrystal.

The carbazole derivative may be bonded to the semiconductor nanocrystal via a coordination bond, or may be bonded to the semiconductor nanocrystal through interaction (e.g., intermolecular force) with the carbazole derivative bonded to the semiconductor nanocrystal via a coordination bond.

In the present invention, the semiconductor nanocrystal serves as a source of light emission. The carbazole derivative has a function of transferring excitation energy to the semiconductor nanocrystal through dipole-dipole interaction; i.e., Foerster-type energy transfer, and/or a function of directly injecting charges (i.e., holes and electrons) into the semiconductor nanocrystal. This increases the semiconductor nanocrystal in photoluminescence quantum yield and thus, the obtained photoluminescence element is excellent in light emission efficiency.

In order to efficiently perform Foerster-type energy transfer to the semiconductor nanocrystal, the carbazole derivative bonded via a coordination bond or intermolecular force to the semiconductor nanocrystal has to have an ionization potential (Ip) lower than that of the semiconductor nanocrystal and an electron affinity (Ea) greater than that of the semiconductor nanocrystal. For this reason, $Ar_1$, $Ar_2$ and $Ar_3$ in General Formula (1) and R in General Formula (4) or (5) are appropriately selected depending on the type of semiconductor nanocrystal.

Also, in order to efficiently perform Foerster-type energy transfer to the semiconductor nanocrystal and/or injection of charges into the semiconductor nanocrystal, the carbazole residue (main skeleton) of the carbazole derivative is preferably located proximately to the semiconductor nanocrystal. For this reason, X and Y in General Formula (2) are appropriately selected.

Furthermore, Z in General Formula (2) is a group bonded to the semiconductor nanocrystal via a coordination bond or intermolecular force, and is appropriately selected depending on the type of the semiconductor nanocrystal.

As described above, the semiconductor nanocrystal having the carbazole derivative bonded thereto via a coordination bond or intermolecular force functions as a light emitting material for a light emitting element. By appropriately selecting the size, size distribution, shape and composition of the semiconductor nanocrystal as well as the structure of the carbazole derivative depending on the intended application of light emitting elements, it is possible to obtain a light emitting element excellent in light emission efficiency.

EXAMPLES

The present invention will next be described in detail by way of Examples, which should not be construed as limiting the present invention thereto. In each Example, the units "part(s)" and "%" respectively mean "part(s) by mass" and "% by mass" unless otherwise specified.

Example 1

Synthesis of Carbazole Derivative 1

3,6-Dibromocarbazole (14.31 g, 44.0 mol), 5-methyl-2-thiophene boronic acid (25.01 g, 176.1 mmol) and tetrakis(triphenylphosphine)palladium (1.30 g) were added to a solvent mixture of toluene (180 mL) and ethanol (60 mL). Then, an aqueous solution of sodium carbonate (37.3 g) in distilled water (90 mL) was added to the mixture, followed by refluxing for 15 hours in a nitrogen atmosphere. Next, the resultant mixture was treated through hot filtration using a filtration aid to remove insoluble matter. Subsequently, the organic layer was separated, and the solvent was evaporated under reduced pressure. In addition, the residue was washed with water and dried to obtain a yellow-brown solid. Next, the obtained solid was purified through silica gel column chromatography using as an eluent a solvent mixture of methylene chloride/hexane (1/1 by volume), to thereby obtain 12.25 g of 3,6-bis(5-methylthiophen-2-yl)carbazole.

The obtained 3,6-bis(5-methylthiophen-2-yl)carbazole (8.07 g, 22.4 mmol), 4-iodoanisole (21.00 g, 89.7 mmol), copper powder (0.71 g) and potassium carbonate (12.40 g) were mixed together. The mixture was refluxed in a nitrogen atmosphere for 6 hours and cooled to 100° C. Next, toluene (80 mL) was added thereto, and the resultant mixture was filtrated using a filtration aid to remove insoluble matter. Thereafter, the solvent was evaporated under reduced pressure. The residue was dissolved in methylene chloride, and the solution was washed with water and dried to obtain a brown liquid. Next, the obtained liquid was purified through silica gel column chromatography using as an eluent a solvent mixture of methylene chloride/hexane (3/7 by volume), to thereby obtain 4.39 g of 3,6-bis(5-methylthiophen-2-yl)-9-(4-methoxyphenyl)carbazole.

The obtained 3,6-bis(5-methylthiophen-2-yl)-9-(4-methoxyphenyl)carbazole (3.73 g, 8.0 mmol) was dissolved in methylene chloride (30 mL). 1M Methylene chloride solution of boron tribromide (8 mL) was added dropwise to the resultant solution at −10° C., followed by stirring at room temperature. Next, the resultant mixture was washed with water and dried and the solvent was evaporated, to thereby obtain a gray solid. The obtained solid was purified through silica gel column chromatography using as an eluent a solvent mixture of methylene chloride/hexane (4/1 by volume), to thereby obtain 3.47 g of 3,6-bis(5-methylthiophen-2-yl)-9-(4-hydroxyphenyl)carbazole.

The obtained 3,6-bis(5-methylthiophen-2-O-9-(4-hydroxyphenyl)carbazole (1.81 g, 4.0 mmol) and 1,8-dibromooctane (4.35 g, 16.0 mmol) were dissolved in methyl ethyl ketone (20 mL). Then, potassium carbonate (0.83 g) was added to the resultant solution, followed by refluxing for 7 hours. Next, the resultant mixture was filtrated to remove insoluble matter, and the solvent was evaporated under reduced pressure. The residue was dissolved in methylene chloride, and the solution was washed with water and dried and the solvent was evaporated, to thereby obtain a pale yellow liquid. The obtained liquid was purified through silica gel column chromatography using as an eluent a solvent mixture of methylene chloride/hexane (2/3 by volume), to thereby obtain 1.83 g of 3,6-bis(5-methylthiophen-2-yl)-9-[4-(8-bromooctyl)phenyl]carbazole.

The obtained 3,6-bis(5-methylthiophen-2-yl)-9-[4-(8-bromooctyl)phenyl]carbazole (1.50 g, 2.3 mmol) was dissolved in a solvent mixture of tetrahydrofuran (THF) (20 mL) and ethanol (20 mL). Under nitrogen flow, potassium thioacetate (0.40 g, 3.5 mmol) was added to the resultant solution, and the mixture was refluxed for 5 hours and left to cool to room temperature. Next, the resultant mixture was poured to water, followed by extraction with methylene chloride. In addition, the mixture was washed with water and dried and the solvent was evaporated, to thereby a pale yellowish-white solid. The obtained solid was purified through silica gel column chromatography using as an eluent a solvent mixture of methylene chloride/hexane (13/7 by volume), to thereby obtain 1.22 g of 8-{4-[3,6-bis(5-methylthiophen-2-yl)carbazol-9-yl]phenoxy}octyl thioacetate.

Under nitrogen flow, the obtained 8-{4-[3,6-bis(5-methylthiophen-2-yl)carbazol-9-yl]phenoxy}octyl thioacetate (1.02 g, 1.6 mmol) was dissolved in a solvent mixture of tetrahydrofuran (THF) (30 mL) and ethanol (10 mL), and 50% by mass aqueous NaOH solution (0.5 mL) was added to the resultant solution, followed by stirring at room temperature for 1 hour. Next, the resultant mixture was poured to water, followed by extraction with chloroform. In addition, the mixture was washed with water and dried and the solvent was evaporated, to thereby obtain a crude product. Next, the crude product was purified through silica gel column chromatography using as an eluent a solvent mixture of chloroform/hexane (3/2 by volume), to thereby obtain 0.86 g of 8-{4-[3,6-bis(5-methylthiophen-2-yl)carbazol-9-yl]phenoxy}octane-1-thiol (hereinafter referred to as "carbazole derivative 1") expressed by the following Chemical Formula (I).

FIG. 1 is an infrared absorption spectrum (the KBr tablet method) of the obtained carbazole derivative 1.

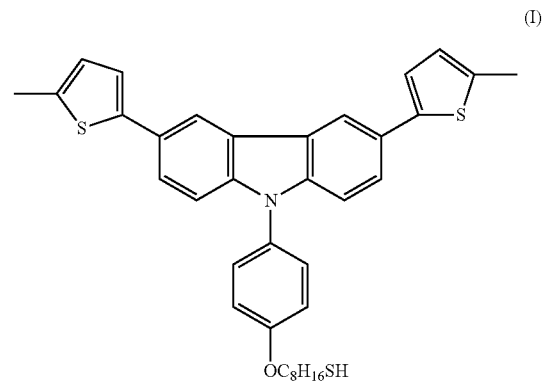

(I)

Example 2

Synthesis of Carbazole Derivative 2

3,6-Diphenyl-9-(4-methoxyphenyl)carbazole (4.20 g, 9.9 mmol) was dissolved in methylene chloride (30 mL). Then, 1M methylene chloride solution of boron tribromide (10 mL) was added dropwise to the resultant solution at −10° C., followed by stirring at room temperature. Next, the mixture was washed with water and dried and the solvent was evaporated, to thereby obtain 3.98 g of 3,6-diphenyl-9-(4-hydroxyphenyl)carbazole.

The obtained 3,6-diphenyl-9-(4-hydroxyphenyl)carbazole (1.54 g, 3.7 mmol) was dissolved in N,N-dimethylformamide (20 mL). Under cooling with ice water, 55% by mass sodium hydride (0.25 g, 5.7 mmol) was added to the resultant solution, followed by stirring for 1 hour. Next, 8-bromo-1-octanol (1.16 g, 5.5 mmol) was added thereto, and the resultant mixture was stirred for 3 hours at room temperature. In addition, the mixture was poured to water, followed by extraction with ethyl acetate. Next, the mixture was washed with water and dried and the solvent was evaporated, to thereby obtain 1.90 g of 8-[4-(3,6-diphenylcarbazol-9-yl)phenoxy]octan-1-ol.

The obtained 8-[4-(3,6-diphenylcarbazol-9-yl)phenoxy]octan-1-ol (2.80 g, 5.2 mmol) was dissolved in a solvent mixture of methylene chloride (10 mL) and pyridine (5 mL). Then, p-toluenesulfonyl chloride (1.20 g, 6.3 mmol) was added to the resultant solution at −10° C., followed by stirring at room temperature. Next, the mixture was poured to water, followed by extraction with ethyl acetate. In addition, the mixture was washed with diluted hydrochloric acid and water, and dried and the solvent was evaporated, to thereby obtain a crude product. The crude product was purified through silica gel column chromatography using as an eluent a solvent mixture of ethyl acetate/toluene (1/19 by volume), to thereby obtain 1.95 g of toluene-4-sulfonic acid 8-[4-(3,6-diphenylcarbazol-9-yl)phenoxy]octyl ester as colorless plate-like crystals.

The obtained toluene-4-sulfonic acid 8-[4-(3,6-diphenylcarbazol-9-yl)phenoxy]octyl ester (1.90 g, 2.7 mmol) was dissolved in a solvent mixture of tetrahydrofuran (THF) (40 mL) and ethanol (20 mL). Under nitrogen flow, potassium thioacetate (0.55 g, 4.8 mmol) was added to the resultant solution, and the mixture was refluxed for 7 hours and left to cool to room temperature. Next, the mixture was poured to water, followed by extraction with ethyl acetate. In addition, the mixture was washed with water and dried and the solvent was evaporated, to thereby obtain a crude product. The crude product was purified through silica gel column chromatography using toluene an eluent, to thereby obtain 1.32 g of thioacetic acid 8-[4-(3,6-diphenylcarbazol-9-yl)phenoxy]octyl ester as pale orange oily matter.

Under nitrogen flow, the obtained thioacetic acid 8-[4-(3,6-diphenylcarbazol-9-yl)phenoxy]octyl ester (1.32 g, 2.2 mmol) was dissolved in a solvent mixture of tetrahydrofuran (THF) (25 mL) and ethanol (10 mL), and 50% by mass aueous NaOH solution (0.5 mL) was added to the resultant solution, followed by stirring at room temperature for 30 min. Next, the mixture was poured to water, followed by extraction with chloroform. In addition, the mixture was washed with water and dried and the solvent was evaporated, to thereby obtain a crude product. Next, the crude product was purified through silica gel column chromatography using as an eluent a solvent mixture of chloroform/hexane (3/2 by volume), to thereby obtain 0.82 g of 8-[4-(3,6-diphenylcarbazol-9-yD-phenoxy]octane-1-thiol (hereinafter referred to as "carbazole derivative 2") expressed by the following Chemical Formula (II) as colorless needle crystals.

Figure 2:
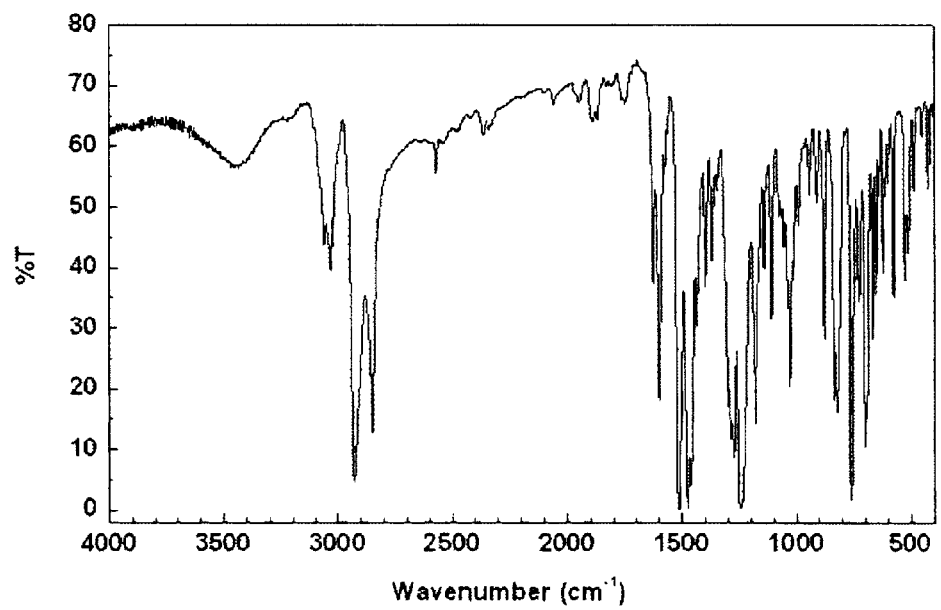
FIG. 2 is infrared absorption spectrum of carbazole derivative 2 of the present invention.

FIG. 2 is an infrared absorption spectrum (the KBr tablet method) of the obtained carbazole derivative 2.

Melting point: 131.0° C. to 131.5° C.

Elemental analysis (%) found (calculated): C, 81.70 (82.12), H, 6.57 (6.71), N, 2.45 (2.52), S, 5.68 (5.77)

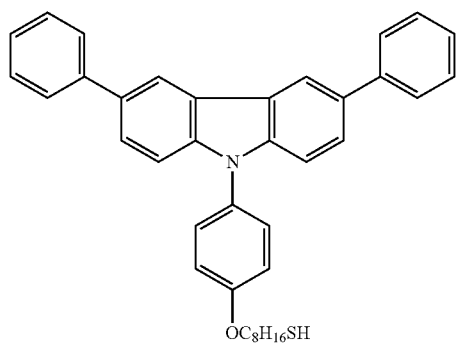

(II)

Example 3

Synthesis of Carbazole Derivative 3

The procedure of Example 2 was repeated, except that 3,6-diphenyl-9-(4-methoxyphenyl)carbazole was changed to 3,6-bis(3-methoxyphenyl)-N-(4-methoxyphenyl)carbazole, to thereby obtain 8-{4-[3,6-bis(3-methoxyphenyl)carbazol-9-yl]phenoxy}octane-1-thiol (hereinafter referred to as "carbazole derivative 3") expressed by the following Chemical Formula (III) as colorless oily matter.

Figure 3:
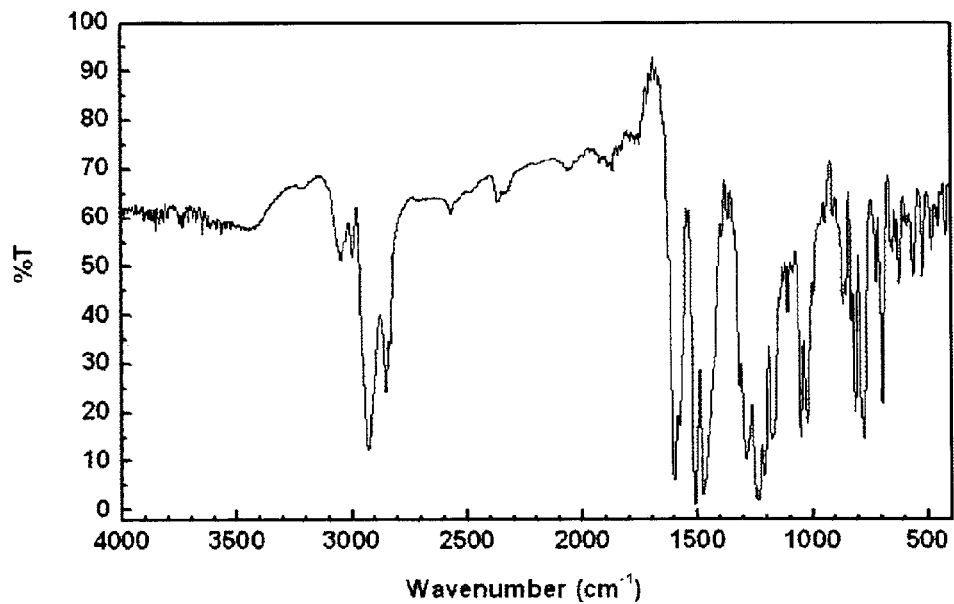
FIG. 3 is infrared absorption spectrum of carbazole derivative 3 of the present invention.

FIG. 3 is an infrared absorption spectrum (obtained using a NaCl cast film) of the obtained carbazole derivative 3.

Elemental analysis (%) found (calculated): C, 77.70 (78.01) H, 6.81 (6.71) N, 2.16 (2.27) S, 4.97 (5.21)

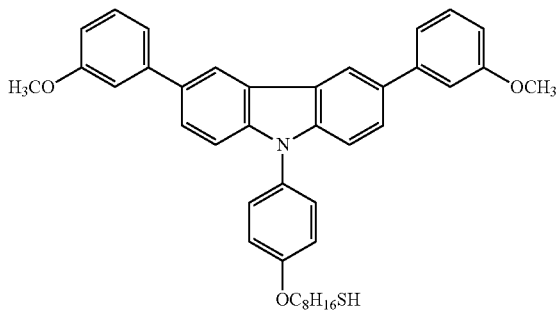

(III)

Example 4

Synthesis of Carbazole Derivative 4

3-Methoxy-9-phenylcarbazole was subjected to demethylation in the same manner as in Example 1, to thereby obtain 3-hydroxy-9-phenylcarbazole as colorless needle crystals (yield: 91.8%).

Melting point: 148.5° C. to 150.0° C.

The obtained 3-hydroxy-9-phenylcarbazole and 8-bromooctanol were reacted together in the same manner as in Example 2, to thereby obtain 3-(8-hydroxyoctyloxy)-9-phenylcarbazole as colorless needle crystals (yield: 84.3%).

Melting point: 85.5° C. to 87.5° C.

In an infrared absorption spectrum (the KBr tablet method), the stretching vibration of the OH was observed at 3,563 cm$^{-1}$.

Next, the obtained 3-(8-hydroxyoctyloxy)-9-phenylcarbazole was tosylated, thioacetylated and hydrolyzed in the same manner as in Example 2, to thereby obtain 3-(8-mercaptooctyloxy)-9-phenylcarbazole (hereinafter referred to as "carbazole derivative 4") expressed by the following Chemical Formula (IV) as colorless needle crystals.

Figure 4:
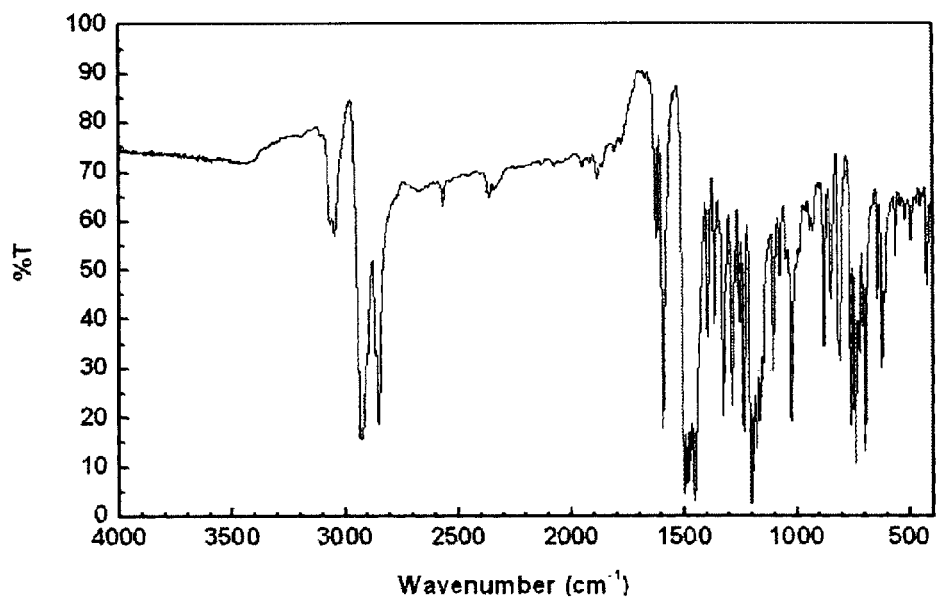
FIG. 4 is infrared absorption spectrum of carbazole derivative 4 of the present invention.

FIG. 4 is an infrared absorption spectrum (the KBr tablet method) of the obtained carbazole derivative 4.

Melting point: 52.5° C. to 55.5° C.

Elemental analysis (%) found (calculated): C, 77.32 (77.38) H, 7.15 (7.24) N, 3.40 (3.47) S, 7.74 (7.95)

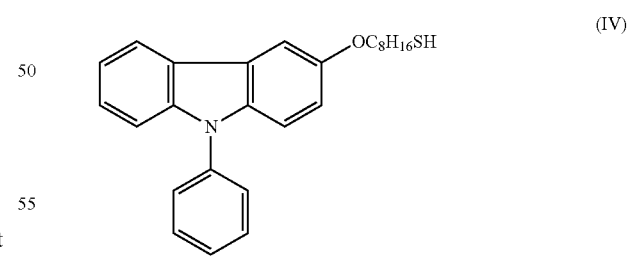

(IV)

Example 5

Synthesis of Carbazole Derivative 5

Benzo[α]carbazole obtained following the Synthesis Example 4 (2.17 g), 4-(8-hydroxyoctyloxy)iodobenzene (3.50 g), potassium carbonate (2.80 g), copper powder (0.5 g) and nitrobenzene (15 mL) were stirred under nitrogen flow at 190° C. to 200° C. for 6 hours. After left to cool to room temperature, the mixture was filtrated through CELITE to remove insoluble matter, and the solvent was evaporated with heating under reduced pressure. The resultant mixture was chromatographically treated (silica gel, eluent toluene/ethyl acetate=4/1 (by mass)) to thereby obtain 3.3 g of N-[4-(8-hydroxyoctyloxyphenyl)]-11H-benzo[α]carbazole as pale brown oily matter.

In an infrared absorption spectrum (obtained using a NaCl cast film), the stretching vibration of the OH was observed at 3,360 cm$^{-1}$.

Next, the obtained N-[4-(8-hydroxyoctyloxyphenyl)]-11H-benzo[a]carbazole was tosylated, thioacetylated and hydrolyzed in the same manner as in Example 2, to thereby obtain N-[4-(8-mercaptooctyloxyphenyl)]-11H-benzo[a]carbazole (hereinafter referred to as "carbazole derivative 5") of the present invention expressed by the following Chemical Formula (V) as colorless prism crystals.

Figure 5:
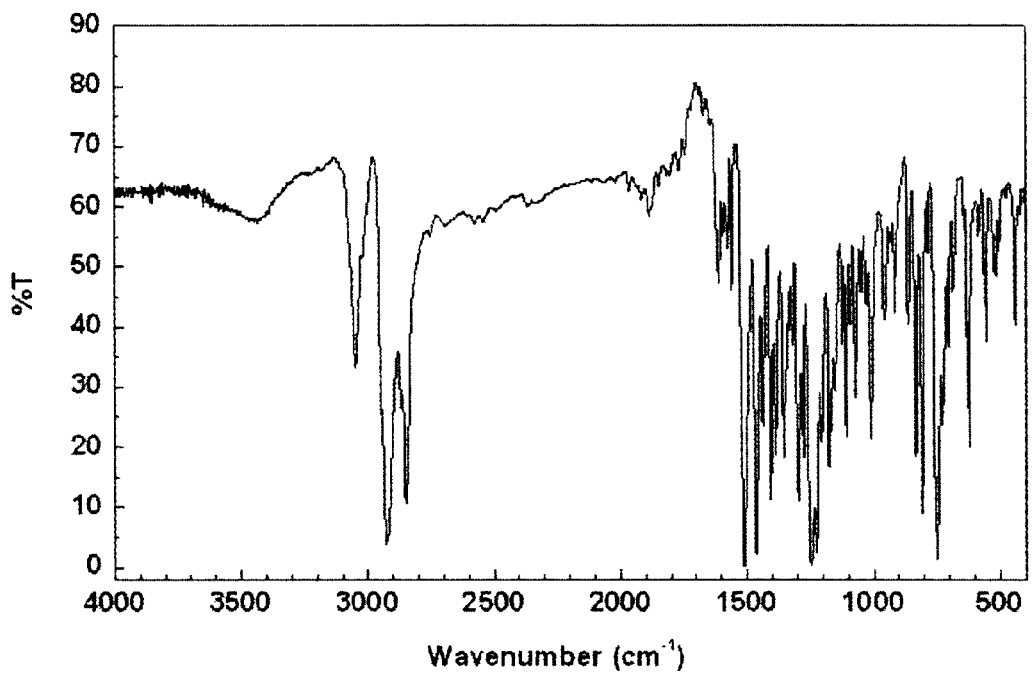
FIG. 5 is infrared absorption spectrum of carbazole derivative 5 of the present invention.

FIG. 5 is an infrared absorption spectrum (the KBr tablet method) of the obtained carbazole derivative 5.

Melting point: 75.0° C. to 76.0° C.

Elemental analysis (%) found (calculated): C, 79.48 (79.43) H, 6.76 (6.89) N, 2.78 (3.09) S, 6.99 (7.07)

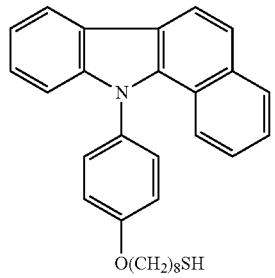

(V)

Example 6

Synthesis of Carbazole Derivative 6

Toluene (80 mL), ethanol (20 mL) and 2M sodium carbonate aqueous solution (40 g) were added to a mixture of 2,7-dibromocarbazole (6.50 g), phenylboronic acid (7.32 g) and tetrakistriphenylphosphine palladium (0.734 g), followed by refluxing under nitrogen flow for 3 hours.

The resultant mixture was left to cool to room temperature. Then, the insoluble matter was filtrated and the solvent was evaporated, to thereby obtain 4.15 g of 2,7-diphenylcarbazole as pale brown powder.

The obtained 2,7-diphenylcarbazole (4.01 g), 4-(8-hydroxyoctyloxy)iodobenzene (4.37 g), potassium carbonate (3.45 g), copper powder (0.5 g) and nitrobenzene (20 mL) were refluxed under nitrogen flow for 7 hours. The resultant mixture was left to cool to room temperature. The insoluble matter was filtrated and the solvent was evaporated. The resultant product was chromatographically treated (silica gel, eluent: 10% ethyl acetate/toluene), to thereby obtain 2.0 g of 2,7-diphenyl-N-[4-(8-hydroxyoctyloxyphenyl)]carbazole as pale brown oily matter.

Next, 2,7-diphenyl-N-[4-(8-hydroxyoctyloxyphenyl)]carbazole was tosylated, thioacetylated and hydrolyzed in the same manner as in Example 2, to thereby obtain 2,7-diphenyl-N-[4-(8-mercaptooctyloxyphenyl]carbazole (hereinafter referred to as "carbazole derivative 6") expressed by the following Chemical Formula (VI) as colorless needle crystals.

Figure 6:
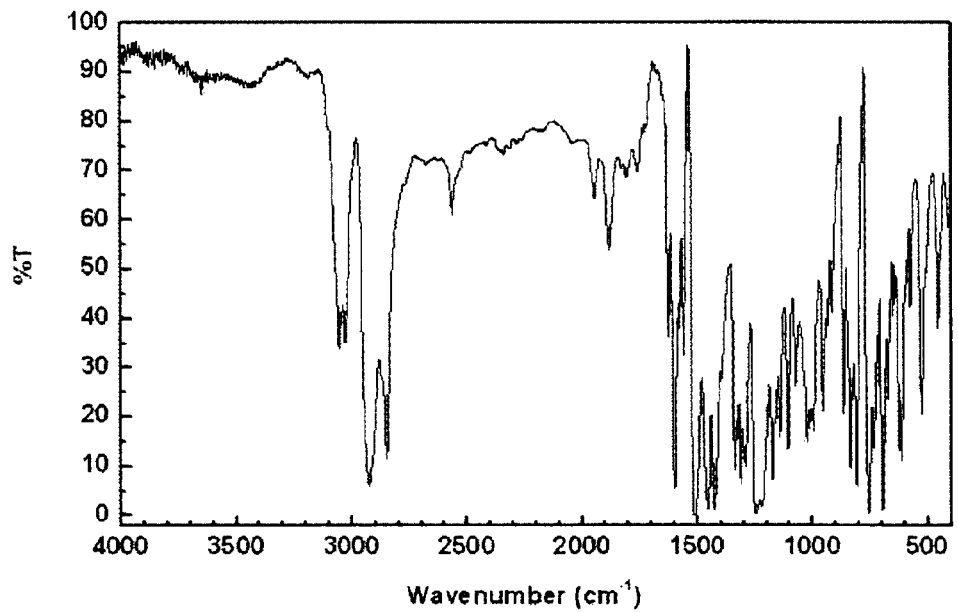
FIG. 6 is infrared absorption spectrum of carbazole derivative 6 of the present invention.

FIG. 6 is an infrared absorption spectrum (the KBr tablet method) of the obtained carbazole derivative 6.

Melting point: 132.5° C. to 133.5° C.

Elemental analysis (%) found (calculated): C, 82.37 (82.12) H, 6.66 (6.71) N, 2.43 (2.52) S, 5.70 (5.77)

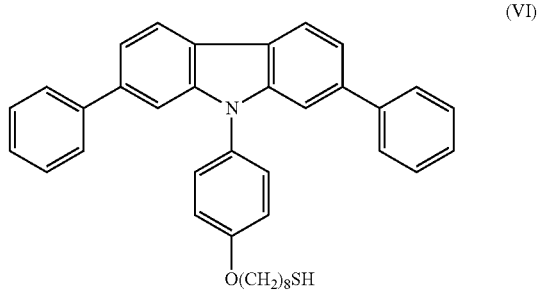

(VI)

Example 7

Synthesis of Carbazole Derivative 7

The procedure of Example 2 was repeated, except that 8-bromo-1-octanol was changed to 4-bromo-1-butanol, to thereby obtain 4-[4-(3,6-diphenylcarbazol-9-yl)phenoxy]butane-1-thiol (hereinafter referred to as "carbazole derivative 7") expressed by the following Chemical Formula (VII) as a white solid.

Figure 7:
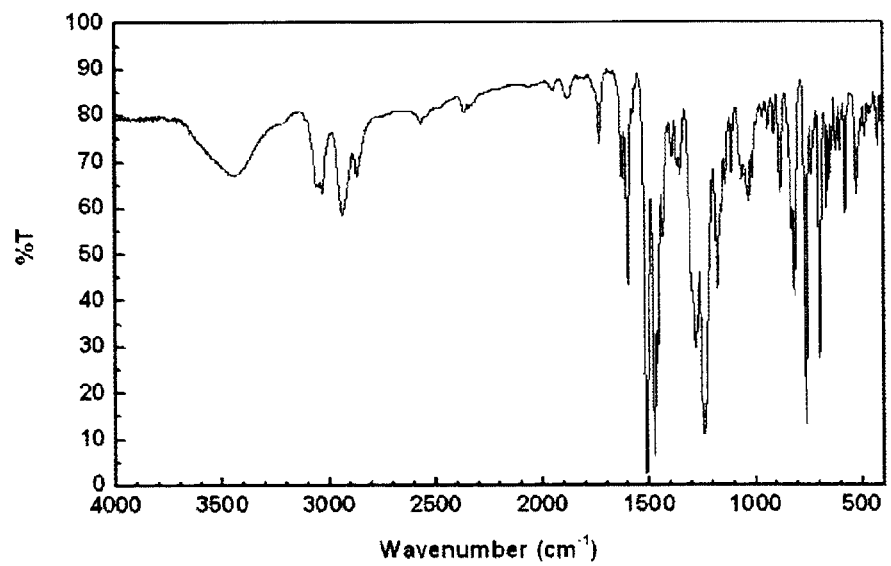
FIG. 7 is infrared absorption spectrum of carbazole derivative 7 of the present invention.

FIG. 7 is an infrared absorption spectrum (the KBr tablet method) of the obtained carbazole derivative 7.

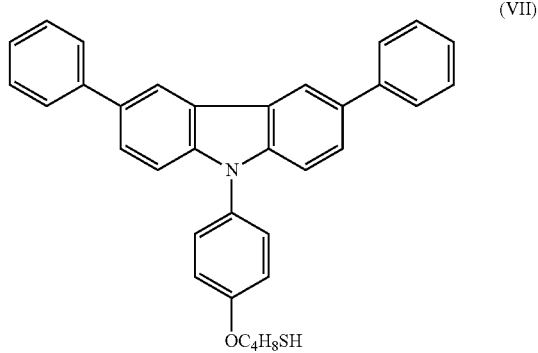

(VII)

Example 8

Synthesis of Carbazole Derivative 8

The procedure of Example 1 was repeated, except that 3,6-bis(5-methylthiophen-2-yl)carbazole was changed to 3,6-diphenyl-9-(4-methoxyphenyl)carbazole and that 4-iodoanisole was changed to 3-iodoanisole, to thereby obtain 8-[3-(3,6-diphenylcarbazol-9-yl)phenoxy]octane-1-thiol (hereinafter referred to as "carbazole derivative 8") expressed by the following Chemical Formula (VIII) as colorless, highly viscous matter.

Figure 8:
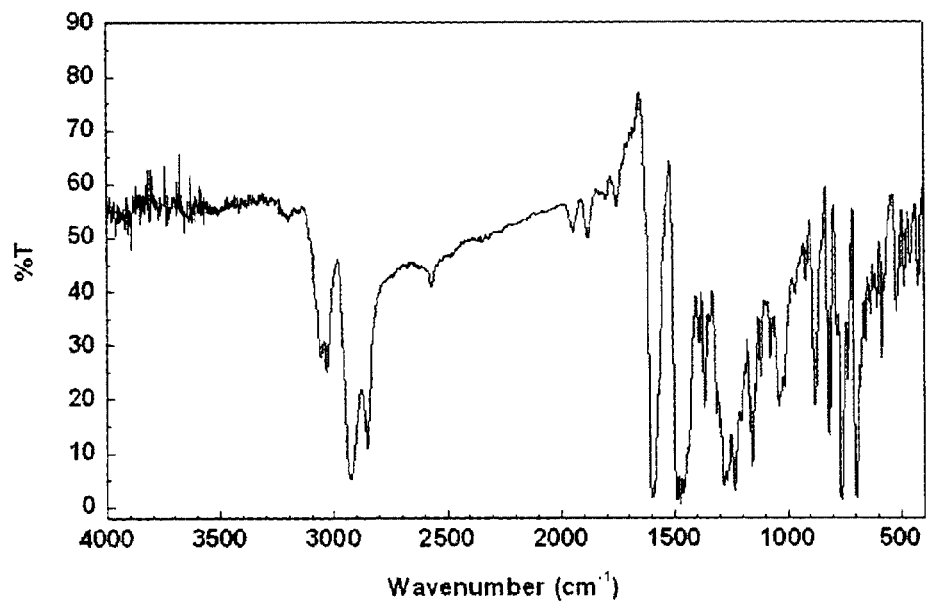
FIG. 8 is infrared absorption spectrum of carbazole derivative 8 of the present invention.

FIG. 8 is an infrared absorption spectrum (obtained using a NaCl cast film) of the obtained carbazole derivative 8.

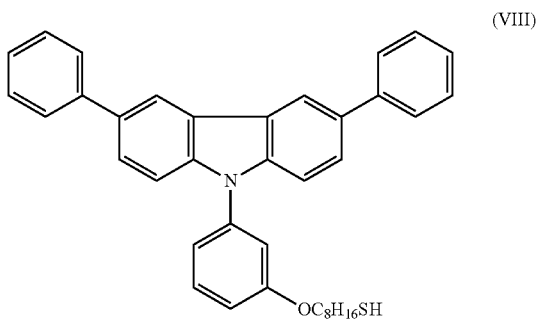
(VIII)

Example 9

Synthesis of Carbazole Derivative 9

3,6-Diphenylcarbazole (2.80 g, 8.77 mmol), 1-bromo-3-iodobenzene (22.18 g, 87.7 mmol), copper powder (0.279 g) and potassium carbonate (4.85 g) were mixed together, and the mixture was heated in a nitrogen atmosphere at 190° C. for 9 hours. The resultant mixture was cooled to room temperature and diluted with methylene chloride, followed by washing with water and drying, to thereby obtain a pale brown liquid. Next, the obtained liquid is purified through silica gel column chromatography using a solvent mixture of methylene chloride/hexane (2/3 by volume), to thereby obtain 3.59 g of 9-(3-bromophenyl)-3,6-diphenylcarbazole.

The obtained 9-(3-bromophenyl)-3,6-diphenylcarbazole (3.20 g, 6.75 mmol), 3-methoxyphenylboronic acid (1.54 g, 10.1 mmol) and tetrakis(triphenylphosphine)palladium (0.124 g) were added to a solvent mixture of toluene (30 mL) and ethanol (10 mL). Then, an aqueous solution of sodium carbonate (37.3 g) in distilled water (90 mL) was added the mixture. The resultant mixture was refluxed for 9 hours in a nitrogen atmosphere and then cooled to room temperature. The obtained mixture was diluted with methylene chloride and the insoluble matter was removed through filtration. The organic layer was washed with water and separated. The solvent was evaporated under reduced pressure. The residue was purified through silica gel column chromatography using as an eluent a solvent mixture of methylene chloride/hexane (2/3 by volume), to thereby obtain 2.89 g of [3'-(3,6-diphenylcarbazol-9-yl)biphenyl-3-yloxy]methane.

The procedure of Example 1 was repeated, except that the obtained [3'-(3,6-diphenylcarbazol-9-yDbiphenyl-3-yloxy] methane was used instead of 3,6-bis(5-methylthiophen-2-yl)-9-(4-methoxyphenyl)carbazole, to thereby obtain 8-[3'-(3,6-diphenylcarbazol-9-yl)biphenyl-3-yloxy]octane-1-thiol (hereinafter referred to as "carbazole derivative 9") expressed by the following Chemical Formula (IX).

Figure 9:
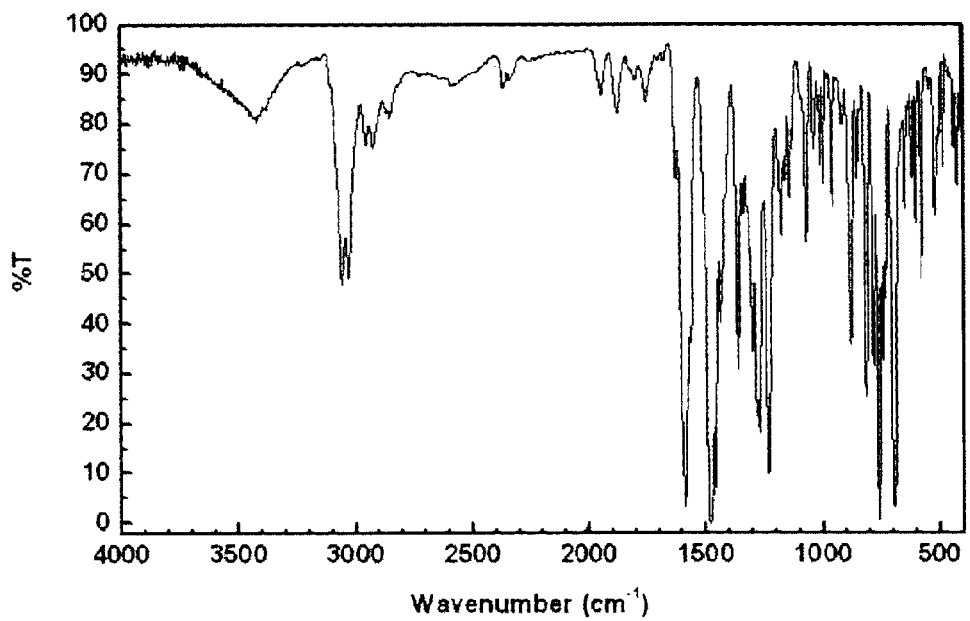
FIG. 9 is infrared absorption spectrum of carbazole derivative 9 of the present invention.

FIG. 9 is an infrared absorption spectrum (the KBr tablet method) of the obtained carbazole derivative 9.

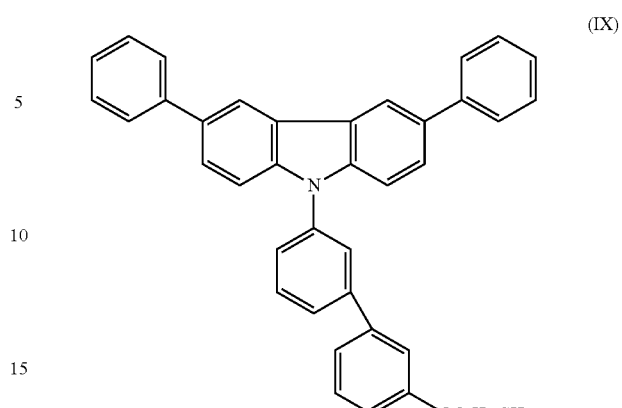
(IX)

Example 10

Synthesis of Carbazole Derivative 10

3,6-Bis(4-methoxyphenyl)carbazole (0.76 g, 2 mmol), 4-(4-bromophenyl)butylic acid ethyl ester (0.54 g, 2 mmol), palladium acetate (0.045 g, 0.20 mmol), di(1-adamantyl)-n-butylphosphine (0.14 g, 0.40 mmol) and potassium carbonate (1.38 g, 10 mmol) were added to toluene (40 mL) in an argon atmosphere, followed by refluxing for 16 hours. The insoluble matter was removed using a filtration aid and the solvent was evaporated. The residue was washed with water and dried to obtain 1.43 g of brown viscous matter. The brown viscous matter was purified through silica gel column chromatography using as an eluent a solvent mixture of methylene chloride/hexane (9/1 by volume), to thereby obtain 0.97 g of 4-{4-[3,6-bis(3-methoxyphenyl)carbazol-9-yl] phenyl}butylic acid ethyl ester.

The obtained ester compound (0.73 g, 1.28 mmol) was added to methanol (40 mL). A solution of sodium hydroxide (0.21 g) in distilled water (5 mL) was added to the resultant mixture. The obtained mixture was refluxed for 9 hours and cooled to room temperature. Next, diluted hydrochloric acid was added to the resultant mixture under stirring until the pH reached 3. The precipitated white matter was extracted with methylene chloride, washed with water and dried, to thereby obtain 0.57 g of a white solid. The obtained solid was purified with a recycle HPLC (name of apparatus: Recycling Preparative HPLC LC-9201, product of Japan Analytical Industry Co., Ltd., developing solvent: THF, flow rate: 3.5 mL/min), to thereby obtain 0.53 g of 4-{4-[3,6-bis(3-methoxyphenyl)carbazol-9-yl]phenyl}butylic acid (hereinafter referred to as "carbazole derivative 10") expressed by the following Chemical Formula (X).

Figure 10:
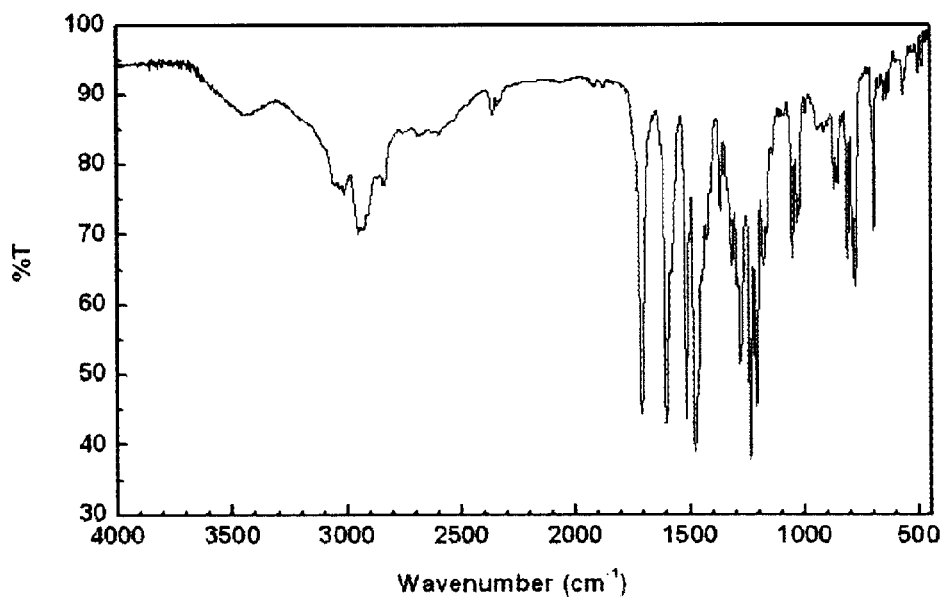
FIG. 10 is infrared absorption spectrum of carbazole derivative 10 of the present invention.

FIG. 10 is an infrared absorption spectrum (the KBr tablet method) of the obtained carbazole derivative 10.

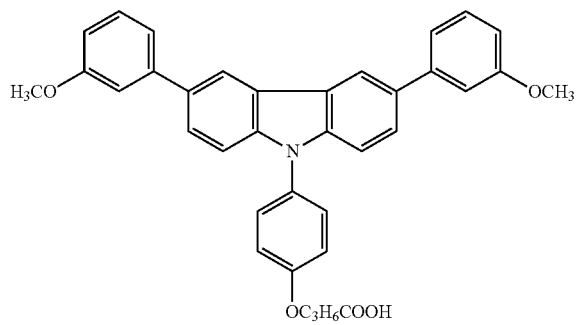

(X)

Example 11

The carbazole derivative 1 (0.01 g) obtained in Example 1 was dissolved in chloroform (2 mL) in an argon atmosphere at room temperature. Separately, a toluene solution (concentration: 10 mg/mL) of a semiconductor nanocrystal (InP/ZnS/ZnO, a capping agent (surfactant): 10-undecylenic acid) was prepared in the same manner as described in Examples 4 and 5 of International Publication No. WO2010/015824. The thus-prepared toluene solution (0.5 mL) was added to the chloroform solution in an argon atmosphere, followed by stirring for 24 hours at room temperature. Then, dry tetrahydrofuran (20 mL) was added to the mixture. The resultant mixture was ultrasonically washed for 5 min and centrifugated. The precipitates were isolated and dry tetrahydrofuran (20 mL) was added thereto. A series of the washing and the centrifugating was repeated twice similar to the above. The precipitates were isolated and dried under argon flow to thereby obtain a semiconductor nanocrystal containing the carbazole derivative 1 bonded thereto via a coordination bond or intermolecular force.

Figure 11:
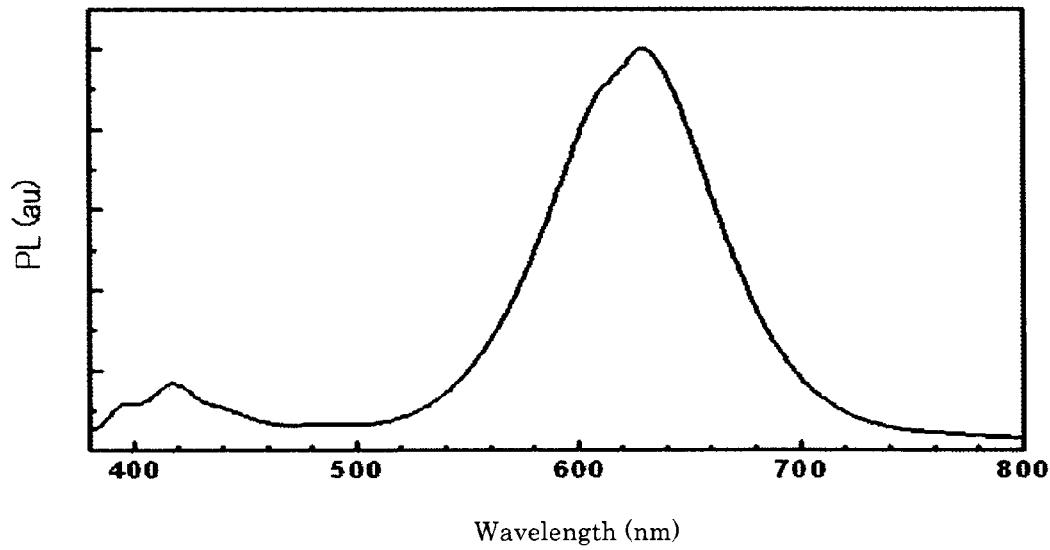
FIG. 11 is a photoluminescence (PL) spectrum (excitation light: 365 nm) of a toluene solution of a semiconductor nanocrystal obtained from carbazole derivative 1 of the present invention.
Figure 12:
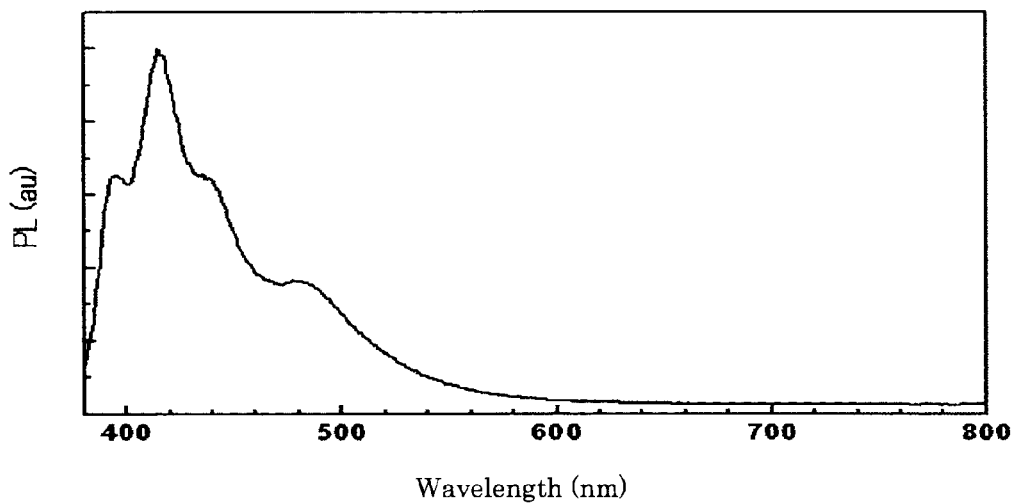
FIG. 12 is a photoluminescence (PL) spectrum of a toluene solution of another semiconductor nanocrystal obtained from carbazole derivative 1 of the present invention.
Figure 13:
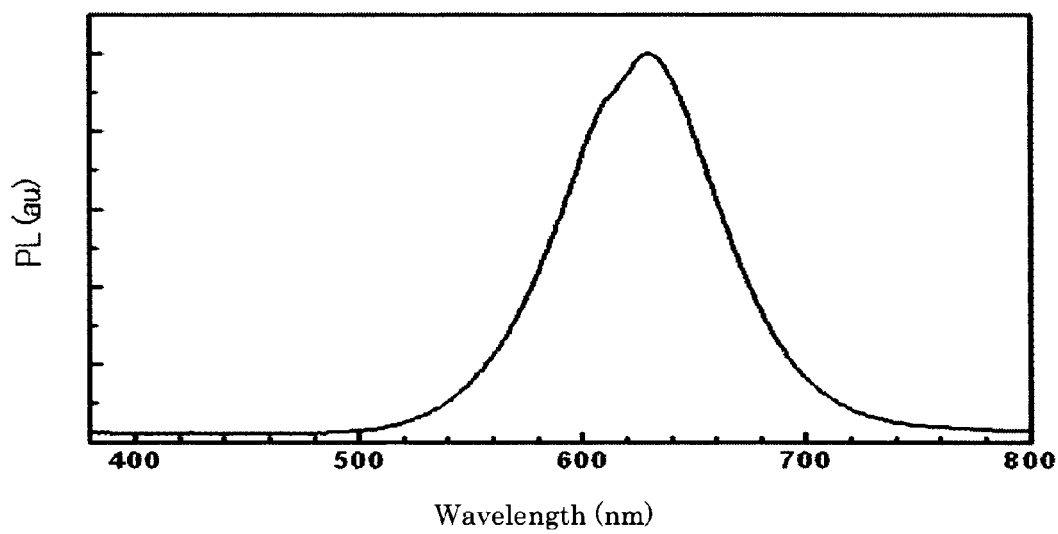
FIG. 13 is a photoluminescence (PL) spectrum of a toluene solution of still another semiconductor nanocrystal obtained from carbazole derivative 1 of the present invention.

FIG. 11 is a photoluminescence (PL) spectrum (excitation light: 365 nm) of a toluene solution of the obtained semiconductor nanocrystal. FIG. 12 is a PL spectrum (excitation light: 365 nm) of the toluene solution of the semiconductor nanocrystal prepared in the same manner as described in Examples 4 and 5 of International Publication No. WO2010/015824. FIG. 13 is PL spectrum (excitation light: 365 nm) of a toluene solution of the carbazole derivative 1. Notably, the photoluminescence (PL) spectrum was measured with an Absolute PL Quantum Yield Measurement System (product of Hamamatsu Photonics K.K., excitation wavelength: 365 nm).

In the semiconductor nanocrystal containing the carbazole derivative 1 bonded thereto via a coordination bond or intermolecular force, almost no light emission due to excitation light of 365 nm was observed from the carbazole derivative 1. However, there was observed emission of light having a peak wavelength of about 620 nm derived from the semiconductor nanocrystal. This suggests that there occurred Foerster-type energy transfer from the carbazole derivative to the semiconductor nanocrystal.

Example 12

The procedure of Example 11 was repeated, except that the carbazole derivative 2 obtained in Example 2 was used, to thereby obtain a semiconductor nanocrystal containing the carbazole derivative 2 bonded thereto via a coordination bond or intermolecular force.

Figure 14:
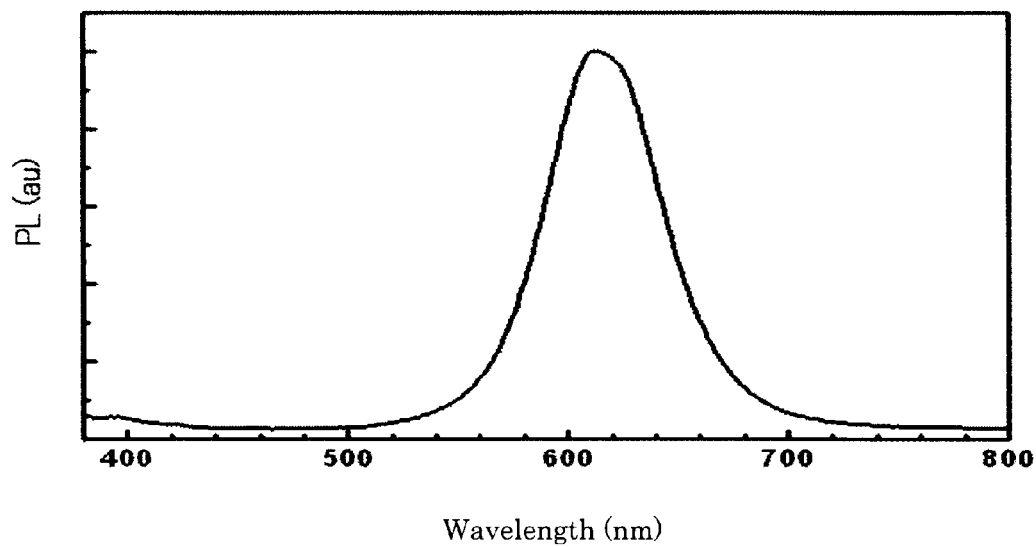
FIG. 14 is a photoluminescence (PL) spectrum of a toluene solution of a semiconductor nanocrystal obtained from carbazole derivative 2 of the present invention.

FIG. 14 is a PL spectrum (excitation light: 365 nm) of a toluene solution of the obtained semiconductor nanocrystal.

Example 13

The procedure of Example 11 was repeated, except that the carbazole derivative 3 obtained in Example 3 was used, to thereby obtain a semiconductor nanocrystal containing the carbazole derivative 3 bonded thereto via a coordination bond or intermolecular force.

Figure 15:
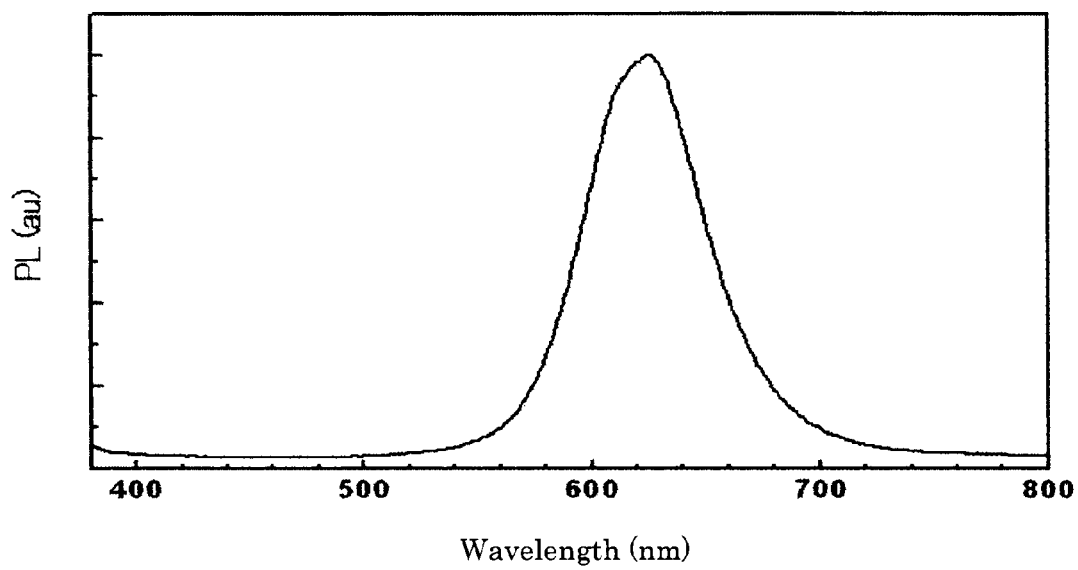
FIG. 15 is a photoluminescence (PL) spectrum of a toluene solution of a semiconductor nanocrystal obtained from carbazole derivative 3 of the present invention.

FIG. 15 is a PL spectrum (excitation light: 365 nm) of a toluene solution of the obtained semiconductor nanocrystal.

Example 14

The procedure of Example 11 was repeated, except that the carbazole derivative 4 obtained in Example 4 was used, to thereby obtain a semiconductor nanocrystal containing the carbazole derivative 4 bonded thereto via a coordination bond or intermolecular force.

Figure 16:
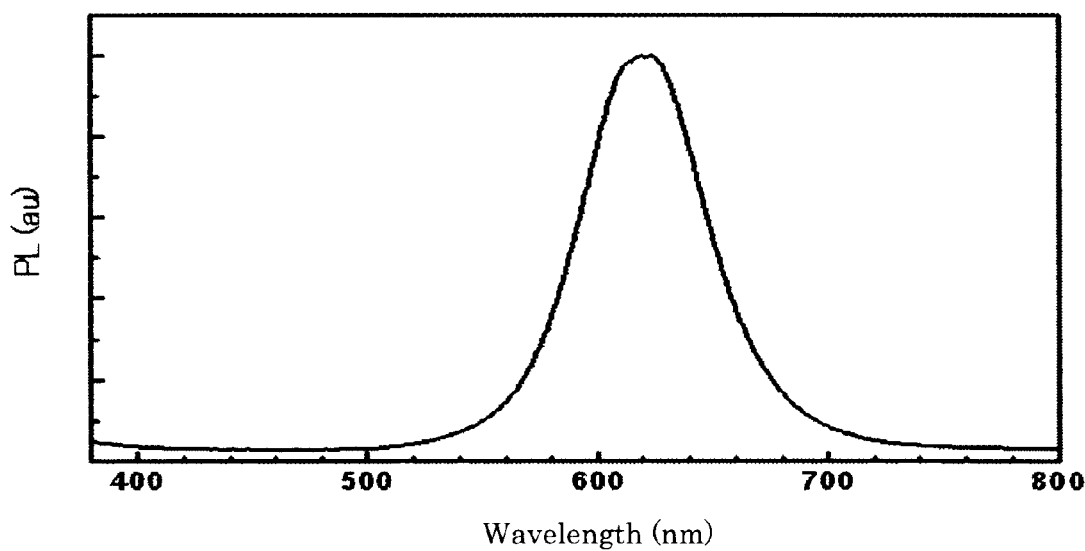
FIG. 16 is a photoluminescence (PL) spectrum of a toluene solution of a semiconductor nanocrystal obtained from carbazole derivative 4 of the present invention.

FIG. 16 is a PL spectrum (excitation light: 365 nm) of a toluene solution of the obtained semiconductor nanocrystal.

Example 15

The procedure of Example 11 was repeated, except that the carbazole derivative 5 obtained in Example 5 was used, to thereby obtain a semiconductor nanocrystal containing the carbazole derivative 5 bonded thereto via a coordination bond or intermolecular force.

Figure 17:
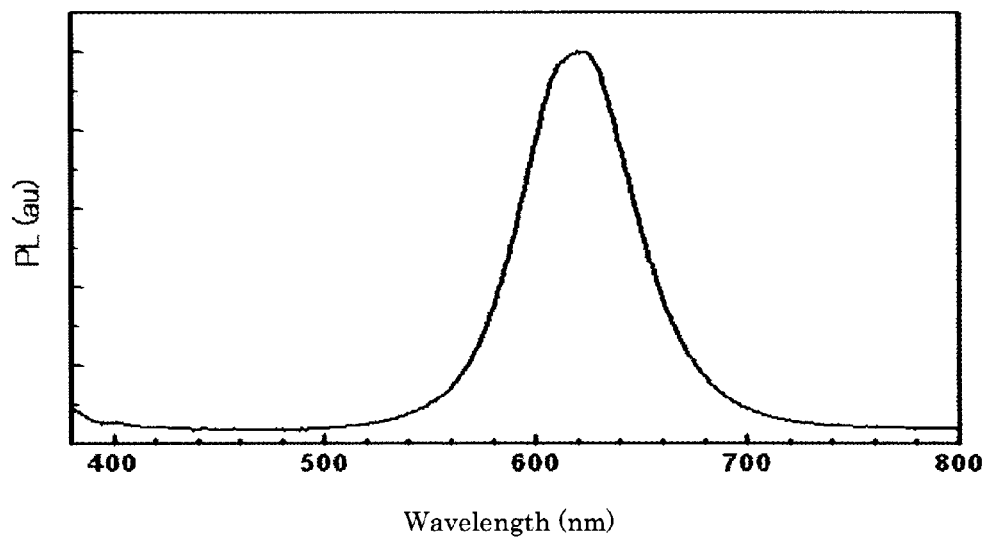
FIG. 17 is a photoluminescence (PL) spectrum of a toluene solution of a semiconductor nanocrystal obtained from carbazole derivative 5 of the present invention.

FIG. 17 is a PL spectrum (excitation light: 365 nm) of a toluene solution of the obtained semiconductor nanocrystal.

Example 16

The procedure of Example 11 was repeated, except that the carbazole derivative 6 obtained in Example 6 was used, to thereby obtain a semiconductor nanocrystal containing the carbazole derivative 6 bonded thereto via a coordination bond or intermolecular force.

Figure 18:
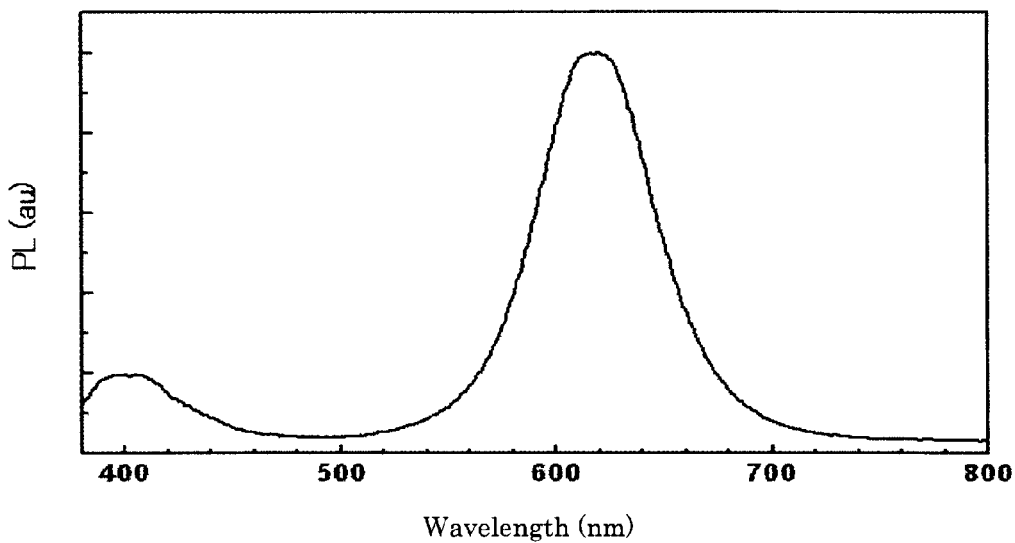
FIG. 18 is a photoluminescence (PL) spectrum of a toluene solution of a semiconductor nanocrystal obtained from carbazole derivative 6 of the present invention.

FIG. 18 is a PL spectrum (excitation light: 365 nm) of a toluene solution of the obtained semiconductor nanocrystal.

Example 17

The procedure of Example 11 was repeated, except that the carbazole derivative 7 obtained in Example 7 was used, to thereby obtain a semiconductor nanocrystal containing the carbazole derivative 7 bonded thereto via a coordination bond or intermolecular force.

Figure 19:
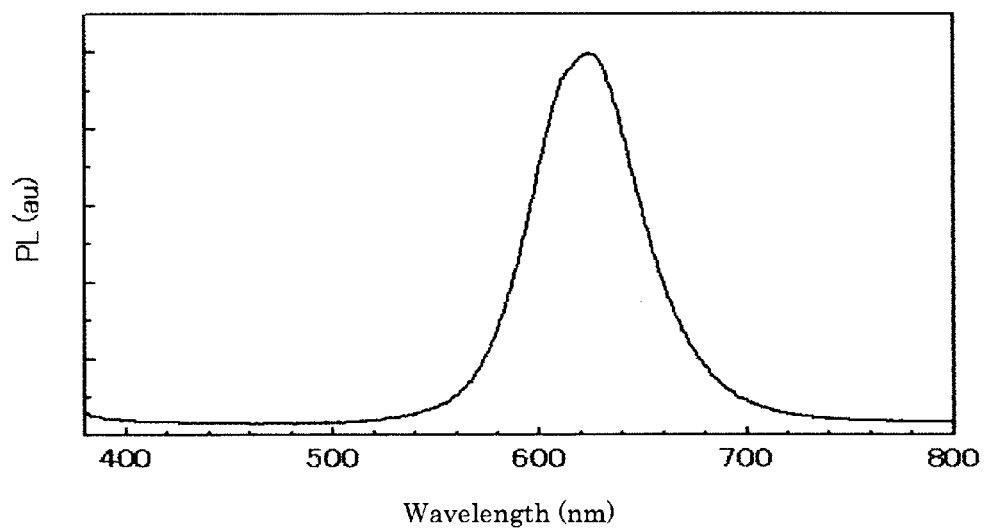
FIG. 19 is a photoluminescence (PL) spectrum of a toluene solution of a semiconductor nanocrystal obtained from carbazole derivative 7 of the present invention.

FIG. 19 is a PL spectrum (excitation light: 365 nm) of a toluene solution of the obtained semiconductor nanocrystal.

Example 18

The procedure of Example 11 was repeated, except that the carbazole derivative 8 obtained in Example 8 was used, to thereby obtain a semiconductor nanocrystal containing the carbazole derivative 8 bonded thereto via a coordination bond or intermolecular force.

Figure 20:
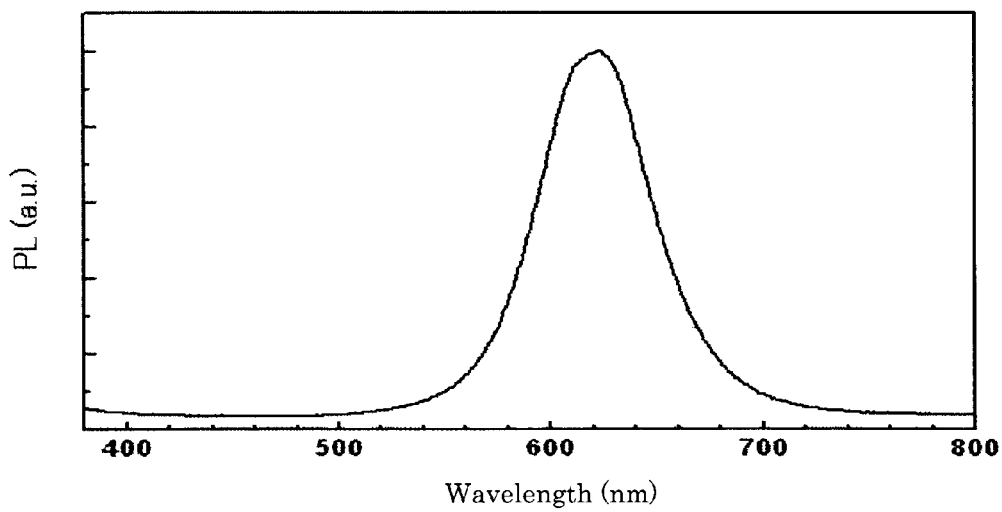
FIG. 20 is a photoluminescence (PL) spectrum of a toluene solution of a semiconductor nanocrystal obtained from carbazole derivative 8 of the present invention.

FIG. 20 is a PL spectrum (excitation light: 365 nm) of a toluene solution of the obtained semiconductor nanocrystal.

Example 19

The procedure of Example 11 was repeated, except that the carbazole derivative 9 obtained in Example 9 was used, to thereby obtain a semiconductor nanocrystal containing the carbazole derivative 9 bonded thereto via a coordination bond or intermolecular force.

Figure 21:
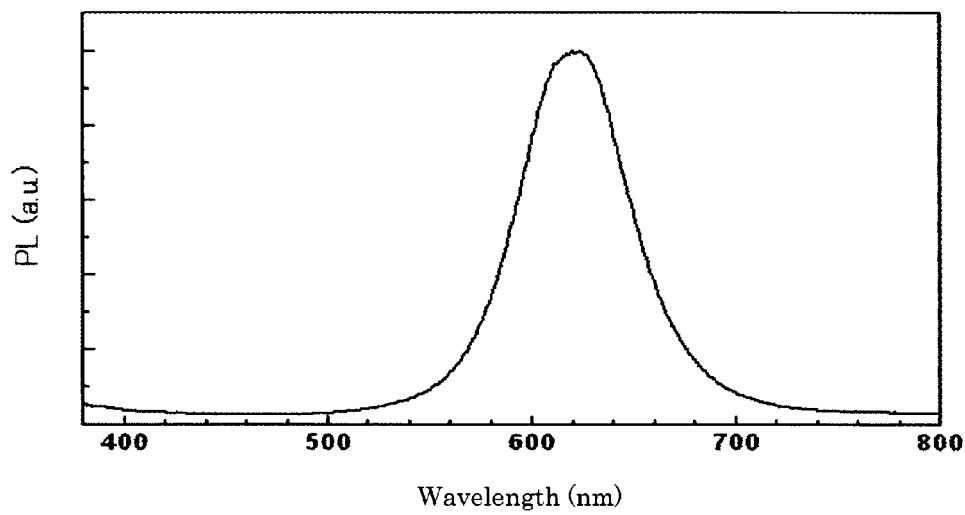
FIG. 21 is a photoluminescence (PL) spectrum of a toluene solution of a semiconductor nanocrystal obtained from carbazole derivative 9 of the present invention.

FIG. 21 is a PL spectrum (excitation light: 365 nm) of a toluene solution of the obtained semiconductor nanocrystal.

Example 20

Synthesis of Carbazole Derivative 11

3,6-Dibromocarbazole (0.75 g) and p-triphenylsilylbenzeneboronic acid neopentyl glycol ester (2.24 g) were added to a solvent mixture of toluene (10 mL) and ethanol (2 mL), followed by bubbling with nitrogen. Then, tetrakistriphenylphosphine palladium (80 mg) and 21.2% aqueous sodium carbonate solution (4.70 g) were added to the mixture, and the resultant mixture was refluxed under nitrogen flow for 16 hours. The mixture was diluted with toluene. The toluene layer was washed with water and dried and the toluene was evaporated. The residue was treated through silica gel column chromatography (eluent: toluene), to thereby obtain 1.30 g of 3,6-bis(4-triphenylsilylphenyl)carbazole as colorless powder.

Melting point>250° C.

Infrared absorption spectrum (KBr) cm$^{-1}$ νNH3463, 3423 νSi-Ar1427, 1109

The 3,6-bis(4-triphenylsilylphenyl)carbazole (1.30 g), 4-(8-hydroxyoctyloxy)iodobenzene (0.65 g), potassium carbonate (0.54 g), copper powder (0.4 g) and nitrobenzene (5 mL) were stirred under nitrogen flow at 195° C. for 16 hours. The resultant mixture was filtrated through CELITE and the solvent was evaporated. The residue was treated through silica gel column chromatography (eluent: 10% ethyl acetate/toluene solution), to thereby obtain 1.50 g (89.8%) of 3,6-bis (4-triphenylsilylphenyl)-N-[4-(8-hydroxyoctyloxyphenyl] carbazole as colorless needle crystals.

Melting point: 217° C. to 218° C.

Infrared absorption spectrum (KBr) cm$^{-1}$ νOH 3400 νSi-Ar1427, 1110

The 3,6-bis(4-triphenylsilylphenyl)-N-[4-(8-hydroxyoctyloxyphenyl)]carbazole was tosylated, thioacetylated and hydrolyzed in the same manner as in Example 2, to thereby obtain 3,6-bis(4-triphenylsilylphenyl)-N-[4-(8-mercaptooctyloxyphenyl)]carbazole (carbazole derivative 11) of the present invention expressed by the following formula (XI) as colorless needle crystals.

Figure 25:
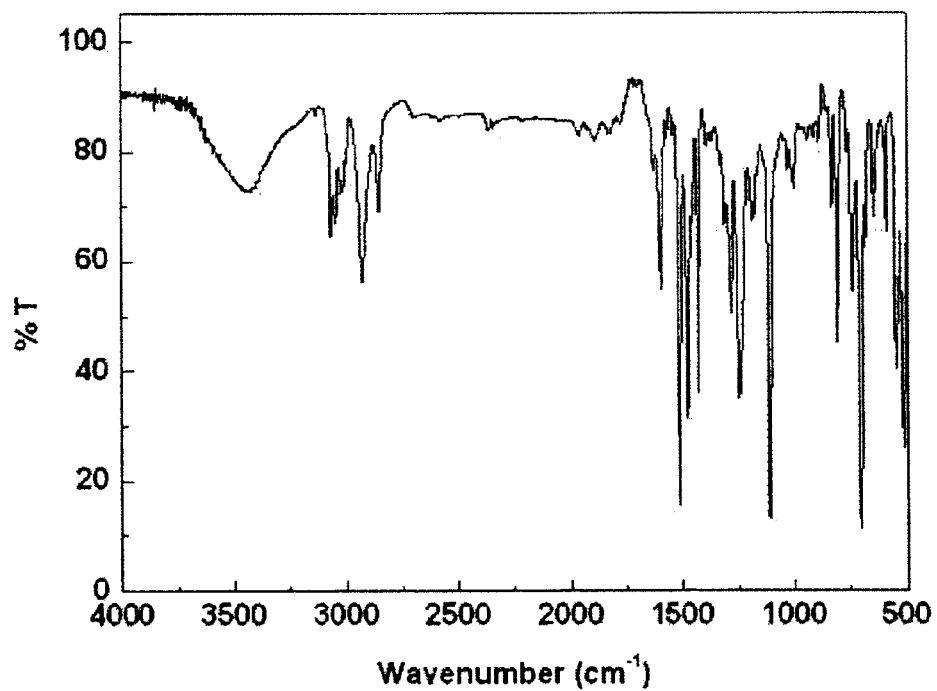
FIG. 25 is an infrared absorption spectrum of carbazole derivative 11 of the present invention.

FIG. 25 is an infrared absorption spectrum (the KBr tablet method) of the obtained carbazole derivative 11.

Melting point>220° C.

Infrared absorption spectrum (KBr) cm$^{-1}$ νSi-Ar1428, 1109

Elemental analysis (%) found (calculated) C, 82.60 (82.87) H, 6.09 (6.11) N, 1.24 (1.31) S, 2.98 (2.99)

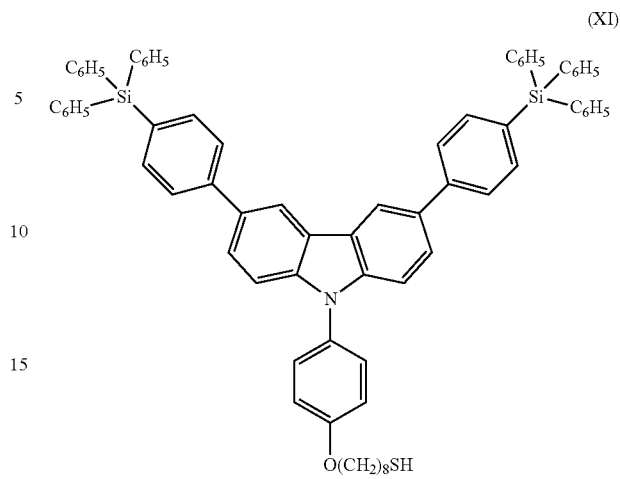

(XI)

Example 21

Synthesis of Carbazole Derivative 12

2,7-Dibromo-N-(4-hydroxyphenyl)carbazole (1.24 g) and 60% sodium hydride (0.11 g) were added at 0° C. to N,N-dimethylformamide (DMF) (40 mL), followed by stirring for 1 hour. Then, 8-bromooctanol (0.65 g) was added thereto, and the mixture was stirred at room temperature for 3 hours and at 50° C. for 2 hours. The resultant mixture was extracted with ethyl acetate, washed with water and dried. The crude product was treated through silica gel column chromatography (eluent: 25% ethyl acetate/toluene solution), to thereby obtain 1.30 g of 2,7-dibromo-N-4-[(8-hydroxyoctyloxyphenyl]carbazole as colorless viscous liquid.

The 2,7-dibromo-N-4-[(8-hydroxyoctyloxyphenyl]carbazole (1.30 g) and p-triphenylsilylbenzeneboronic acid neopentyl glycol ester (2.35 g) were added to a solvent mixture of toluene (15 mL) and ethanol (3 mL), followed by bubbling with nitrogen. Then, tetrakistriphenylphosphine palladium (83 mg) and 21.2% aqueous sodium carbonate solution (4.81 g) were added to thereto, and the mixture was refluxed under nitrogen flow for 6 hours. The resultant mixture was diluted with toluene, and the toluene layer was washed with water and dried and the toluene was evaporated. The residue was treated through silica gel column chromatography (eluent: 20% ethyl acetate/toluene solution), to thereby obtain 1.60 g of 2,7-bis(4-triphenylsilylphenyl)-N-4-[(8-hydroxyoctyloxyphenyl)]carbazole as colorless needle crystals.

Melting point>220° C.

Infrared absorption spectrum (KBr) cm$^{-1}$ νOH 3420 νSi-Ar 1428, 1109

The 2,7-bis(4-triphenylsilylphenyl)-N-4-[(8-hydroxyoctyloxyphenyl)]carbazole was tosylated, thioacetylated and hydrolyzed in the same manner as in Example 2, to thereby obtain 2,7-bis(4-triphenylsilylphenyl)-N-[4-(8-mercaptooctyloxyphenyl)]carbazole (carbazole derivative 12) of the present invention expressed by the following Chemical Formula (XII) as colorless needle crystals.

Figure 26:
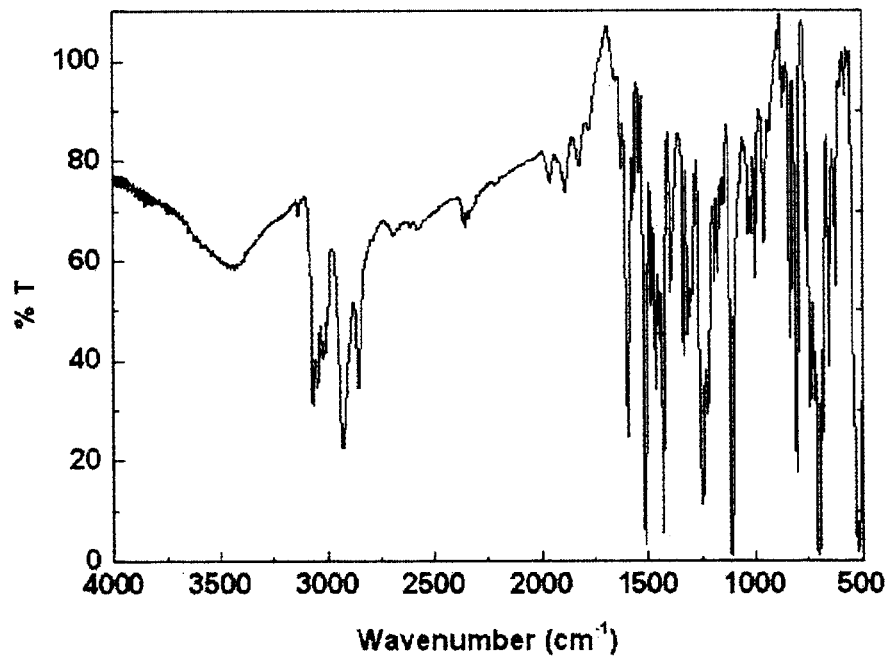
FIG. 26 is an infrared absorption spectrum of carbazole derivative 12 of the present invention.

FIG. 26 is an infrared absorption spectrum (KBr tablet method) of the obtained carbazole derivative 12.

Melting point>220° C.

Infrared absorption spectrum (KBr) cm$^{-1}$ νSi-Ar 1428, 1109

Elemental analysis (%) found (calculated) C, 82.79 (82.87) H, 6.04 (6.11) N, 1.16 (1.31) S, 3.00 (2.99)

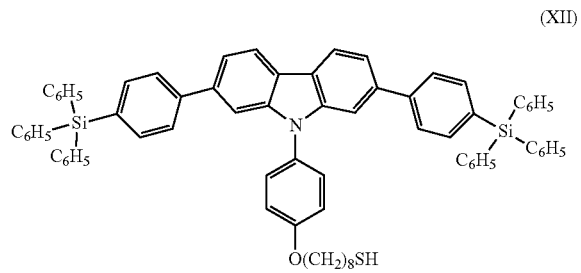

(XII)

Example 22

Synthesis of Carbazole Derivative 13 p-Dibromobenzene (8.91 g) was dissolved in tetrahydrofuran (THF) (30 mL). A 1.63M hexane solution of n-butyllithium (23.2 mL) was added to the solution at −78° C., followed by stirring at −75° C. for 30 min. A solution of dimethylboronfluoride (10.14 g) in tetrahydrofuran (THF) (20 mL) was added dropwise to the mixture. The resultant mixture was stirred at −70° C. for 30 min and then stirred at room temperature overnight. An aqueous ammonium chloride solution was added to the mixture. The resultant mixture was extracted with ethyl acetate, washed with water and dried, and the solvent was evaporated. The residue was treated through silica gel column chromatography (eluent: toluene/hexane=1/4 (by mass)), to thereby obtain 12.3 g of 4-dimesitylborylbromobenzene as colorless needle crystals.

Melting point: 187° C.

Infrared absorption spectrum (KBr) cm$^{-1}$ νB-C 1240, 1225, 1214, 1155

NMR (CDCl$_3$) δ 7.47 (d, aromatic, 2H) 7.35 (d, aromatic, 2H) 6.80 (s, aromatic, 4H) 2.29 (s, CH$_3$, 6H) 1.97 (s, CH$_3$, 12H)

Dioxane (150 mL) was added to the 4-dimesitylborylbromobenzene (12.3 g), bis(neopentylglycolate)diboron (8.20 g) and potassium acetate (8.95 g), followed by bubbling with nitrogen for 30 min. PdCl$_2$(dppf)·CH$_2$Cl$_2$; [1,1'-bis(diphenylphosphino)ferrocene]palladium dichloride dichloromethane adduct (0.75 g) was added thereto, and the mixture was refluxed under nitrogen flow for 40 min. After left to cool to room temperature, the mixture was extracted with ethyl acetate, washed with water and dried and the solvent was evaporated. The residue was treated through silica gel column chromatography (eluent: 5% ethyl acetate/toluene solution) and then recrystallized from a solvent mixture of toluene/ethanol (1/1 by volume), to thereby obtain 9.02 g of 4-dimesitylborylbenzeneboronic acid neopentyl glycol ester as colorless plate-like crystals.

Melting point: 185.0° C. to 187.0° C.

Infrared absorption spectrum (KBr) cm$^{-1}$ νB-C 1132 νB-C 1376, 1341, 1317

NMR (CDCl$_3$) δ7.75 (d, aromatic, 2H) 7.49 (d, aromatic, 2H) 6.80 (s, aromatic, 4H) 3.77 (s, CH$_2$, 4H) 2.30 (s, CH$_3$,6H) 1.98 (s, CH$_3$, 12H) 1.03 (s, CH$_3$, 6H)

3,6-Dibromo-N-(4-methoxyphenyl)carbazole (2.16 g) and 4-dimesitylborylbenzeneboronic acid neopentyl glycol ester (4.61 g) were added to a solvent mixture of toluene (30 mL) and ethanol (6 mL), followed by bubbling with nitrogen. Then, tetrakistriphenylphosphine palladium (174 mg) and 21.2% aqueous sodium carbonate solution (10.1 g) were added to the mixture, and the resultant mixture was refluxed under nitrogen flow for 3 hours. The mixture was diluted with toluene. The toluene layer was washed with water and dried and the toluene was evaporated. The residue was treated through silica gel column chromatography (eluent: toluene/hexane=1/2 (by mass)), to thereby obtain 3.22 g of 3,6-bis(4-dimesitylborylphenyl)-N-(4-methoxyphenyl)carbazole as colorless powder.

Melting point: 202° C.

The 3,6-bis(4-dimesitylborylphenyl)-N-(4-methoxyphenyl)carbazole was subjected to demethylation with boron tribromide, and then was reacted with 8-bromooctanol in the same manner as in Example 2, to thereby obtain 3,6-bis(4-dimesitylborylphenyl)-N-[4-(8-hydroxyoctyloxyphenyl)] carbazole.

The 3,6-bis(4-dimesitylborylphenyl)-N-[4-(8-hydroxyoctyloxyphenyl)]carbazole was tosylated, thioacetylated and hydrolyzed in the same manner as in Example 2, to thereby obtain 3,6-bis(4-dimesitylborylphenyl)-N-[4-(8-mercaptooctyloxyphenyl)]carbazole (carbazole derivative 13) of the present invention expressed by the following Chemical Formula (XIII) as colorless powder.

Figure 27:
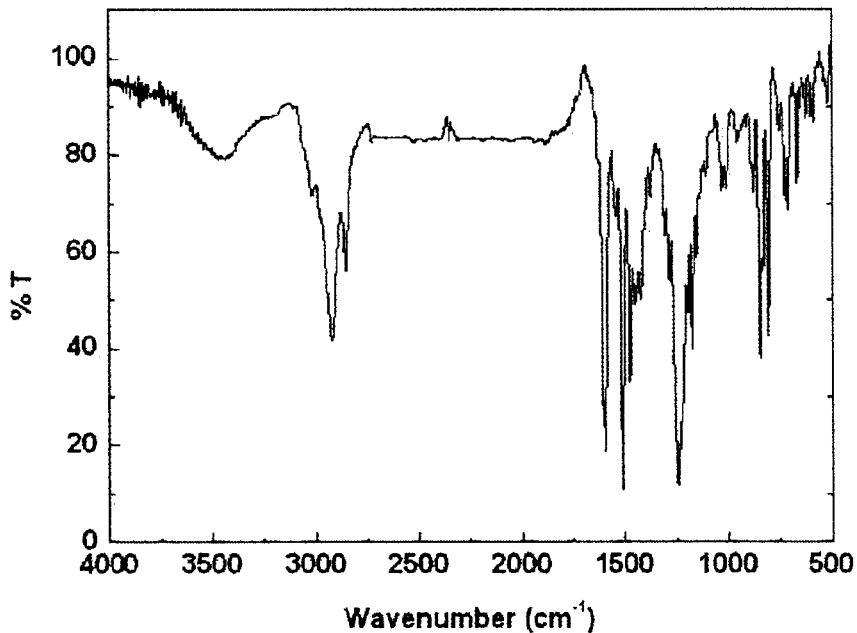
FIG. 27 is an infrared absorption spectrum of carbazole derivative 13 of the present invention.

FIG. 27 is an infrared absorption spectrum (KBr tablet method) of the obtained carbazole derivative 13.

Melting point: sintering at 190° C.

Infrared absorption spectrum (KBr) cm$^{-1}$ νB-C 1240

Elemental analysis (%) found (calculated) C, 84.40 (84.48) H, 7.40 (7.57) N, 1.17 (1.33) S, 2.96 (3.05)

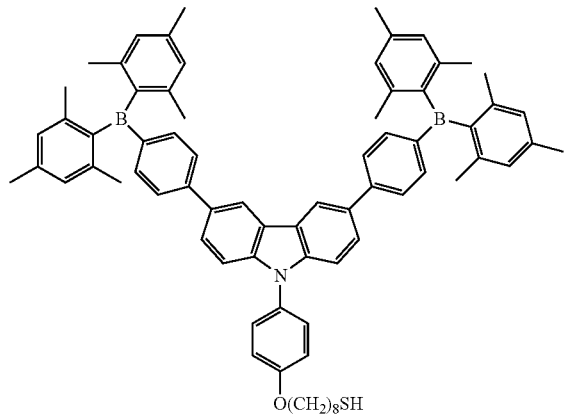

(XIII)

Example 23

Synthesis of Carbazole Derivative 14

3,6-Dibromo-N-(4-methylphenyl)carbazole (6.23 g) and phenylboronic acid (2.01 g) were added to a solvent mixture of toluene (60 mL) and ethanol (15 mL), followed by bubbling with nitrogen. Then, tetrakistriphenylphosphine palladium (290 mg) and 21.2% aqueous sodium carbonate solution (15.0 g) were added to the mixture, and the resultant mixture was refluxed under nitrogen flow for 5 hours. The mixture was diluted with toluene. The toluene layer was washed with water and dried and the toluene was evaporated. The residue was treated through silica gel column chromatography (eluent: toluene/hexane=1/4 (by mass)), to thereby obtain 3.20 g of 3-bromo-6-phenyl-N-(4-methylphenyl)carbazole as colorless powder.

The 3-bromo-6-phenyl-N-(4-methylphenyl)carbazole (3.20 g) and 4-methoxyphenylboronic acid (1.65 g) were added to a solvent mixture of toluene (30 mL) and ethanol (8 mL), followed by bubbling with nitrogen. Then, tetrakistriphenylphosphine palladium (150 mg) and 21.2% aqueous sodium carbonate solution (7.80 g) were added to the mixture, and the resultant mixture was refluxed under nitrogen flow for 3 hours. The mixture was diluted with toluene. The toluene layer was washed with water and dried and the toluene was evaporated. The residue was treated through silica gel column chromatography (eluent: toluene), to thereby obtain 2.30 g of 3-phenyl-6-(4-methoxyphenyl)-N-(4-methylphenyl)carbazole as colorless powder.

The 3-phenyl-6-(4-methoxyphenyl)-N-(4-methylphenyl)carbazole was subjected to demethylation with boron tribromide and then to etherification with 8-bromooctanol/sodium hydride (1/1 by mole), to thereby obtain 3-phenyl-6-[4-(8-hydroxyoctyloxyphenyl)-N-(4-methylphenyl)]carbazole.

The 3-phenyl-6-[4-(8-hydroxyoctyloxyphenyl)-N-(4-methylphenyl)]carbazole was tosylated, thioacetylated and hydrolyzed in the same manner as in Example 2, to thereby obtain 3-phenyl-6-[4-(8-mercaptooctyloxyphenyl)-N-(4-methylphenyl)carbazole (carbazole derivative 14) of the present invention expressed by the following Chemical Formula (XIV) as colorless prism crystals.

Figure 28:
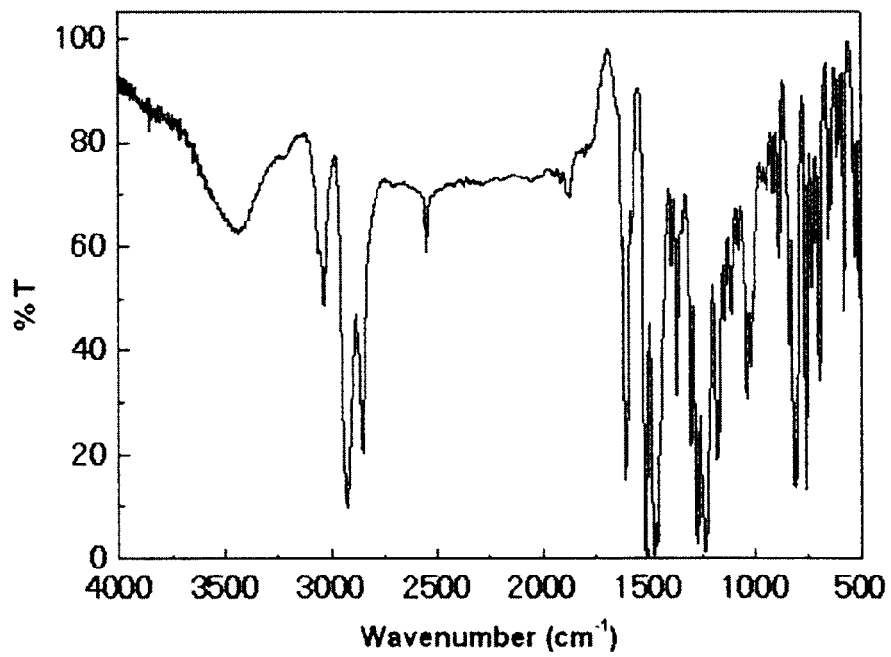
FIG. 28 is an infrared absorption spectrum of carbazole derivative 14 of the present invention.

FIG. 28 is an infrared absorption spectrum (KBr tablet method) of the obtained carbazole derivative 14.

Melting point: 103.0° C. to 104.5° C.

Infrared absorption spectrum (KBr) cm$^{-1}$ νSH 2550

Elemental analysis (%) found (calculated) C, 82.06 (82.21) H, 6.83 (6.90) N, 2.29 (2.46) S, 5.62 (5.63)

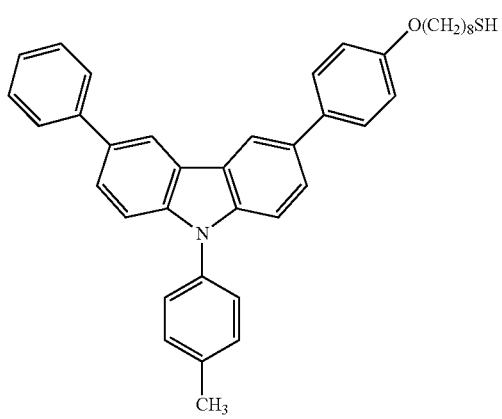

(XIV)

Example 24

Synthesis of Carbazole Derivative 15

The procedure of Example 1 was repeated, except that 5-methyl-2-thiophene boronic acid was changed to 2,4,6-trimethylphenylboronic acid, to thereby obtain 3,6-dimesitylcarbazole N-[4-(8-mercaptooctyloxyphenyl)]carbazole (carbazole derivative 15) of the present invention expressed by the following Chemical Formula (XV) as colorless viscous liquid.

Figure 29:
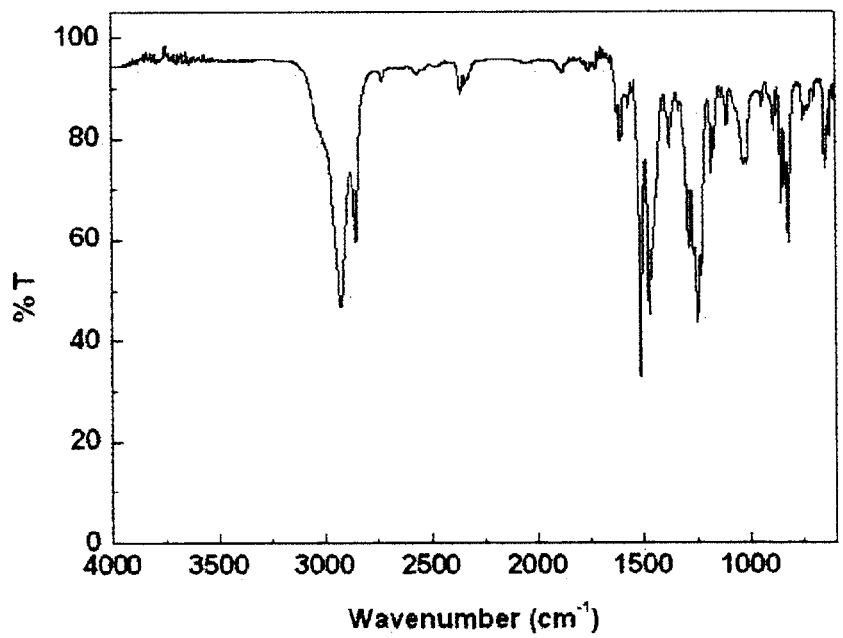
FIG. 29 is an infrared absorption spectrum of carbazole derivative 15 of the present invention.

FIG. 29 is an infrared absorption spectrum (KBr tablet method) of the obtained carbazole derivative 15.

Elemental analysis (%) found (calculated) C, 82.49 (82.58) H, 7.92 (7.72) N, 1.95 (2.19) S, 4.72 (5.01)

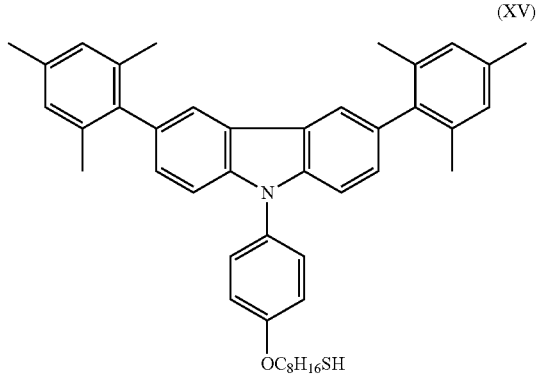

(XV)

Example 25

Synthesis of Carbazole Derivative 16

The procedure of Example 2 was repeated, except that 8-bromo-1-octanol was changed to 12-bromo-1-dodecanol, to thereby obtain 3,6-diphenyl-N-[4-(12-mercaptododecyloxyphenyl)]carbazole (carbazole derivative 16) of the present invention expressed by the following Chemical Formula (XVI) as colorless powder.

Figure 30:
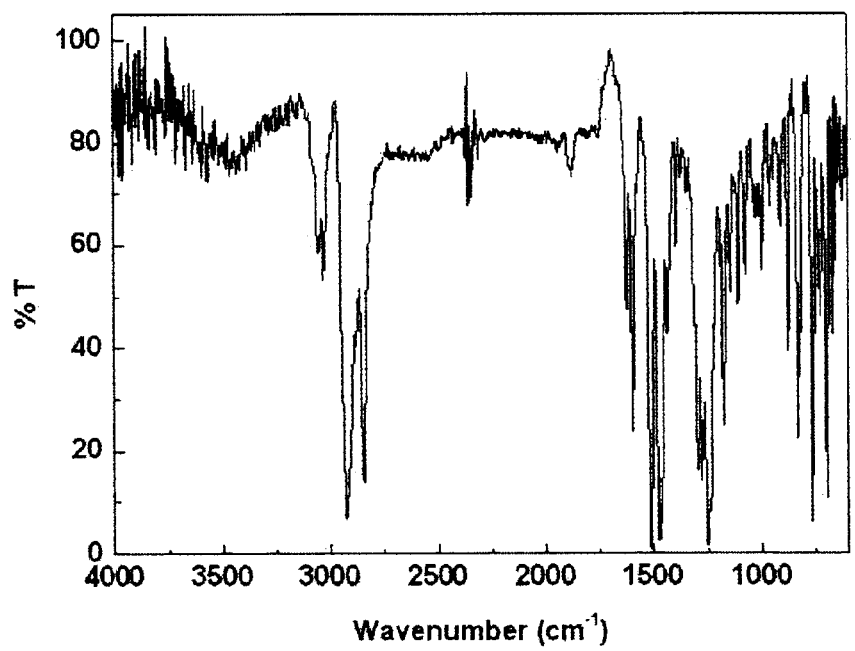
FIG. 30 is an infrared absorption spectrum of carbazole derivative 16 of the present invention.

FIG. 30 is an infrared absorption spectrum (KBr tablet method) of the obtained carbazole derivative 16.

Melting point: 103.5° C. to 104.5° C.

Elemental analysis (%) found (calculated) C, 82.38 (82.44) H, 7.29 (7.41) N, 2.13 (2.29) S, 5.11 (5.24)

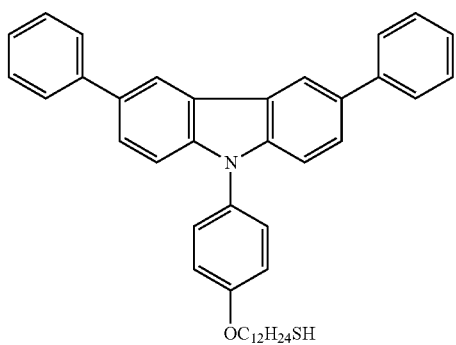

(XVI)

Example 26

Synthesis of Carbazole Derivative 17

9-Acetyl-3,6-diiodocarbazole (10.0 g) and triphenylsilane (12.4 g) were dry N-methylpyrrolidone (200 mL), followed by bubbling with argon gas for 30 min. Tripotassium phosphate (27.6 g) and bis(tri-t-butylphosphine)palladium (0.111 g) were added thereto, and the mixture was stirred at room temperature for 19 hours. The obtained reaction mixture was filtrated, and the filtrate was extracted with methylene chloride. The separated organic layer was washed with brine and dried, and the methylene chloride was evaporated. The residue was treated through silica gel column chromatography (eluent: toluene), to thereby obtain 1.97 g of 9-acetyl-3,6-bis (triphenylsilyl)carbazole as colorless powder.

The obtained 9-acetyl-3,6-bis(triphenylsilyl)carbazole (1.97 g) was dissolved in tetrahydrofuran (50 mL). A 50% by mass aqueous sodium hydroxide solution (1.1 g) was added to the solution. The resultant mixture was stirred at 50° C. for 3 hours and cooled to room temperature. Diluted hydrochloric acid was added thereto until the pH reached 5, followed by stirring for 30 min. The mixture was extracted with methylene chloride. The separated organic layer was washed with water and dried, and the methylene chloride was evaporated. The residue was purified with a recycle HPLC (name of apparatus: Recycling Preparative HPLC LC-9201, product of Japan Analytical Industry Co., Ltd., developing solvent: THF, flow rate: 3.5 mL/min), to thereby obtain 1.28 g of 3,6-bis(triphenylsilyl)carbazole as colorless powder.

Next, the obtained 3,6-bis(triphenylsilyl)carbazole was aminated, tosylated, thioacetylated and hydrolyzed in the same manner as in Example 6, to thereby obtain 3,6-bis (triphenylsilyl)-N-[4-(8-mercaptooctyloxyphenyl)]carbazole (carbazole derivative 17) of the present invention expressed by the following Chemical Formula (XVII) as pale yellow powder.

Figure 31:
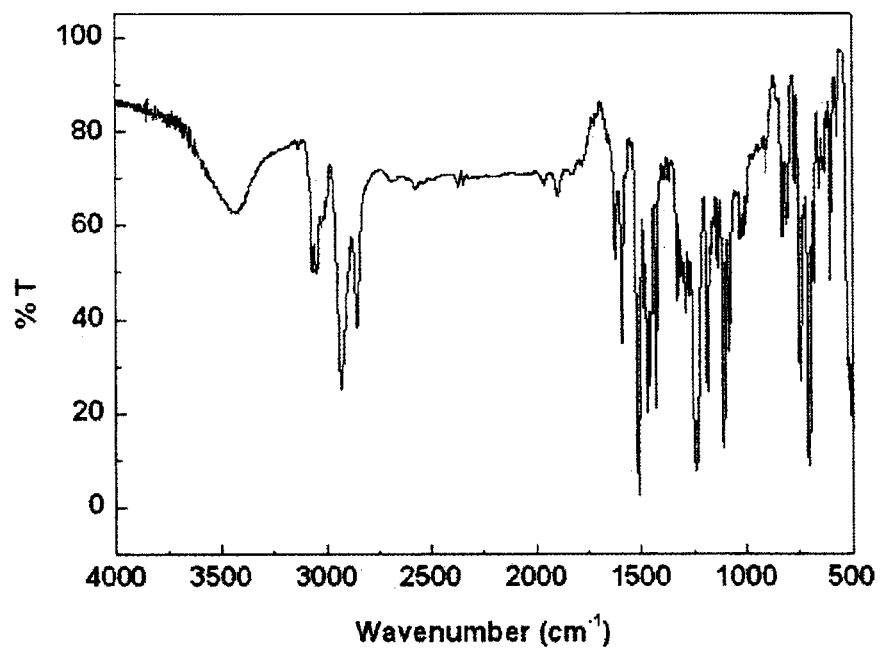
FIG. 31 is an infrared absorption spectrum of carbazole derivative 17 of the present invention.

FIG. 31 is an infrared absorption spectrum (KBr tablet method) of the obtained carbazole derivative 17.

Infrared absorption spectrum (KBr) cm$^{-1}$ νSH 2570

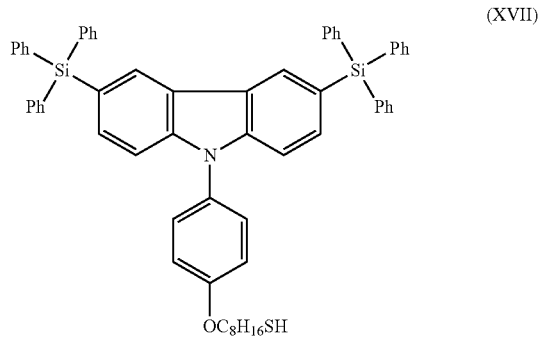

(XVII)

Application Example 1

A 110 nm-thick ITO glass substrate was ultrasonically washed with sequentially a neutral detergent, acetone and isopropanol. The glass substrate was washed with boiled isopropanol and treated in a UV-ozone chamber for 12 min.

The ITO substrate was spin-coated with Baytron (registered trademark) P AI 4083 (product of H. C. Starck Co.) (PEDOT-PSS solution), followed by drying at 150° C. for 30 min, to thereby form a hole injection layer having a thickness of 40 nm.

In a nitrogen atmosphere, the formed hole injection layer was spin-coated with a chloroform solution of polycarbonate, followed by drying at 100° C. for 30 min, to thereby form a hole transport layer having a thickness of 40 nm. Notably, the polycarbonate used was the polycarbonate, described in Example 1 of JP-A No. 2005-54165, containing a constituent unit derived from 3,6-bis(4-hydroxyphenyl)-N-phenylcarbazole and a constituent unit derived from 4,4'-isoprypylidenediphenol at a mole ratio of 1:1.

In a nitrogen atmosphere, the formed hole transport layer was spin-coated with a dispersion liquid prepared by dispersing in toluene the semiconductor nanocrystal containing the carbazole derivative 2 bonded thereto via a coordination bond or intermolecular force, followed by drying at 100° C. for 30 min, to thereby form a light emitting layer having a thickness of 15 nm.

A vacuum vapor device was used to vapor deposit 3,5,3',5' tetrakis(m-pyrid-3-yDphenyl-[1,1]biphenyl on the light emitting layer under vacuum at $1\times10^{-4}$ Pa, to thereby form an electron transport layer having a thickness of 50 nm. Next, MgAg and Ag were vapor deposited thereon through a shadow mask so as to have thicknesses of 100 nm and 10 nm, respectively, to form a cathode, whereby an electroluminescence (EL) element was obtained.

The obtained EL element was measured for current density, voltage, external quantum efficiency and light emission spectrum using an external quantum efficiency measuring device (product of Hamamatsu Photonics K.K., conditions: voltage applied stepwise from 0 V to 30 V).

Figure 22:
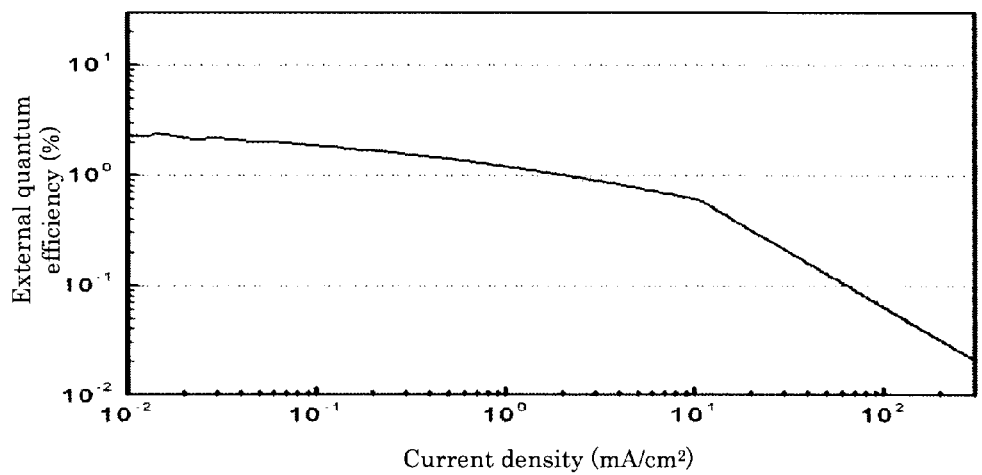
FIG. 22 is a graph of a relation between current density and external quantum efficiency of an EL element produced from a semiconductor nanocrystal obtained from carbazole derivative 2 of the present invention.

FIG. 22 is a graph of a relation between current density and external quantum efficiency of the EL element. From FIG. 22, the EL element was found to have the maximum external quantum efficiency of 2.3%.

Figure 23:
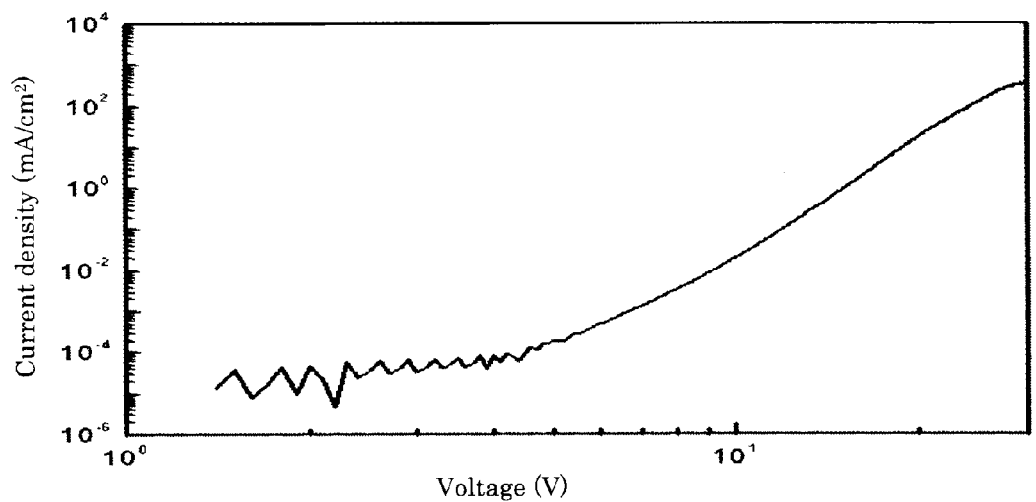
FIG. 23 is a graph of a relation between voltage and current density of an EL element used in the present invention.

FIG. 23 is a graph of a relation between voltage and current density of the EL.

Figure 24:
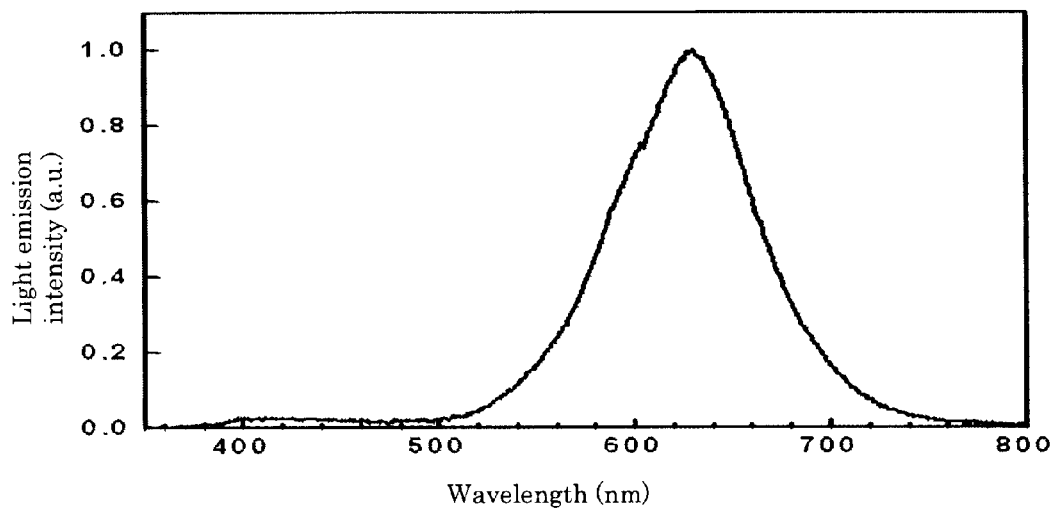
FIG. 24 is a graph of light emission spectrum when the currenct density of an EL element of the present invention is 1 mA/cm$^2$.

FIG. 24 is a graph of light emission spectrum when the current density of the EL element was 1 mA/cm$^2$. From FIG. 24, the EL element was found to have a peak wavelength of 624 nm.

Aspects of the present invention are as follows.

<1> A carbazole derivative represented by the following General Formula (1) where at least one aromatic ring has one to three substituents each represented by the following General Formula (2):

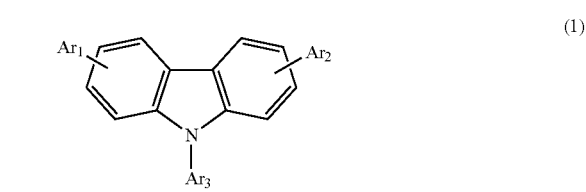

(1)

in General Formula (1), Ar$_1$ and Ar$_2$ each independently represent a substituted or unsubstituted aryl group which may form a ring with a benzene ring, a substituted or unsubstituted heterocyclic group, a substituted or unsubstituted arylsilyl group, or a hydrogen atom, and Ar$_3$ represents a substituted or unsubstituted aryl group,

(2)

in General Formula (2), X represents a methylene group, a carbonyloxy group, an oxycarbonyl group, a carbonyl group, an oxygen atom or a sulfur atom, Y represents a substituted or unsubstituted alkylene group, and Z represents a carboxyl group, a hydroxyl group or a thiol group.

<2> The carbazole derivative according to <1>, wherein the carbazole derivative is represented by the following General Formula (3):

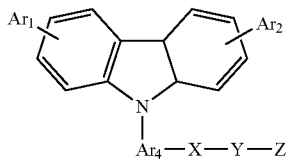
(3)

in General Formula (3), Ar$_4$ represents a substituted or unsubstituted arylene group, and Ar$_1$, Ar$_2$, X, Y and Z are as defined in General Formulas (1) and (2).

<3> The carbazole derivative according to <2>, wherein Ar$_1$ and Ar$_2$ in General Formula (3) each independently represent a group represented by the following General Formula (4):

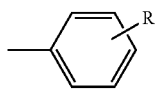
(4)

in General Formula (4), R represents a hydrogen atom, a substituted or unsubstituted alkyl group, a substituted or unsubstituted alkoxy group, a halogen atom or a substituted or unsubstituted aryl group.

<4> The carbazole derivative according to <2>, wherein the carbazole derivative is represented by the following General Formula (5):

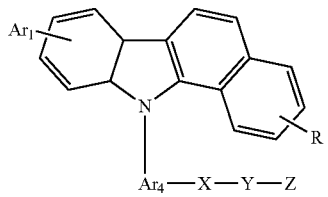
(5)

in General Formula (5), R represents a hydrogen atom, a substituted or unsubstituted alkyl group, a substituted or unsubstituted alkoxy group, a halogen atom or a substituted or unsubstituted aryl group, and Ar$_1$, Ar$_4$, X, Y and Z are as defined in General Formulas (1) to (3).

<5> The carbazole derivative according to <1>, wherein the carbazole derivative is represented by the following General Formula (6):

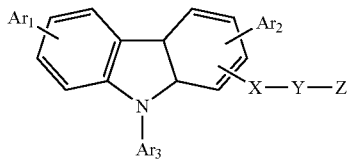
(6)

in General Formula (6), Ar$_1$, Ar$_2$, Ar$_3$, X, Y and Z are as defined in General Formulas (1) and (2).

<6> A semiconductor nanocrystal including:
a carbazole derivative bonded to the semiconductor nanocrystal via a coordination bond or intermolecular force,
wherein the carbazole derivative is represented by the following General Formula (1) where at least one aromatic ring has one to three substituents each represented by the following General Formula (2):

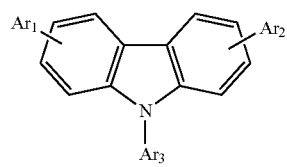
(1)

in General Formula (1), Ar$_1$ and Ar$_2$ each independently represent a substituted or unsubstituted aryl group which may form a ring with a benzene ring, a substituted or unsubstituted heterocyclic group, a substituted or unsubstituted arylsilyl group, or a hydrogen atom, and Ar$_3$ represents a substituted or unsubstituted aryl group,

—X—Y—Z        (2)

in General Formula (2), X represents a methylene group, a carbonyloxy group, an oxycarbonyl group, a carbonyl group, an oxygen atom or a sulfur atom, Y represents a substituted or unsubstituted alkylene group, and Z represents a carboxyl group, a hydroxyl group or a thiol group.

This application claims priority to Japanese application Nos. 2011-166230, filed on Jul. 29, 2011, and 2012-013021, filed on Jan. 25, 2012 and incorporated herein by reference.

What is claimed is:
1. The carbazole derivative represented by formula (3):

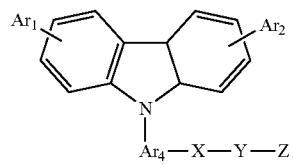
(3)

wherein
Ar$_1$ and Ar$_2$ each independently represent a group represented by formula (4):

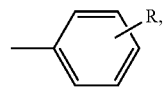
(4)

R represents a hydrogen atom, a substituted or unsubstituted alkyl group, a substituted or unsubstituted alkoxy group, a halogen atom or a substituted or unsubstituted aryl group,
Ar$_4$ represents a substituted or unsubstituted arylene group,
X represents a methylene group, a carbonyloxy group, an oxycarbonyl group, a carbonyl group, an oxygen atom or a sulfur atom,
Y represents a substituted or unsubstituted alkylene group, and Z represents a carboxyl group, a hydroxyl group or a thiol group.

2. A carbazole derivative represented by formula (5):

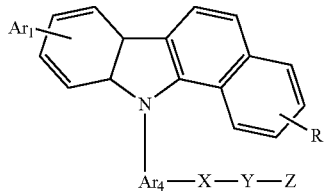

wherein
 Ar$_1$ represents a substituted or unsubstituted aryl group which may form a ring with the adjacent benzene ring, a substituted or unsubstituted heterocyclic group, a substituted or unsubstituted arylsilyl group, or a hydrogen atom,
 Ar$_4$ represents a substituted or unsubstituted arylene group,
 R represents a hydrogen atom, a substituted or unsubstituted alkyl group, a substituted or unsubstituted alkoxy group, a halogen atom or a substituted or unsubstituted aryl group,
 X represents a methylene group, a carbonyloxy group, an oxycarbonyl group, a carbonyl group, an oxygen atom or a sulfur atom,
 Y represents a substituted or unsubstituted alkylene group, and
 Z represents a carboxyl group, a hydroxyl group or a thiol group.

3. A semiconductor nanocrystal comprising the carbazole derivative according to claim 1 bonded to the semiconductor nanocrystal via a coordination bond or intermolecular force.

4. A semiconductor nanocrystal comprising the carbazole derivative according to claim 2 bonded to the semiconductor nanocrystal via a coordination bond or intermolecular force.

* * * * *